(12) United States Patent
Chenal

(10) Patent No.: US 12,047,732 B2
(45) Date of Patent: Jul. 23, 2024

(54) TUNED-FREQUENCY-SPECTRUM EARPIECE

(71) Applicant: JMJ Holdings, LLC, Frederic, WI (US)

(72) Inventor: David M. Chenal, Frederic, WI (US)

(73) Assignee: JMJ Holdings, LLC, Frederic, WI (US)

( * ) Notice: Subject to any disclaimer, the term of this patent is extended or adjusted under 35 U.S.C. 154(b) by 0 days.

(21) Appl. No.: 18/371,400

(22) Filed: Sep. 21, 2023

(65) Prior Publication Data

US 2024/0107222 A1     Mar. 28, 2024

Related U.S. Application Data

(60) Provisional application No. 63/409,408, filed on Sep. 23, 2022.

(51) Int. Cl.
*A61F 11/06* (2006.01)
*H04R 1/10* (2006.01)
(Continued)

(52) U.S. Cl.
CPC ......... *H04R 1/1083* (2013.01); *H04R 1/1016* (2013.01); *H04R 1/22* (2013.01); *H04R 1/30* (2013.01)

(58) Field of Classification Search
CPC ...... H04R 1/1083; H04R 1/1016; H04R 1/22; H04R 1/30
See application file for complete search history.

(56) References Cited

U.S. PATENT DOCUMENTS

| 2,881,759 A | 4/1959 | Hocks et al. |
| 3,783,864 A | 1/1974 | Moller |

(Continued)

FOREIGN PATENT DOCUMENTS

| ES | 2028711 | 7/1992 |
| GB | 2407274 A | 4/2005 |

(Continued)

OTHER PUBLICATIONS

Surefire, LLC, Fountain Valley, California, "EP8 Sonic Defenders", "downloaded from: https://web.archive.org/web/20130524145837/http://www.surefire.com/ep8-sonic-defenders-cobalt.html", May 24, 2013.

*Primary Examiner* — Simon King
(74) *Attorney, Agent, or Firm* — Charles A. Lemaire; Lemaire Patent Law Firm, P.L.L.C.

(57) ABSTRACT

A tuned-frequency-spectrum earpiece for selectively tuning audio frequencies that enter an inner ear of a user wearing the earpiece, the earpiece including a base having an emitter end and receiver end, the base including a channel that passes through an entirety of the base; a sound-attenuation plug, wherein the sound-attenuation plug is configured to couple to the base such that the sound-attenuation plug surrounds at least a portion of the channel of the base; a first filter device configured to insert into the channel of the base and to selectively reject undesired frequencies of the audio frequencies that enter the earpiece; and a frequency-selective sound collector operatively coupled to the receiver end of the base and configured to increase an amount of desired frequencies of the audio frequencies that enter the first filter device. Some embodiments increase the amount of sound from some directions while reducing sound from other directions.

20 Claims, 43 Drawing Sheets

(51) Int. Cl.
   *H04R 1/22*    (2006.01)
   *H04R 1/30*    (2006.01)

(56) References Cited

U.S. PATENT DOCUMENTS

| | | | |
|---|---|---|---|
| 4,167,223 A * | 9/1979 | Liesse | G10K 11/04 |
| | | | 381/67 |
| 4,498,469 A | 2/1985 | Csiki | |
| 5,044,463 A | 9/1991 | Carr | |
| 5,113,967 A | 5/1992 | Killion et al. | |
| 5,488,205 A | 1/1996 | Major | |
| 5,609,164 A | 3/1997 | Dyrud et al. | |
| 5,631,965 A | 5/1997 | Chang | |
| 5,957,136 A | 9/1999 | Magidson | |
| 6,148,821 A | 11/2000 | Falco | |
| 6,938,622 B2 | 9/2005 | Huang | |
| D523,845 S | 6/2006 | Smith et al. | |
| 7,210,484 B1 * | 5/2007 | Tiemens | A61F 11/08 |
| | | | 128/865 |
| 7,236,605 B2 | 6/2007 | Oliviera et al. | |
| 7,394,910 B2 | 7/2008 | Smith et al. | |
| 7,512,243 B2 | 3/2009 | Haussmann | |
| 7,600,604 B2 | 10/2009 | Babcock et al. | |
| 7,743,771 B2 | 6/2010 | Falco | |
| 7,778,435 B2 | 8/2010 | Smith et al. | |
| 7,837,005 B2 | 11/2010 | Killion | |
| 7,934,916 B2 | 5/2011 | Smith et al. | |
| 7,967,015 B2 | 6/2011 | Jenkins | |
| 8,101,103 B2 | 1/2012 | Tiemens et al. | |
| 8,113,207 B2 | 2/2012 | Gehling et al. | |
| 8,161,975 B2 | 4/2012 | Turdjian | |
| 8,224,005 B2 | 7/2012 | Smith | |
| 8,327,973 B2 | 12/2012 | Parish et al. | |
| 8,596,279 B2 | 12/2013 | Falco | |
| 8,611,969 B2 | 12/2013 | Smith et al. | |
| 8,625,834 B2 | 1/2014 | Smith et al. | |
| 8,679,607 B2 | 3/2014 | Hamer et al. | |
| 8,820,470 B2 | 9/2014 | Brown | |
| 8,879,769 B2 | 11/2014 | Smith et al. | |
| 8,960,366 B2 | 2/2015 | Peskar et al. | |
| D727,301 S | 4/2015 | Smith et al. | |
| 9,042,947 B2 | 5/2015 | Smith et al. | |
| 9,088,847 B2 | 7/2015 | Young-Mun | |
| 9,092,965 B2 | 7/2015 | Lyons et al. | |
| D771,599 S | 11/2016 | Kim | |
| 9,603,746 B2 | 3/2017 | Chenal | |
| 9,737,439 B2 | 8/2017 | Endle et al. | |
| 9,807,524 B2 * | 10/2017 | Shennib | H04R 25/652 |
| 9,814,625 B2 | 11/2017 | Ely | |
| D815,619 S | 4/2018 | Moudgill et al. | |
| D819,594 S | 6/2018 | Hosoda et al. | |
| 10,231,048 B2 | 3/2019 | Smith et al. | |
| 10,440,459 B2 | 10/2019 | Smith et al. | |
| 11,229,552 B1 | 1/2022 | Chenal | |
| 2002/0096391 A1 | 7/2002 | Smith et al. | |
| 2002/0181729 A1 | 12/2002 | Smith | |
| 2003/0029460 A1 | 2/2003 | Tiemens | |
| 2003/0116165 A1 | 6/2003 | Huang | |
| 2003/0159878 A1 | 8/2003 | Hakansson et al. | |
| 2006/0042640 A1 * | 3/2006 | Haussmann | A61F 11/08 |
| | | | 128/864 |
| 2006/0045284 A1 * | 3/2006 | Haussmann | A61F 11/08 |
| | | | 381/72 |
| 2006/0045299 A1 * | 3/2006 | Haussmann | A61F 11/08 |
| | | | 381/328 |
| 2008/0181441 A1 | 7/2008 | Smith | |
| 2008/0245372 A1 | 10/2008 | Smith | |
| 2008/0247561 A1 | 10/2008 | Smith | |
| 2008/0253605 A1 | 10/2008 | Smith | |
| 2009/0141923 A1 | 6/2009 | Smith | |
| 2010/0142726 A1 * | 6/2010 | Donaldson | G10K 11/172 |
| | | | 381/94.1 |
| 2010/0195860 A1 | 8/2010 | Becker | |
| 2011/0146420 A1 | 6/2011 | Okada et al. | |
| 2012/0057739 A1 * | 3/2012 | Smith | H04R 1/105 |
| | | | 381/379 |
| 2012/0064845 A1 * | 3/2012 | Smith | H04R 1/1016 |
| | | | 381/74 |
| 2014/0105442 A1 | 4/2014 | Smith et al. | |
| 2014/0254842 A1 | 9/2014 | Smith et al. | |
| 2015/0043767 A1 | 2/2015 | Smith | |
| 2015/0047651 A1 | 2/2015 | Haapapuro et al. | |
| 2015/0335489 A1 | 11/2015 | Hamer et al. | |
| 2016/0166203 A1 * | 6/2016 | Goldstein | A61B 5/02055 |
| | | | 600/509 |
| 2016/0261944 A1 * | 9/2016 | Silvestri | H04R 1/2826 |
| 2017/0034615 A1 * | 2/2017 | Mankodi | A61B 5/6843 |
| 2018/0221209 A1 * | 8/2018 | Ogut | H04R 1/1083 |
| 2019/0158944 A1 * | 5/2019 | Belonozhko | H04R 3/14 |
| 2020/0100021 A1 * | 3/2020 | Pavlov | H04R 1/2842 |
| 2020/0107110 A1 * | 4/2020 | Ji | G01V 3/081 |
| 2020/0188176 A1 * | 6/2020 | Cran | G10K 11/162 |
| 2020/0252711 A1 | 8/2020 | Smith et al. | |
| 2022/0151833 A1 * | 5/2022 | Smith | G10K 11/16 |
| 2023/0058747 A1 | 2/2023 | Chenal | |

FOREIGN PATENT DOCUMENTS

| | | |
|---|---|---|
| WO | WO 2009081067 | 7/2009 |
| WO | WO 2021133747 | 7/2021 |
| WO | WO 2022169769 | 8/2022 |
| WO | WO 2022226213 | 10/2022 |

* cited by examiner

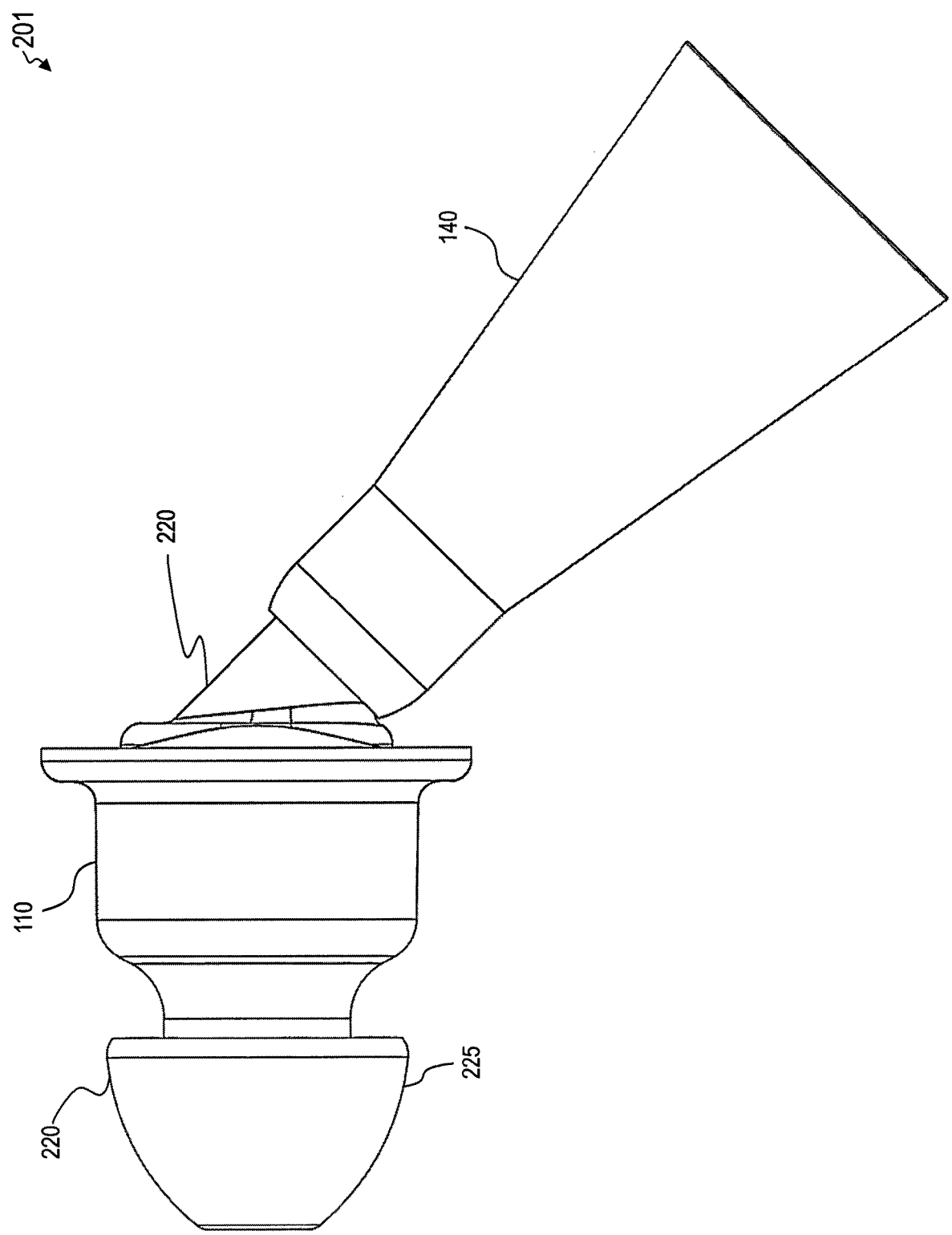

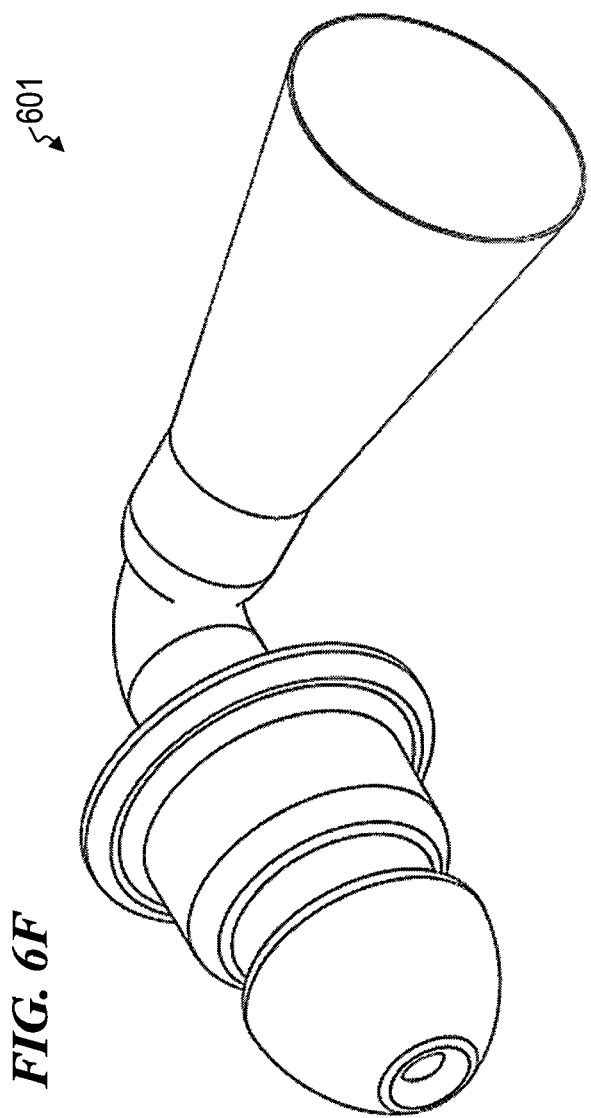
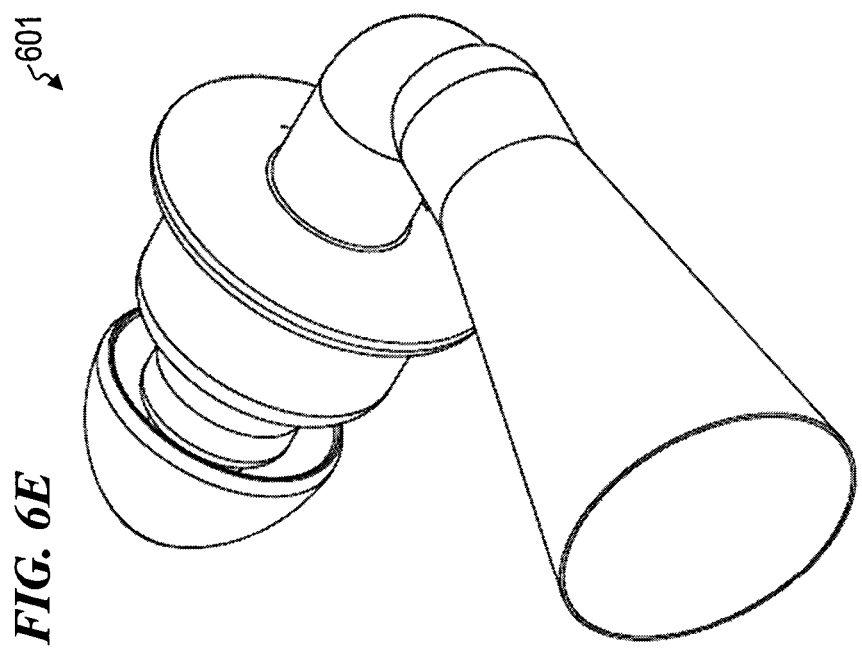
*FIG. 6F*
*FIG. 6E*

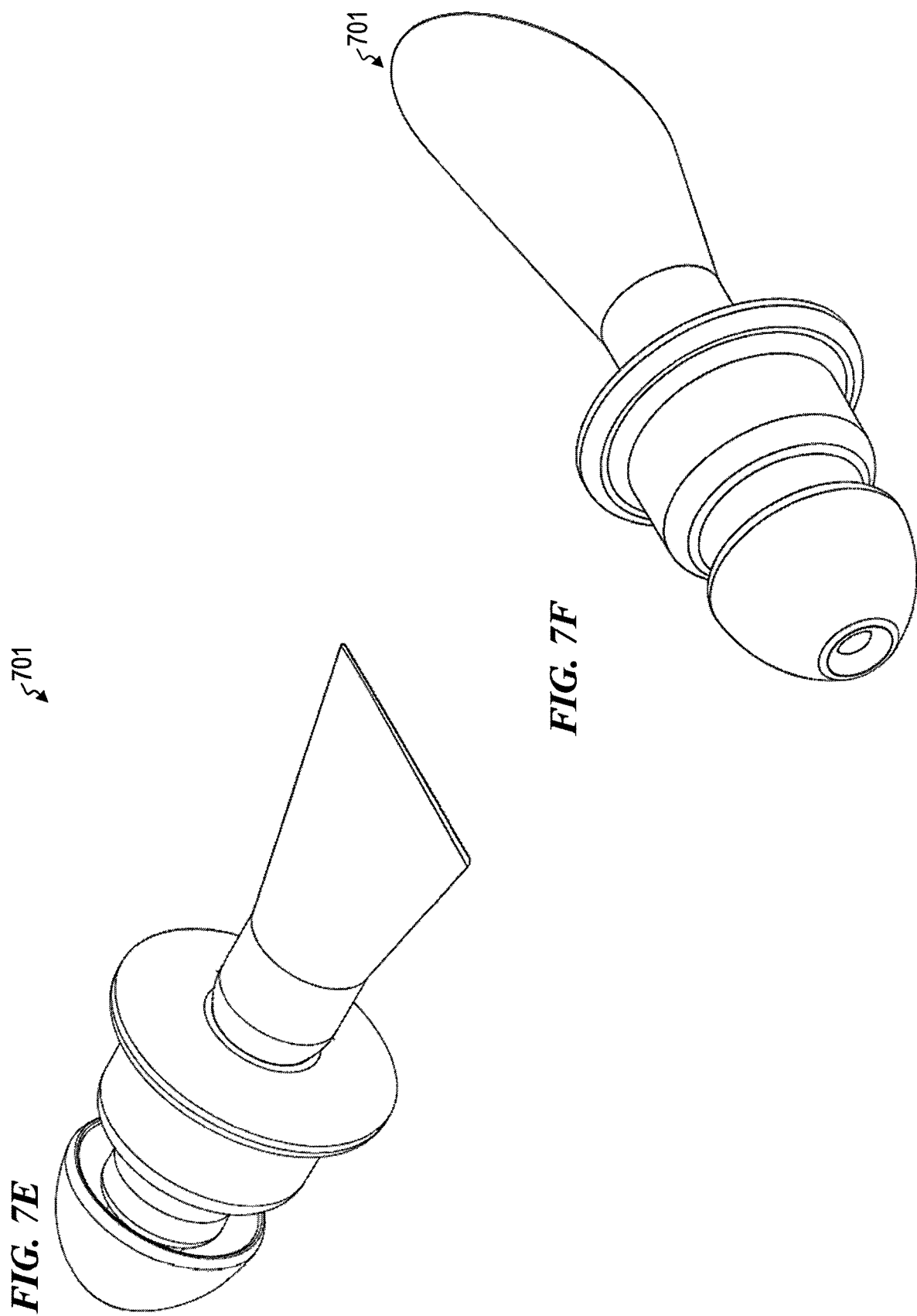

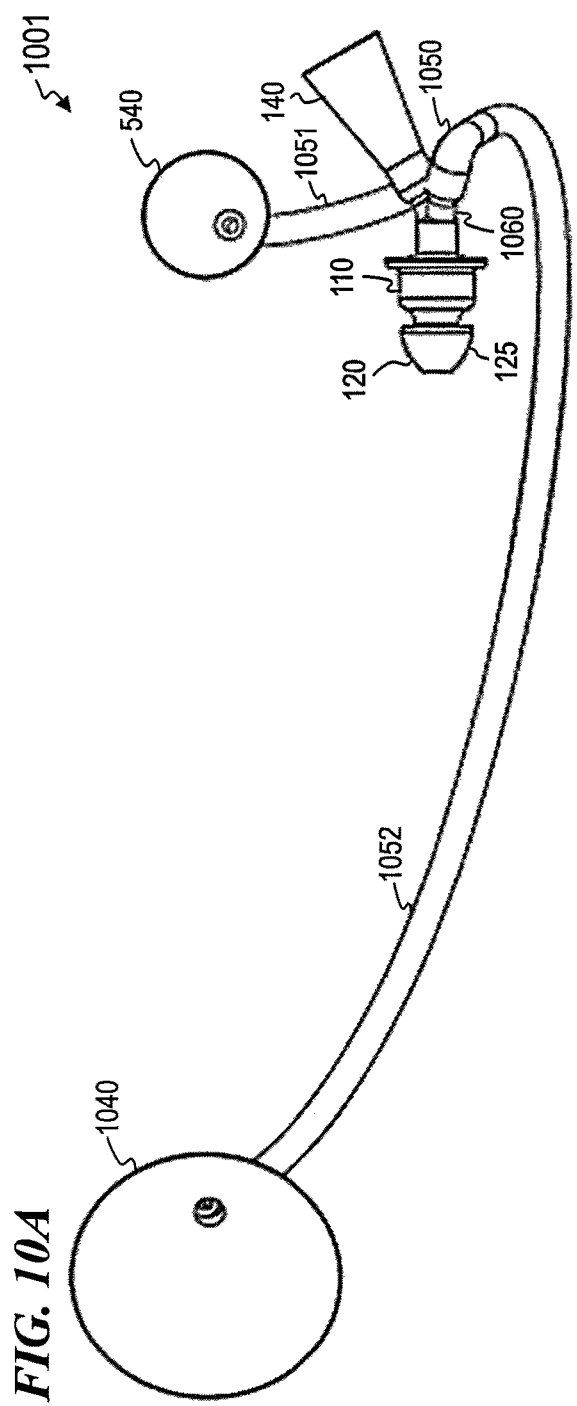
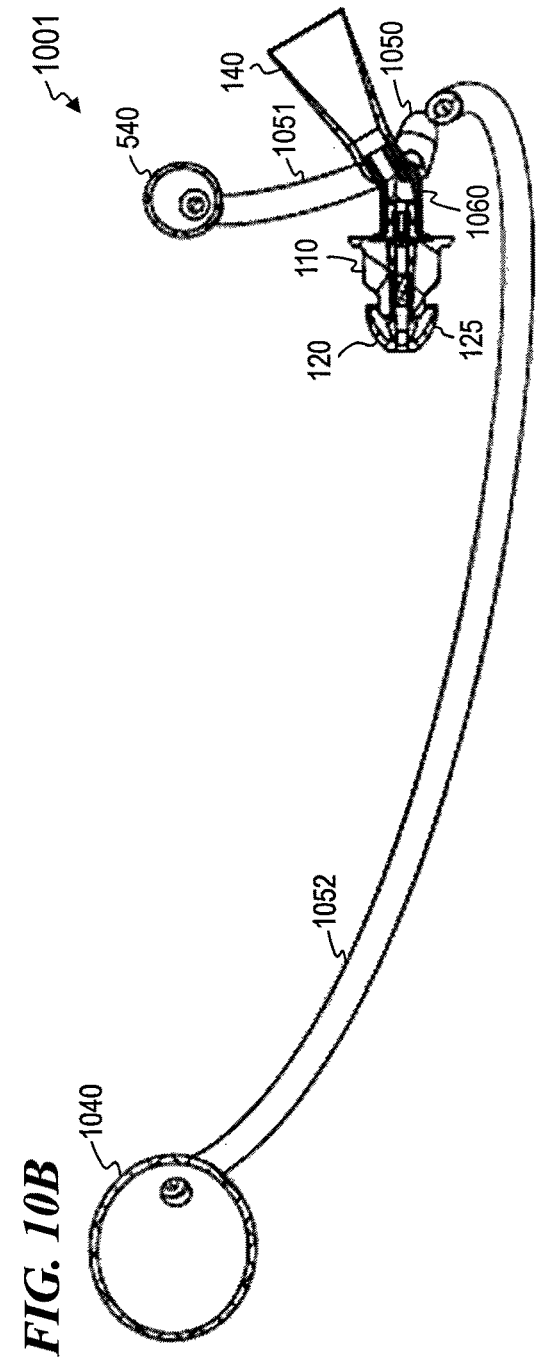

TUNED-FREQUENCY-SPECTRUM EARPIECE

CROSS-REFERENCE TO RELATED APPLICATIONS

This application claims priority benefit, under 35 U.S.C. § 119(e), of U.S. Provisional Patent Application 63/409,408, filed Sep. 23, 2022 by David M. Chenal, titled "Tuned-frequency-spectrum earpiece," which is incorporated herein by reference in its entirety.

This application is related to:

PCT Patent Application No. PCT/US2020/066494, filed Dec. 21, 2020 by JMJ Holdings, LLC, titled "Apparatus and method for an earpiece-foam shaping/sizing tool and container" (published as WO 2021/133747);

PCT Patent Application No. PCT/US2022/014768, filed Feb. 1, 2022 by JMJ Holdings, LLC, titled "Apparatus and method for an earpiece device" (published as WO 2022/169769);

PCT Patent Application No. PCT/US2022/025793, filed Apr. 21, 2022 by JMJ Holdings, LLC, titled "Apparatus and method for an earpiece" (published as WO 2022/226213);

U.S. Design patent application Ser. No. 29/780,178, filed Apr. 22, 2021 by JMJ Holdings, LLC, titled "Earpiece apparatus" (which issued as U.S. Pat. No. D952,831 on May 24, 2022);

U.S. Design patent application Ser. No. 29/769,169, filed Feb. 3, 2021 by JMJ Holdings, LLC, titled "Earpiece device assembly" (which issued as U.S. Pat. No. D964,547 on Sep. 20, 2022);

U.S. patent application Ser. No. 17/785,799 filed Jun. 15, 2022 by JMJ Holdings, LLC, titled "Earpiece-foam sizing apparatus and method" (which issued as U.S. Pat. No. 11,826,231 on Nov. 28, 2023); and U.S. patent application Ser. No. 15/130,417, filed Apr. 15, 2016 by JMJ Holdings, LLC, titled "Sound attenuation" (which issued as U.S. Pat. No. 9,603,746 on Mar. 28, 2017);

each of which is incorporated herein by reference in its entirety.

FIELD OF THE INVENTION

The present invention relates to devices and methods for earpieces, and in particular to a system and method for ear protectors configured to selectively tune the audible-frequency spectrum of audio passed to the eardrum of the user to improve speech recognition while substantially reducing the intensity of impulse sounds, such as from gunshots and explosions.

BACKGROUND OF THE INVENTION

U.S. Pat. No. 2,881,759 by Robert W. Hocks et al., issued on Apr. 14, 1959 with the title "Ear protector", and is incorporated herein by reference. U.S. Pat. No. 2,881,759 describes an improved ear protector or plug for controlling communication between the ear drum and the outside of the ear.

U.S. Pat. No. 7,236,605 by Robert J. Oliveira et al. issued on Jun. 26, 2007 with the title "User disposable sleeve for use within the ear canal", and is incorporated herein by reference. U.S. Pat. No. 7,236,605 describes user disposable sleeves for use with sound controlling structures having a non-constant radial profile that can include an inner portion adapted to releasably attach to the sound controlling structure and an outer portion adapted to fit within a user's ear canal. The user disposable sleeve can include holding means configured to releasably secure the sleeve to the elongate sound controlling structure and fitment means configured to conform to an inner surface of an ear. The fitment means can be fixedly disposed over the holding means.

U.S. Pat. No. 7,743,771 by Robert N. Falco issued on Jun. 29, 2010 with the title "Earplug with articulating stem and locking features", and is incorporated herein by reference. U.S. Pat. No. 7,743,771 describes a hearing protection device that includes a stem, a protrusion formed on the stem, an articulation point formed on the stem, and a sound attenuating element including a cavity, where the protrusion is disposed in locking engagement within the cavity to releasably attach the stem to the sound attenuating element, and where the stem is configured to at least partially articulate about the articulation point.

U.S. Pat. No. 8,161,975 by Crest Turdijian issued on Apr. 24, 2012 with the title "Dual mode impulse noise protecting earplug (D-182)", and is incorporated herein by reference. U.S. Pat. No. 8,161,975 describes a two piece dual mode earplug including an integrally molded elongated member having a nose end and an open rear end and a channel extending through. An integrally molded insert member is formed with a base portion and a rod portion and with the rod portion seated within the open rear end of the elongated member and includes an attenuation filter integrally molded as part of the rod portion and includes first and second openings located on each side of a chamber and with the size and length of the openings together with the chamber providing attenuation of impulse noise. The insert member also includes the base portion integrally molded to have a third opening larger than the first and second openings in the rod portion and with the first, second and third openings together forming a passageway through the insert member to the channel extending through the elongated member.

U.S. Pat. No. 8,327,973 by William Parish et al. issued on Dec. 11, 2012 with the title "Foam compositions with enhanced sound attenuation", and is incorporated herein by reference. U.S. Pat. No. 8,327,973 describes foam compositions with enhanced sound attenuation characteristics for use in earpieces, for example, user-disposable foam members such as foam tips for sound control devices including sound transmission devices and earplugs in which a relationship between the size of the pores and the volume of the cells of the polymeric may be controlled.

U.S. Pat. No. 8,596,279 by Robert N. Falco issued on Dec. 3, 2013 with the title "Offset stem for earplug and earplug formed therewith", and is incorporated herein by reference. U.S. Pat. No. 8,596,279 describes a stem for an earplug and an earplug incorporating the stem where the stem includes an attachment portion configured to receive and retain a sound attenuating element, the attachment portion extending substantially along an attachment axis, and a handle portion extending from the attachment portion substantially along a handle axis, where at least part of the handle axis is non-collinear with respect to the attachment axis.

U.S. Pat. No. 8,960,366 by Justin C. Peskar et al. issued on Feb. 24, 2015 with the title "Foam cushion for headphones", and is incorporated herein by reference. U.S. Pat. No. 8,960,366 describes a composite foam cushion for a sound control device. The cushion includes a core formed of a polymeric foam material and a polymeric coating overlying at least a portion of the core of polymeric foam material. The polymeric coating includes an outer coating layer and an inner polymeric coating layer bonded to the core of polymeric foam material. The inner coating layer may provide the cushion with strength, while providing a high degree of flexibility and suppleness to closely conform around contours and obstructions. The outer coating layer may provide the cushion with enhanced abrasion resistance and/or chemical resistance while having an aesthetically pleasing feel and appearance.

U.S. Pat. No. 9,092,965 by Christopher Thomas Lyons et al. issued on Jul. 28, 2015 with the title "System and method of detecting sleep disorders", and is incorporated herein by reference. U.S. Pat. No. 9,092,965 describes an apparatus for detecting sleep disorders, such as obstructive sleep apnea, includes a housing insertable into an ear canal of a subject. A sensor disposed within the housing measures a position of the subject's head relative to an axis of gravity. A transducer is responsive to the sensor and is capable of creating a stimulus detectable by the subject under certain conditions. In various embodiments, a controller receives signals corresponding to a pitch angle and a roll angle of the subject's head measured by the sensor, determines if the pitch and roll angles correspond to a sleep apnea inducing position, and causes the transducer to generate a stimulus upon determining that the subject's head is in the sleep apnea inducing position more than a predetermined threshold number of times. Various parameters of the stimulus may be modified with successive stimulus generation until a non-sleep apnea inducing position is detected.

U.S. Pat. No. 9,603,746 by David M. Chenal issued on Mar. 28, 2017 with the title "Sound attenuation", and is incorporated herein by reference. U.S. Pat. No. 9,603,746 describes a sound attenuation system that can include a first end that can include a shaft and a flange, the flange can be coupled to the shaft, and a second end that can include a filter stem and a cap. The filter stem can have a hole. The cap can have a first position in which the cap occludes the hole and can have a second position in which the cap is clear of the hole.

U.S. Pat. No. 10,440,459 by Richard C. Smith et al. issued on Oct. 8, 2019 with the title "Ergonomic earpiece", and is incorporated herein by reference. U.S. Pat. No. 10,440,459 describes a cable assembly for electronic devices such as cellular telephones and music devices. The cable assembly can comprise either one or two earpieces, each of which is configured to be received into the concha of a user's ear. The earpiece(s) can be configured so as to be held in place by at least one anatomical structure of the concha. A speaker can be in acoustic communication with each earpiece. A cable can be configured to communicate a signal representative of sound from the electronic device to each earpiece. A microphone can be permanently attached or removably attachable to the cable to facilitate use with a cellular telephone. The cable assembly can facilitate hands free operation of a cellular telephone and can facilitate listening to a music device. Other implementations and related methods are also disclosed.

SUMMARY OF THE INVENTION

In some embodiments, the present invention provides a tuned-frequency-spectrum earpiece for selectively tuning audio frequencies that enter an inner ear of a user wearing the earpiece, the earpiece including a base having an emitter end and a receiver end, wherein the base includes a channel that passes through an entirety of the base; a sound-attenuation plug, wherein the sound-attenuation plug is configured to couple to the base such that the sound-attenuation plug surrounds at least a portion of the channel of the base; a first filter device configured to insert into the channel of the base and configured to selectively reject undesired frequencies of the audio frequencies that enter the earpiece; and a frequency-spectrum-shaping sound-collection horn operatively coupled to the receiver end of the base and configured to selectively increase a relative amount of desired frequencies of the audio frequencies that enter the inner ear of the user via the first filter device. As used herein, "selectively tuning" by the earpiece means selectively enhancing certain frequencies of the audio spectrum (i.e., increasing the audio volume or sound intensity of those portions of the audio spectrum delivered to the eardrum of the human user) and/or selectively rejecting other certain frequencies of the audio spectrum (i.e., decreasing the audio volume or sound intensity of those other portions of the audio spectrum delivered to the eardrum of the human user and/or decreasing the impulse energy of audio delivered to the eardrum, e.g., from gunshots).

In some embodiments, the earpiece selectively tunes the frequency-spectrum response and impulse response of audio passed to the eardrum of the user to improve speech recognition while substantially reducing the intensity of impulse sounds, such as from gunshots and explosions.

In some embodiments, a plurality of sound-collection horns are coupled to each deliver sound into the base of the tuned-frequency-spectrum earpiece.

BRIEF DESCRIPTION OF THE FIGURES

FIG. 2A is a side-view diagram of a tuned-frequency-spectrum earpiece 201, according to some embodiments of the present invention.

FIG. 6E is a first perspective-view diagram of tuned-frequency-spectrum earpiece 601, according to some embodiments of the present invention.

FIG. 6F is a second perspective-view diagram of tuned-frequency-spectrum earpiece 601, according to some embodiments of the present invention.

FIG. 7E is a first perspective-view diagram of tuned-frequency-spectrum earpiece 701, according to some embodiments of the present invention.

FIG. 7F is a second perspective-view diagram of tuned-frequency-spectrum earpiece 701, according to some embodiments of the present invention.

FIG. 10A is a side-view diagram of a tuned-frequency-spectrum earpiece 1001, according to some embodiments of the present invention.

FIG. 10B is a cross-section view of tuned-frequency-spectrum earpiece 1001, according to some embodiments of the present invention.

DETAILED DESCRIPTION OF THE INVENTION

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

Figure 1A:
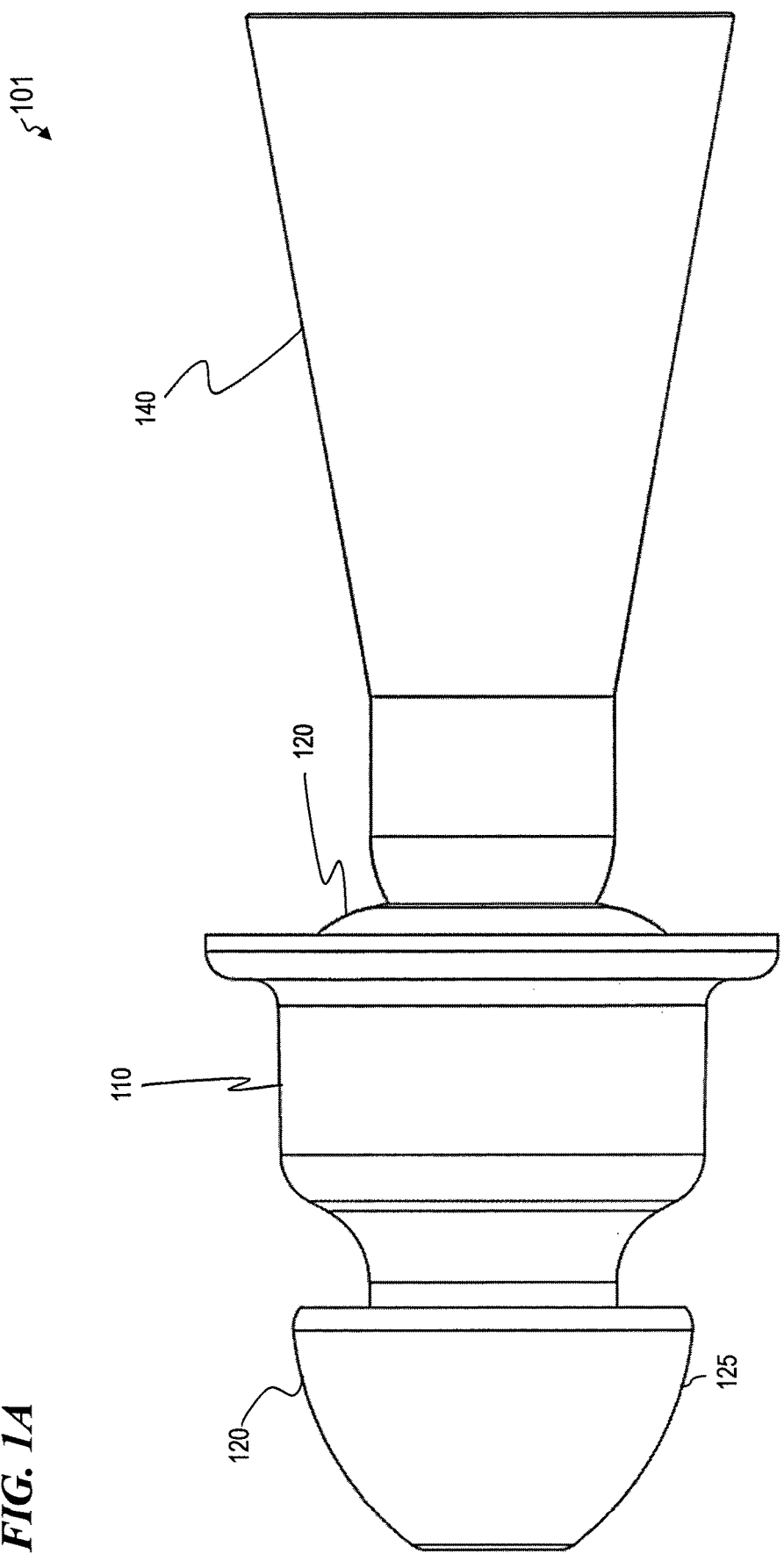
FIG. 1A is a first side-view diagram of a tuned-frequency-spectrum earpiece 101, according to some embodiments of the present invention.

FIG. 1A is a first side-view diagram of a tuned-frequency-spectrum earpiece 101, according to some embodiments of the present invention. In some embodiments, earpiece 101 includes a sound-attenuating element (also called a "plug") 110 (in some embodiments, a foam sound-attenuating element 110), a pliable, sound-attenuating base 120, a filter system 130 (not visible in FIG. 1A; see FIG. 1B), and a frequency-selective sound collector 140 (also referred to herein as a horn or funnel or frequency collector). In some embodiments, earpiece 101 is similar to earpiece 1701 of FIG. 17A in PCT application publication WO 2022/226213 (incorporated by reference above), except that earpiece 101 further includes components 130 and 140 in order to provide the tuned-frequency-spectrum functionality of the present invention. As used herein, "audio frequencies" refer to frequencies of sound detectable by a mammal such as a human. In some embodiments, filter system 130 functions as the audio-frequency equivalent of an electronic band-pass filter (e.g., one that exhibits first-order, second-order or higher-order low-pass filtering to block high frequency components of sound impulses (such as from explosions or gunfire) combined with selective first-order, second-order or higher-order high-pass filtering that blocks low-frequency rumble such as from a military tank or industrial air compressors) that selectively passes frequencies within a certain range (such as frequencies needed to understand human speech) and rejects frequencies outside that range. In some such embodiments, for example, filter system 130 rejects selected low audio frequencies (e.g., audio frequencies associated with engine rumbling, low bass at a rock concert, etc.) and rejects selected high audio frequencies (e.g., frequencies associated with loud, sudden-impact or impulse noises such as an explosion from a gun or bomb), while passing most other audio frequencies, and in particular speech frequencies, for some embodiments. In some embodiments, filter system 130 reduces the amplitude of audio frequencies associated with loud, sudden-impact (impulse) noises by absorbing the abrupt change in air pressure caused by the sudden-impact noises.

In some embodiments, horn 140 increases the amounts of desired audio frequencies (e.g., relatively higher-audio-frequency audio associated with a speaking or singing voice and/or music) that reach filter system 130. In some such embodiments, horn 140 combines with system 130 and earpiece 101 as a whole to provide the tuned-frequency-spectrum functionality of earpiece 101. In some embodiments, the tune-frequency-spectrum functionality of earpiece 101 allows the user of earpiece 101 to block out unwanted sounds and provide protection for the user's ear while still hearing desired sounds. Accordingly, in some embodiments, earpiece 101 is used in environments that have unwanted loud or low-frequency background noise and/or loud, sudden-impact noises, but also have higher frequency talking/singing/music that is desired to be heard (e.g., at a rock concert, a football stadium, inside a tank or other large, noisy vehicle, etc.). In some embodiments, the desired audio frequencies that are amplified by horn 140 include lower audio frequencies (like frequencies down to 20 Hz), which, in some embodiments, are used to provide therapeutic or healing characteristics.

Figure 1B:
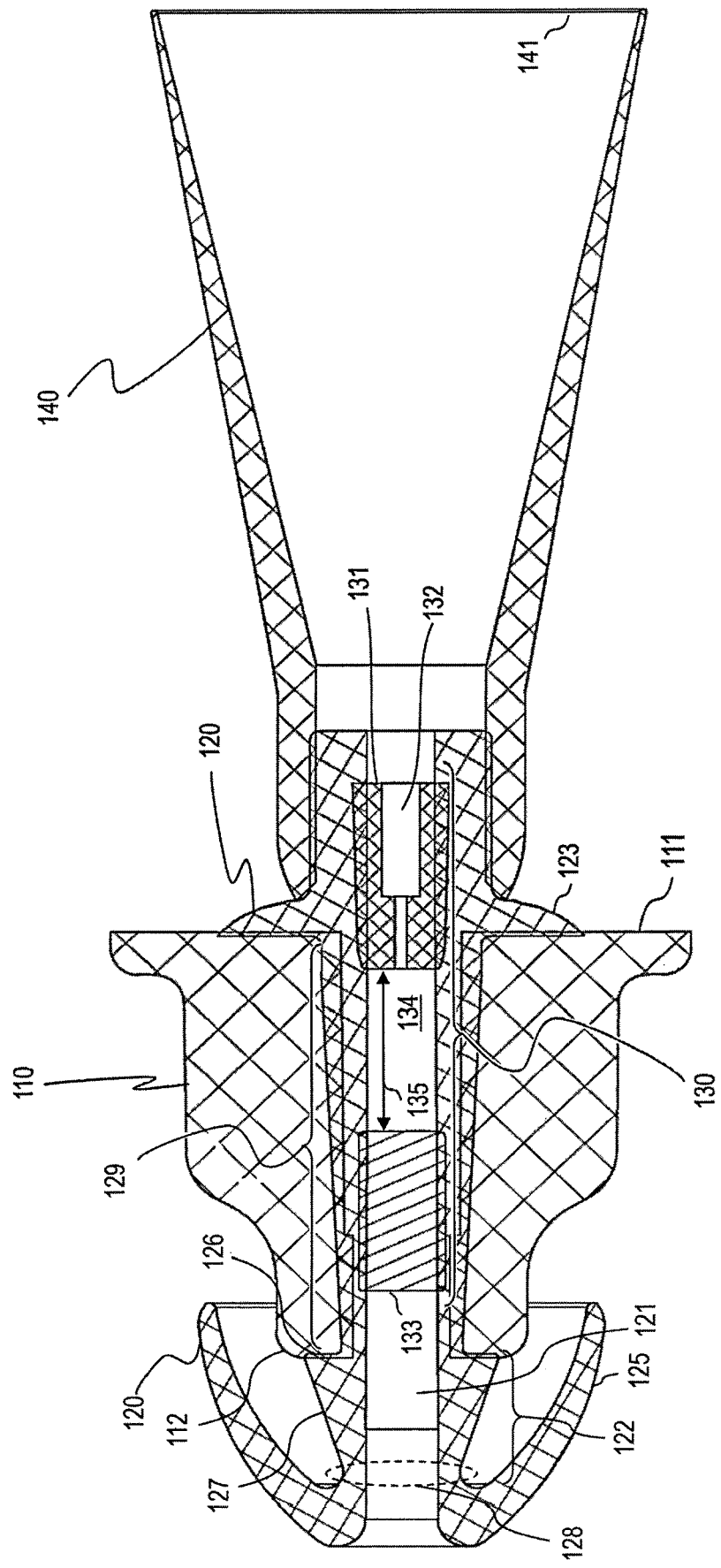
FIG. 1B is a cross-section view of tuned-frequency-spectrum earpiece 101, according to some embodiments of the present invention.

FIG. 1B is a cross-section view of tuned-frequency-spectrum earpiece 101, according to some embodiments of the present invention. Some components shown in the cross-section view of FIG. 1B (and some components in the cross-section views of FIGS. 1C, 2B, 3B, 4B, 5B, 6B, 7B, 8B, 9B, and 10B) have overlap with each other at the boundaries between the components (see, for example, the overlap between the boundaries of sound-attenuating element 110 and stem 129 of base 120). The component overlap shown in the cross-section views is due to the fact that certain pliable components (e.g., the sound-attenuating element 110, the frequency-selective sound collector 140, the first filter device 131, and the second filter device 133) are shown in their "as-molded" or "as-made" sizes in the cross-section views rather than in their modified sizes that occur when the earpieces are actually assembled. For example, when sound-attenuating element 110 is placed over stem 129 of base 120, the interior channel of sound-attenuating element 110 is expanded (is temporarily stretched) from the size shown in FIG. 1B to a larger size (not shown) that allows the base to be inserted through the interior channel of sound-attenuating element 110 and then reduces in size (shrinks towards its smaller diameter) to fit snugly against the outside wall of the central stem 129 of base 120. In some embodiments, one or more of each frequency-selective sound collector (each also optionally called a sound-collection horn or funnel) described herein (such as frequency-selective sound collector 140) is also, or is primarily, a direction-selective sound collector 140 that is pointed and/or oriented to increase the amount of sound and/or certain selected frequencies of the audio spectrum of sound from certain selected direction(s) while reducing the amounts and/or other certain selected frequencies of sound from other directions. In some other embodiments, one or more of each sound collector (each also optionally called a sound-collection horn or funnel) described herein (such as frequency-selective sound collector 140) is primarily a direction-selective sound collector that is pointed and/or oriented to increase the amount of sound from certain selected direction(s) while reducing the amount of sound from other directions. This can help the user in a loud concert selectively collect relatively more sound from the person's side (e.g., from neighboring concert fans) in order to have conversations with those next to the user while collecting relatively less of the heavily amplified sound from the concert stage. Other environments that could benefit from similar selective directionality for sound reception could be football games or gun ranges or military/artillery battlefields.

In some embodiments, base 120 includes a channel 121 that passes through base 120 (including stem 129). In some embodiments, base 120 includes a plug-stop 122 having a flat proximal surface 126 and a tapered section 127. In some embodiments, earpiece 101 is assembled by stretching and forcing sound-attenuating element 110 over the end of pliable distal flange 125 and into position around stem 129, wherein top surface 111 of sound-attenuating element 110 is compressed against flat interior surface of flange 123, and bottom flat surface 112 of sound-attenuating element 110 is compressed against flat proximal surface 126 of plug-stop 122. In some embodiments, sound-attenuating element 110 keeps the stem 129 of base 120 from buckling, and also absorbs and attenuates sound that otherwise is somewhat conducted through the length of base 120. The numerous material discontinuities and spacings between base 120 and sound-attenuating element 110 also further help to attenuate sound. In some embodiments, sound-attenuating element 110 is made of a visco-elastic foam (also called memory form) that, once temporarily compressed slowly restores (e.g., over a period of about 5 seconds to about 30 seconds) toward a default fully expanded shape or toward a shape that conforms gently to the shape of the user's ear canal.

Figure 1C:
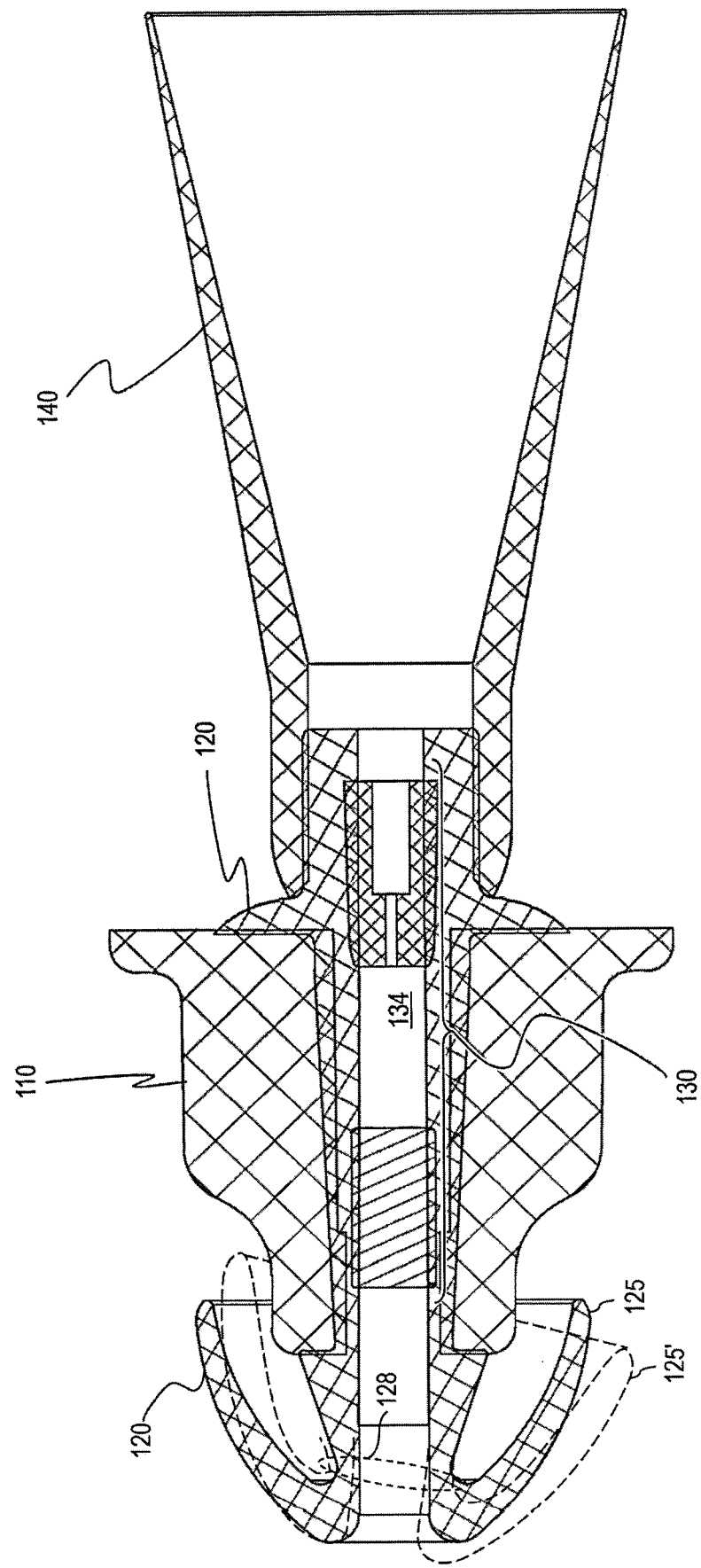
FIG. 1C is a cross-section view of tuned-frequency-spectrum earpiece 101 (labeled in FIG. 1C as 101'), according to some embodiments of the present invention.

In some embodiments, distal flange 125 is attached to the distal end of tapered section 127 at a flexible joint region 128, and therefore distal flange 125 may easily bend such that one side of the inner surface of distal flange 125 is much nearer to, or touching, tapered section 127 or nearer to, or touching, sound-attenuating element 110 in the assembled earpiece 101. In some embodiments, the external lateral surface of tapered section 127 is shaped like the frustrum of a cone. In some embodiments, tapered section 127 is shaped to vary its stiffness from a more-stiff stiffness value at stop 126 to a less-stiff stiffness value at flexible joint region 128, in order to reduce a tendency of tapered portion 127 to collapse or bend sideways along its length, yet still allow easier bending of the distal flange 125 relative to tapered portion 127 at bending location 128 at the distal end of tapered portion 127 to allow a variable angle (as shown in FIG. 1C) of the pliable distal flange 125 relative to the internal-to-the-ear axis of stem 129.

In some embodiments, filter system 130 includes a first filter device 131 and a second filter device 133. In some embodiments (not shown), filter system 130 includes only first filter device 131. In some embodiments (not shown), filter system 130 includes only second filter device 133. In some embodiments, first filter device 131 is a Hocks Noise Filter™ such as provided by Hocks Hearing Healthcare Products (www.hocksproducts.com/hocks_noise_filter). In some embodiments, first filter device 131 is similar to the body portion 10 of FIG. 1 in U.S. Pat. No. 2,881,759 (incorporated by reference above), except that the shape of first filter device 131 is made to fit inside channel 121 of base 120 instead of fitting the ear of a user directly. In some embodiments, first filter device 131 includes a channel 132 that passes through first filter device 131 (in other embodiments (not shown), first filter device 131 does not include a channel). In some embodiments, channel 132 includes two portions, a first portion with a first larger diameter, and a second portion with a second smaller diameter. In some embodiments, the narrowness of channel 132 of first filter device 131 limits the amount of air that can get into and past first filter device 131, which therefore reduces the magnitude of incoming pulses of sound. In some embodiments, first filter device 131 is configured to eliminate or reduce high frequencies associated with loud, sudden impact noises. In some embodiments, first filter device 131 is made from a polypropylene; in some embodiments, first filter device 131 is made from a foam; in some embodiments, first filter device 131 is made from any other suitable material for absorbing selected audio frequencies and/or reducing the amplitude of incoming audio frequencies. In some embodiments, second filter device 133 is configured to reduce resonance in earpiece 101 caused by incoming audio frequencies. In some embodiments, second filter device 133 is made from, or includes, cotton. In some embodiments, second filter device 133 is made from, or includes, a visco-elastic memory foam such as described for sound-attenuating element 110. In some embodiments, second filter device 133 is made from, or includes, urethane. In some embodiments, second filter device 133 is made from, or includes, urethane foam. In some embodiments, second filter device 133 is made from, or includes, any suitable polymer foam having open cells and/or closed cells (e.g., in some embodiments, second filter device 133 includes an open-cell or closed-cell polyurethane foam). In some embodiments, second filter device 133 is made from any other suitable material capable of reducing resonance in earpiece 101. In some embodiments, first filter device 131 and/or second filter device 133 is integrated with base 120 such that base 120 and filter system 130 are made as a single, fully integrated component (e.g., in some embodiments, base 120 and first filter device 131 are made from a single mold that forms first filter device 131 within channel 121 of base 120 as a single piece).

In some embodiments (not shown), second filter device 133 includes a channel or opening there through (in some such embodiments, the channel improves the ability of second filter device 133 to allow changes in air pressure to pass through second filter device 133 such as encountered when flying in a commercial or military aircraft). In some embodiments, second filter device 133 is separated from first filter device 131 by an air gap 134 having a length 135 and a cross-sectional area equal to the cross section of channel 121. In some embodiments, the configuration of first filter device 131, air gap 134, and second filter device 133 forms the audio-frequency equivalent of an electronic two-stage low-pass filter that absorbs high frequencies and passes at least some low frequencies. In some embodiments (not shown), the sequential order of first filter device 131 and second filter device 133 is reversed such that second filter device 133 is closer to horn 140 than first filter device 131, but in such embodiments, air gap 134 remains between second filter device 133 and first filter device 131.

In some embodiments, the shape and/or dimensions of frequency-selective sound collector 140 are varied to selectively increase the amount of desired audio frequencies that enter earpiece 101. For example, in some embodiments, the length of frequency-selective sound collector 140 is modified (compare, for example, frequency-selective sound collector 140 to frequency-selective sound collector 440 of FIG. 4A); in some embodiments, the circumference of the cone at the input end 141 of frequency-selective sound collector 140 is modified (compare, for example, frequency-selective sound collector 140 to frequency-selective sound collector 540 of FIG. 5A); in some embodiments, the angle of input end 141 relative to the longitudinal axis of channel 121 (and/or relative to the longitudinal axis of horn 140 itself) is modified. In some embodiments, as shown in FIG. 1B, a plane surface of input end 141 is at a 90-degree angle relative to the longitudinal axis of channel 121, while in other embodiments, the plane surface of input end 141 is at a different angle relative to the longitudinal axis of channel 121 such as 135 degrees, 145 degrees, 155 degrees, 165 degrees, or the like (see, for example, FIGS. 7A-7F). In some embodiments, frequency-selective sound collector 140 is made from a cured plastisol (e.g., a PVC). In some embodiments, frequency-selective sound collector 140 is injection molded and is made from a suitable plastic polymer. In some embodiments, frequency-selective sound collector 140 is made from any other suitable material. In some embodiments, the distal end (left-hand portion in FIG. 1B) of frequency-selective sound collector 140 stretches over the proximal end (right-hand portion) of base 120 and/or the proximal end of base 120 is compressed to insert into the distal end of frequency-selective sound collector 140, to provide a snug fit.

FIG. 1C is a cross-section view of tuned-frequency-spectrum earpiece 101 (labeled in FIG. 1C as 101'), according to some embodiments of the present invention. As shown in FIG. 1C, earpiece 101 is labeled as 101' because distal flange 125 is also shown with dashed-line alternative bent position 125' that includes pliable sound-attenuating base 120, sound-attenuating element 110, filter system 130, and frequency-selective sound collector 140. FIG. 1C shows sound-attenuating pliable distal flange in its default position labeled 125, and in dashed-line outline of a bent position, labeled 125'. Bent position 125' (i.e., the angle of cup 125) is determined by the individual shape of the ear canal of the user wearing earpiece.

Figure 1D:
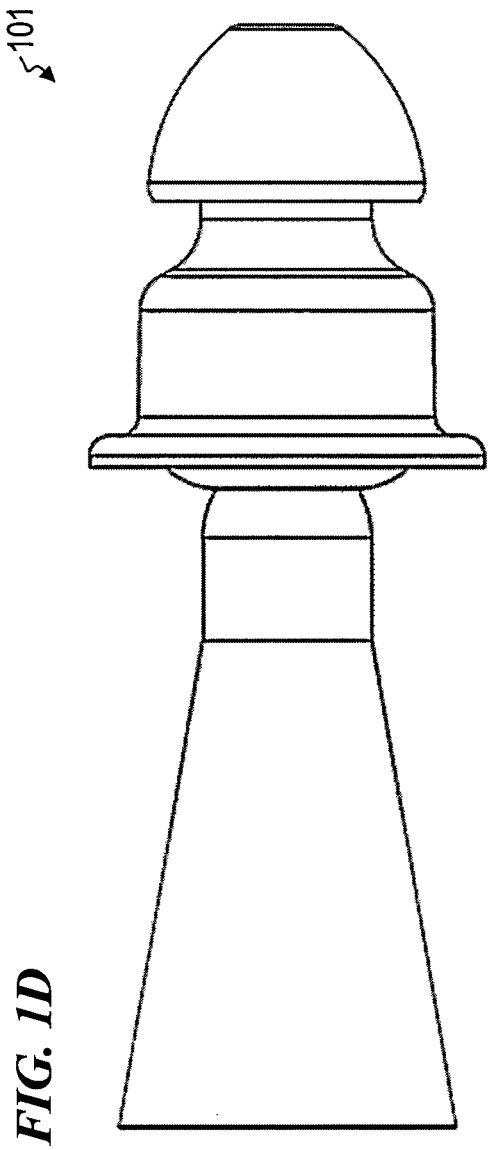
FIG. 1D is a second side-view diagram of tuned-frequency-spectrum earpiece 101, according to some embodiments of the present invention.

FIG. 1D is a second side-view diagram of tuned-frequency-spectrum earpiece 101, according to some embodiments of the present invention.

Figure 1F:
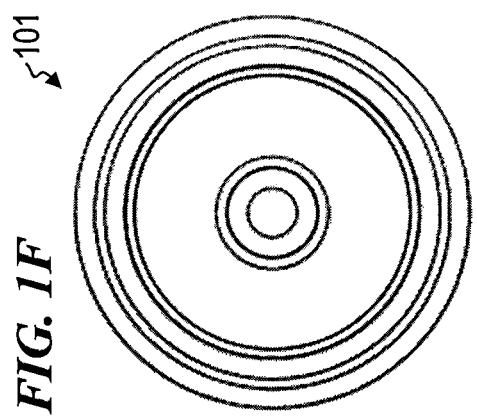
FIG. 1F is a second end-view diagram of tuned-frequency-spectrum earpiece 101, according to some embodiments of the present invention.
Figure 1E:
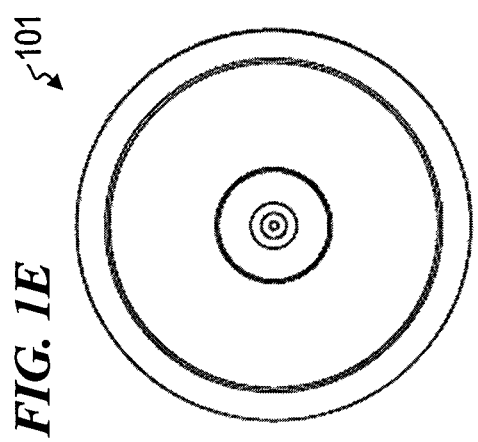
FIG. 1E is a first end-view diagram of tuned-frequency-spectrum earpiece 101, according to some embodiments of the present invention.

FIG. 1E is a first end-view diagram of tuned-frequency-spectrum earpiece 101, according to some embodiments of the present invention. In some embodiments, the first end-view diagram of FIG. 1E shows the view if facing the end of horn 140.

FIG. 1F is a second end-view diagram of tuned-frequency-spectrum earpiece 101, according to some embodiments of the present invention. In some embodiments, the second end-view diagram of FIG. 1F shows the view if facing the end of distal flange 125 of base 120.

Figure 1H:
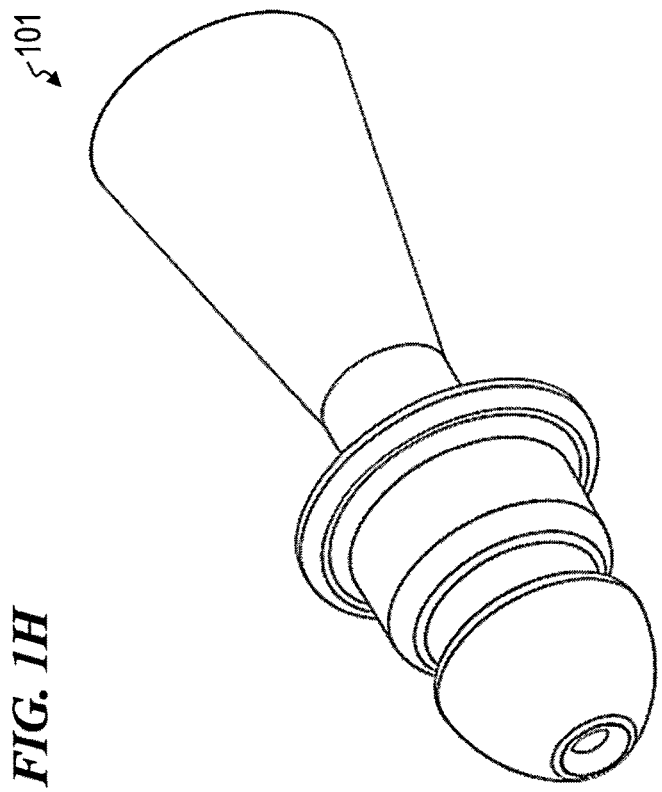
FIG. 1H is a second perspective-view diagram of tuned-frequency-spectrum earpiece 101, according to some embodiments of the present invention.
Figure 1G:
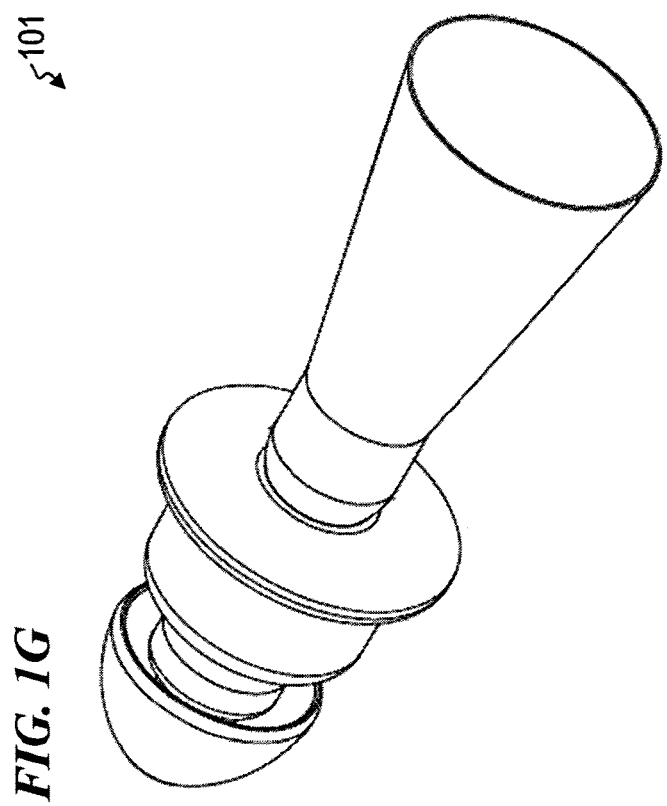
FIG. 1G is a first perspective-view diagram of tuned-frequency-spectrum earpiece 101, according to some embodiments of the present invention.

FIG. 1G is a first perspective-view diagram of tuned-frequency-spectrum earpiece 101, according to some embodiments of the present invention.

FIG. 1H is a second perspective-view diagram of tuned-frequency-spectrum earpiece 101, according to some embodiments of the present invention.

Figure 2B:
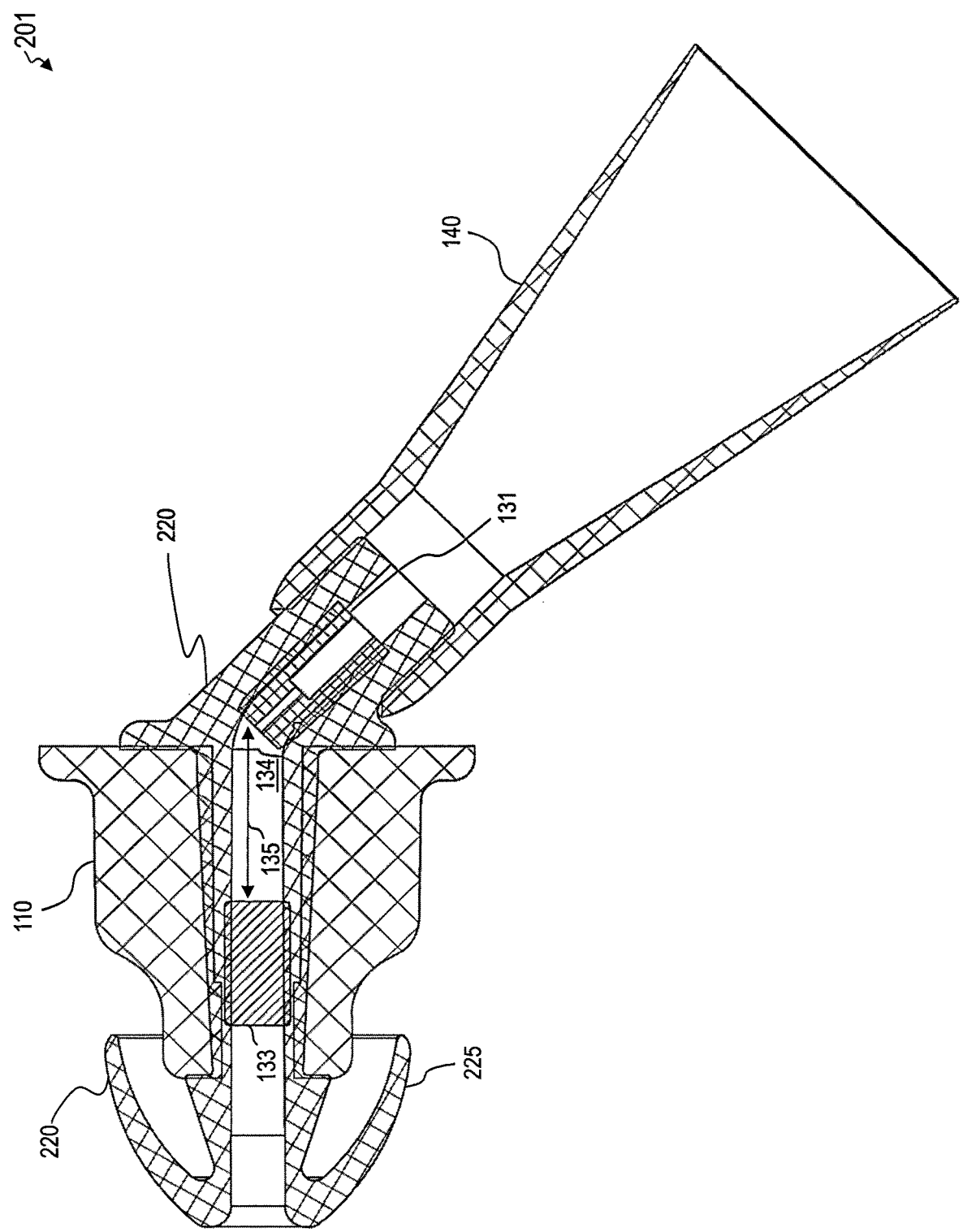
FIG. 2B is a cross-section view of tuned-frequency-spectrum earpiece 201, according to some embodiments of the present invention.

FIG. 2A is a side-view diagram of a tuned-frequency-spectrum earpiece 201, according to some embodiments of the present invention. In some embodiments, earpiece 201 is substantially similar to earpiece 101, except that base 220 and its bendable end cup 225 replaces base 120 and its bendable end cup 125 (filter system 130 is not visible in FIG. 2A; see FIG. 2B).

FIG. 2B is a cross-section view of tuned-frequency-spectrum earpiece 201, according to some embodiments of the present invention. In some embodiments, the central axis of base 220 toward the receiver end of base 220 (i.e., the proximal end of base 220 (the right-hand end in FIG. 2B) that is coupled to frequency-selective sound collector 140), is bent (molded) at an angle relative to the central axis of the remainder of base 220 in order that earpiece 201 fits into the ear canal of the user more comfortably while still having the frequency-selective sound collector 140 extend straight out from, or at some other desired orientation relative to, the side of the head of the user.

Figure 2C:
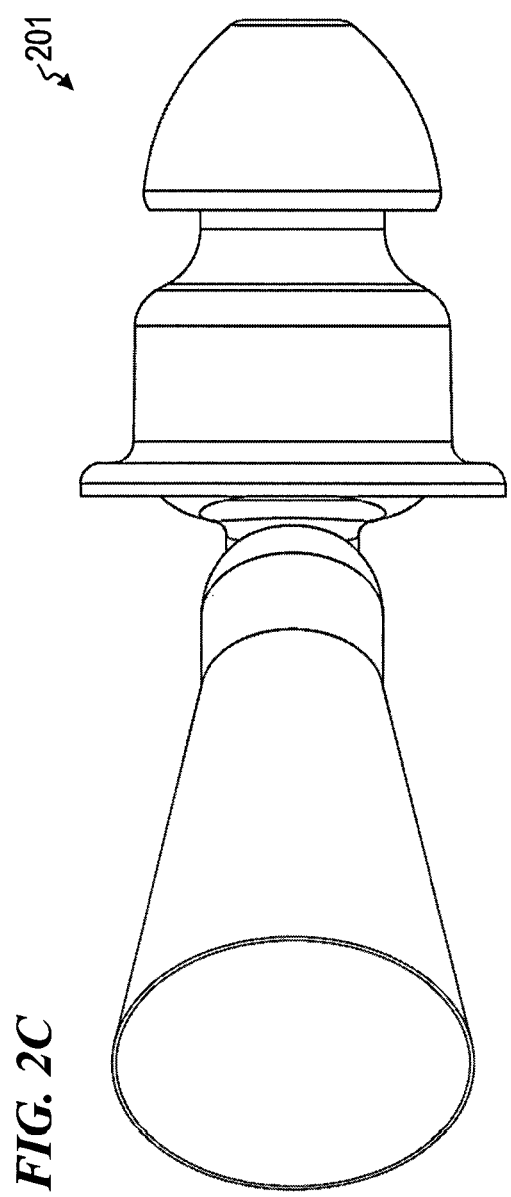
FIG. 2C is a top-view diagram of tuned-frequency-spectrum earpiece 201, according to some embodiments of the present invention.

FIG. 2C is a top-view diagram of tuned-frequency-spectrum earpiece 201, according to some embodiments of the present invention.

Figure 2D:
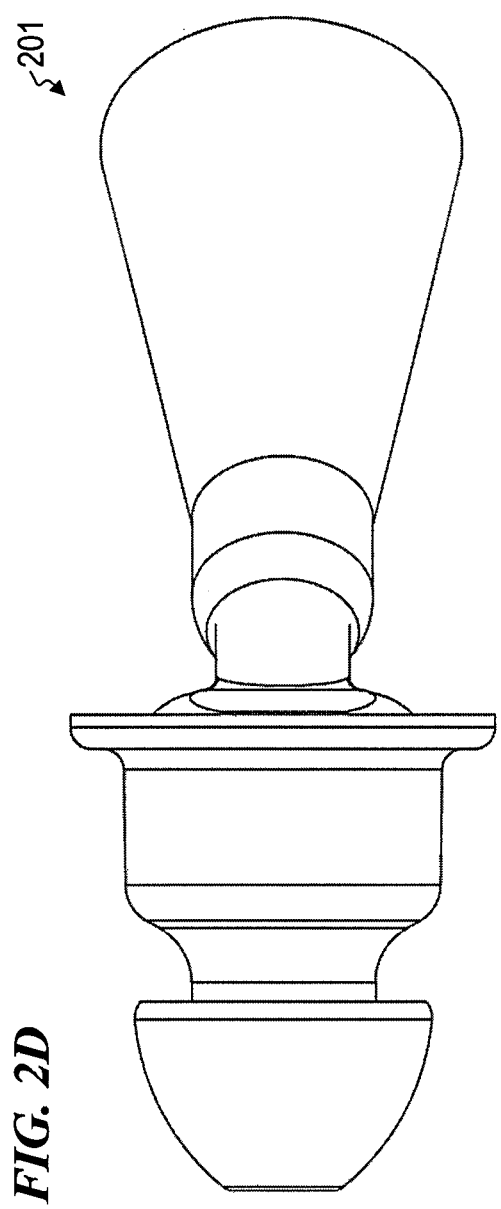
FIG. 2D is a bottom-view diagram of tuned-frequency-spectrum earpiece 201, according to some embodiments of the present invention.

FIG. 2D is a bottom-view diagram of tuned-frequency-spectrum earpiece 201, according to some embodiments of the present invention.

Figure 2F:
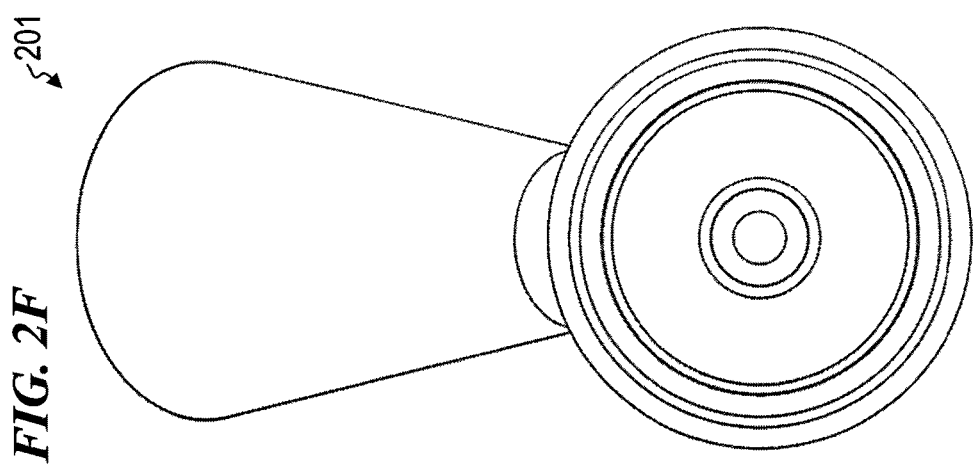
FIG. 2F is a second end-view diagram of tuned-frequency-spectrum earpiece 201, according to some embodiments of the present invention.
Figure 2E:
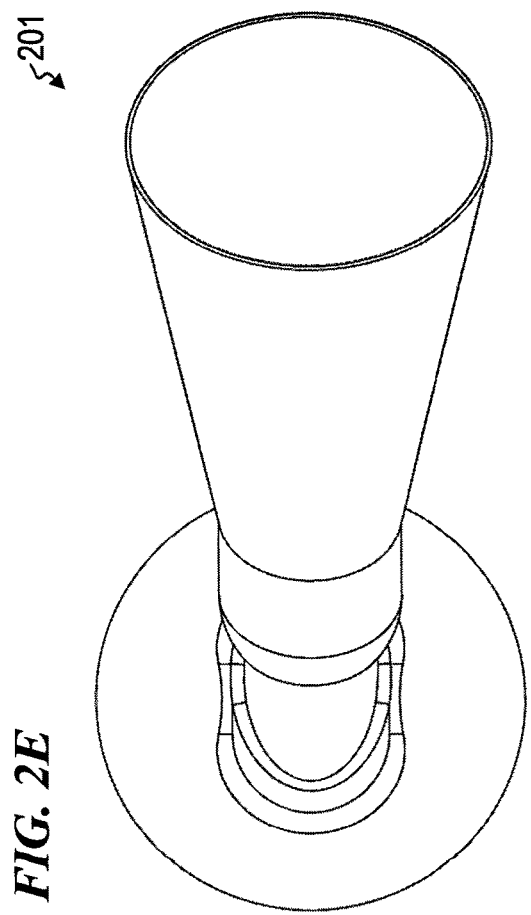
FIG. 2E is a first end-view diagram of tuned-frequency-spectrum earpiece 201, according to some embodiments of the present invention.

FIG. 2E is a first end-view diagram of tuned-frequency-spectrum earpiece 201, according to some embodiments of the present invention. In some embodiments, the first end-view diagram of FIG. 2E shows the view if facing earpiece 201 from the end that includes horn 140.

FIG. 2F is a second end-view diagram of tuned-frequency-spectrum earpiece 201, according to some embodiments of the present invention. In some embodiments, the second end-view diagram of FIG. 2F shows the view if facing the end of distal flange 225 of base 220.

Figure 2H:
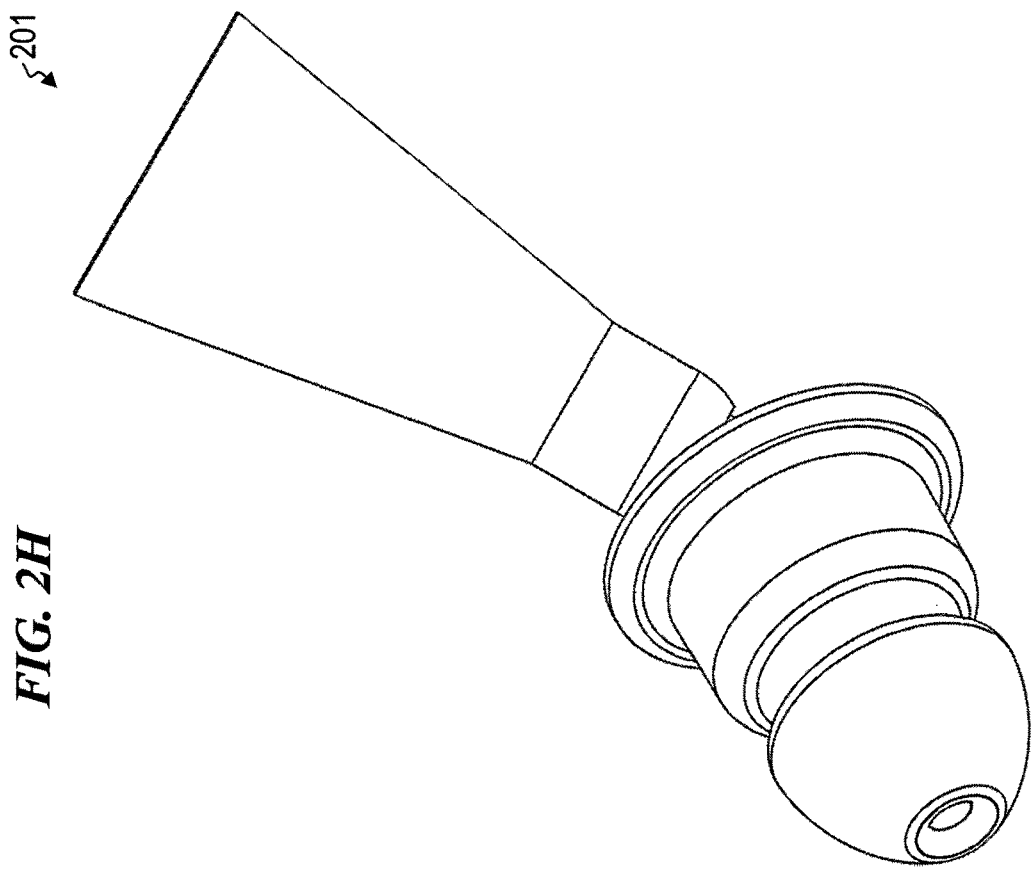
FIG. 2H is a second perspective-view diagram of tuned-frequency-spectrum earpiece 201, according to some embodiments of the present invention.
Figure 2G:
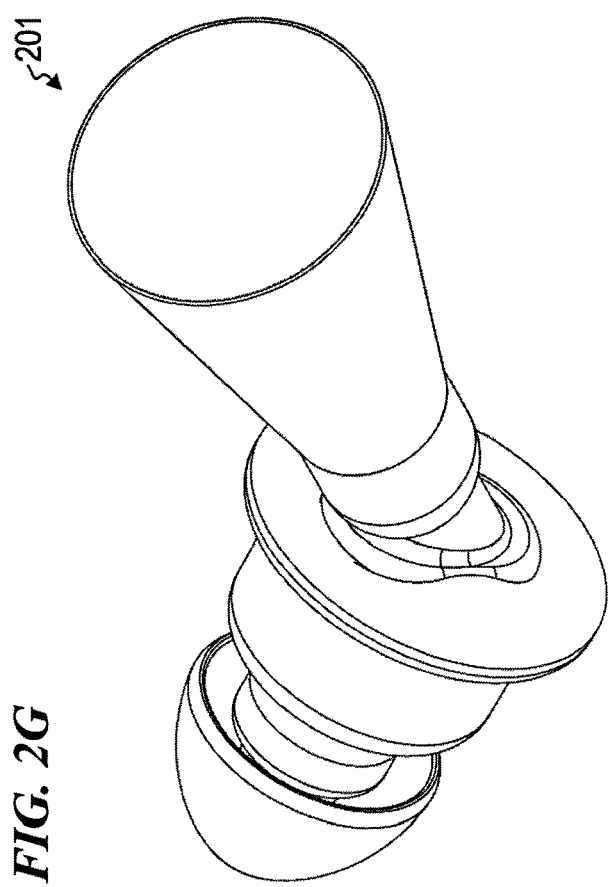
FIG. 2G is a first perspective-view diagram of tuned-frequency-spectrum earpiece 201, according to some embodiments of the present invention.

FIG. 2G is a first perspective-view diagram of tuned-frequency-spectrum earpiece 201, according to some embodiments of the present invention.

FIG. 2H is a second perspective-view diagram of tuned-frequency-spectrum earpiece 201, according to some embodiments of the present invention.

Figure 3A:
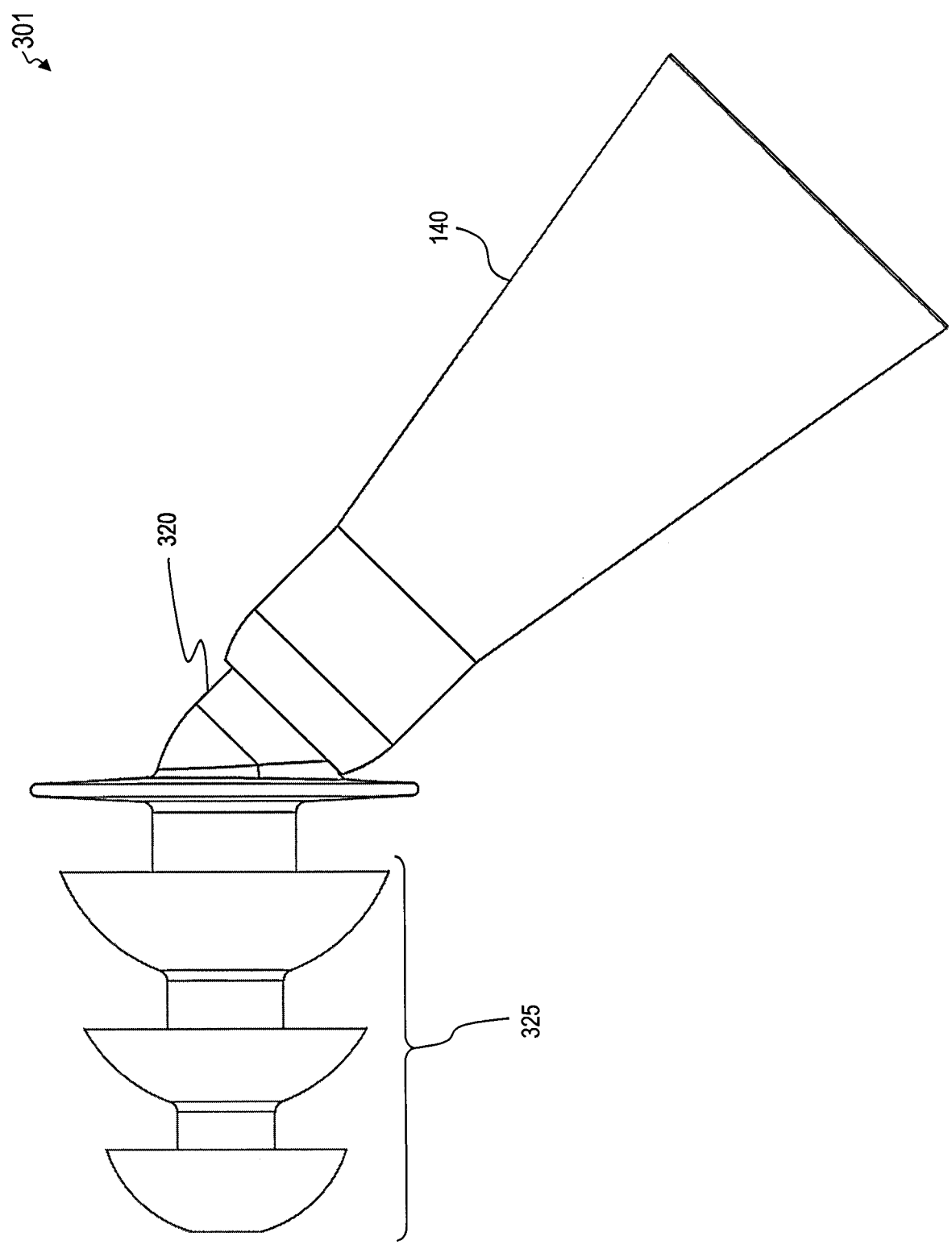
FIG. 3A is a side-view diagram of a tuned-frequency-spectrum earpiece 301, according to some embodiments of the present invention.

FIG. 3A is a side-view diagram of a tuned-frequency-spectrum earpiece 301, according to some embodiments of the present invention. In some embodiments, earpiece 301 is substantially similar to earpiece 201 of FIGS. 2A-2B except that base 220 is replaced with base 320 and sound-attenuating element 110 of FIG. 2B is removed. In some embodiments, base 320 includes a flange system 325 made of a plurality of (e.g., in some embodiments, a series of three) different-sized cup shapes located at the distal (emitter) end of base 320 (in some embodiments, flange system 325 replaces the single, distal flange 225 of FIG. 2B). In some embodiments, each individual cup of flange system 325 includes a convex outer surface and a concave back-side or inner surface, and flange system 325 is made of a polyvinyl chloride (PVC), polymer foam, or any other suitable material.

Figure 3B:
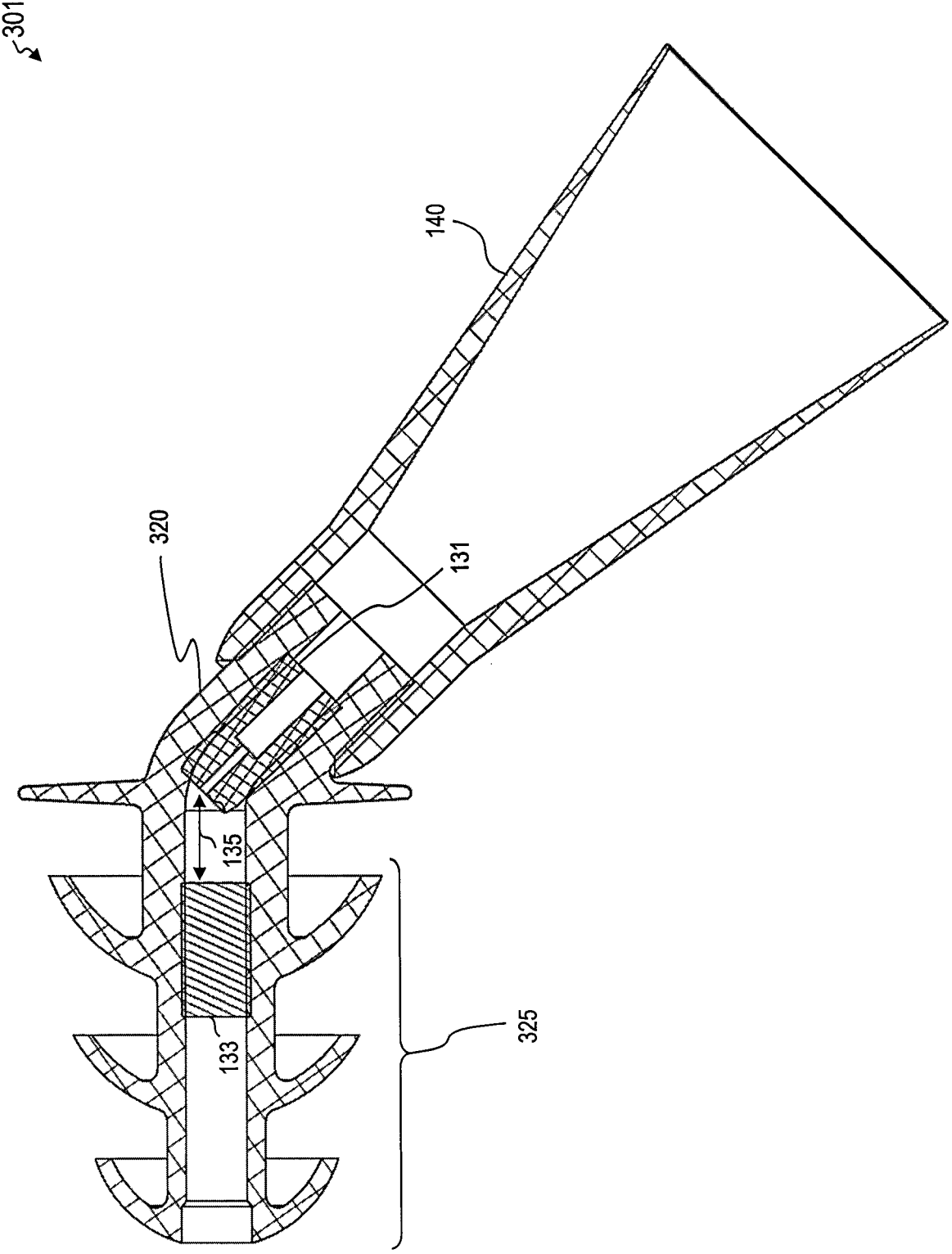
FIG. 3B is a cross-section view of tuned-frequency-spectrum earpiece 301, according to some embodiments of the present invention.

FIG. 3B is a cross-section view of tuned-frequency-spectrum earpiece 301, according to some embodiments of the present invention.

Figure 3C:
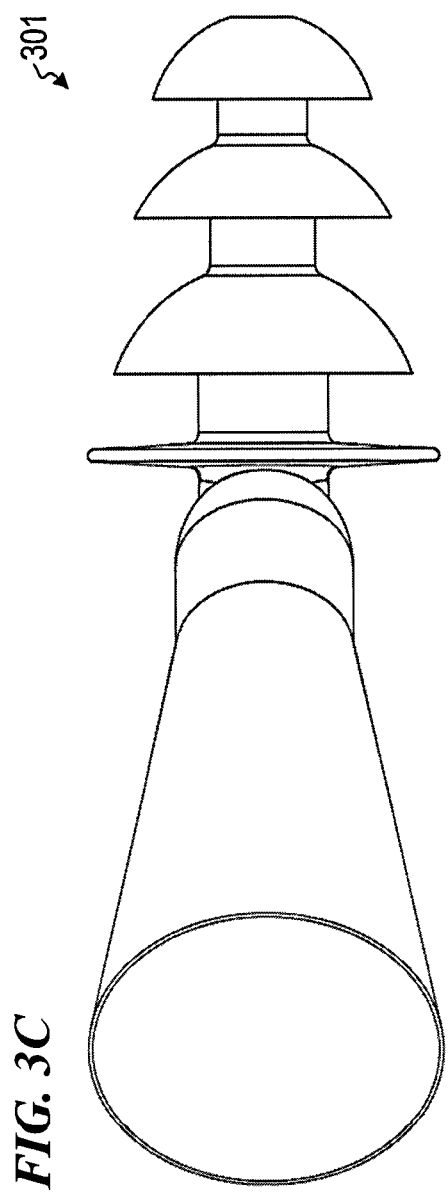
FIG. 3C is a top-view diagram of tuned-frequency-spectrum earpiece 301, according to some embodiments of the present invention.

FIG. 3C is a top-view diagram of tuned-frequency-spectrum earpiece 301, according to some embodiments of the present invention.

Figure 3D:
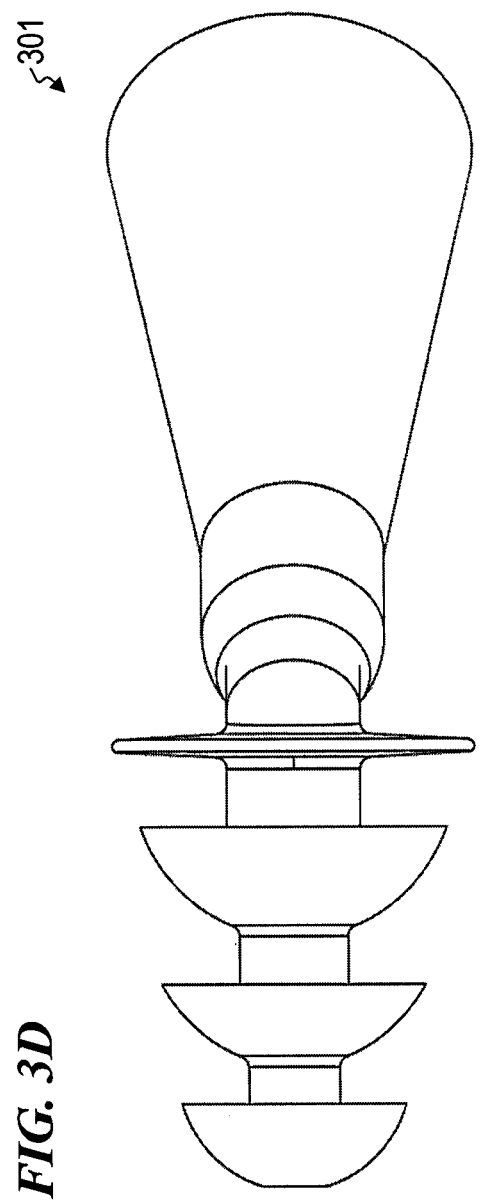
FIG. 3D is a bottom-view diagram of tuned-frequency-spectrum earpiece 301, according to some embodiments of the present invention.

FIG. 3D is a bottom-view diagram of tuned-frequency-spectrum earpiece 301, according to some embodiments of the present invention.

Figure 3F:
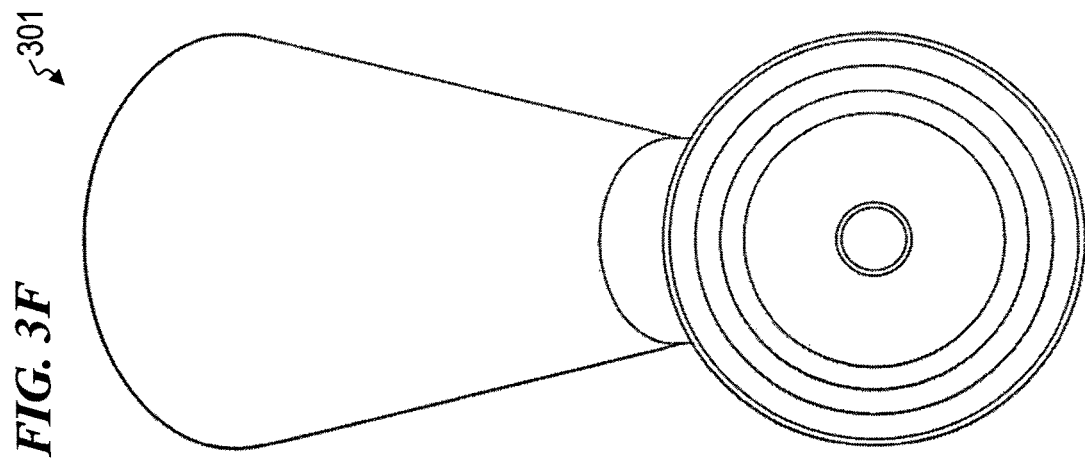
FIG. 3F is a second end-view diagram of tuned-frequency-spectrum earpiece 301, according to some embodiments of the present invention.
Figure 3E:
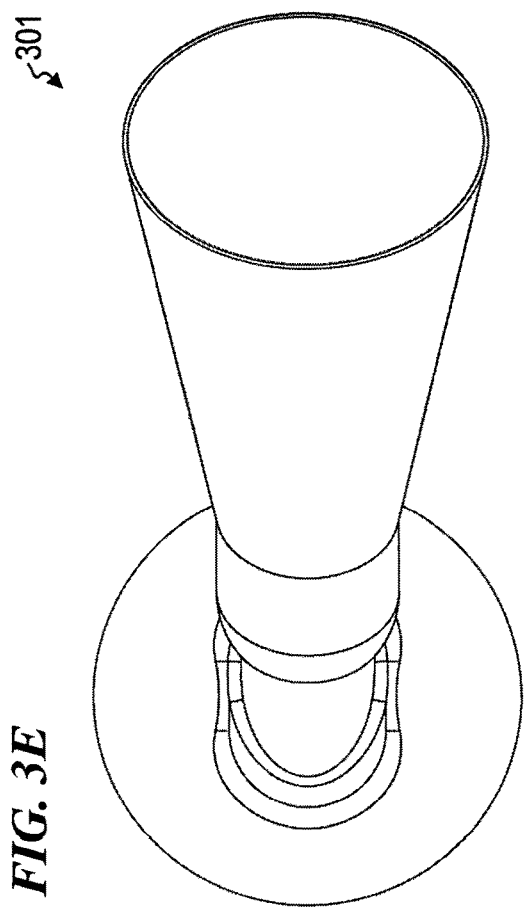
FIG. 3E is a first end-view diagram of tuned-frequency-spectrum earpiece 301, according to some embodiments of the present invention.

FIG. 3E is a first end-view diagram of tuned-frequency-spectrum earpiece 301, according to some embodiments of the present invention. In some embodiments, the first end-view diagram of FIG. 3E shows the view if facing earpiece 301 from the end that includes horn 140.

FIG. 3F is a second end-view diagram of tuned-frequency-spectrum earpiece 301, according to some embodiments of the present invention. In some embodiments, the second end-view diagram of FIG. 3F shows the view if facing the end of flange system 325 of base 320.

Figure 3H:
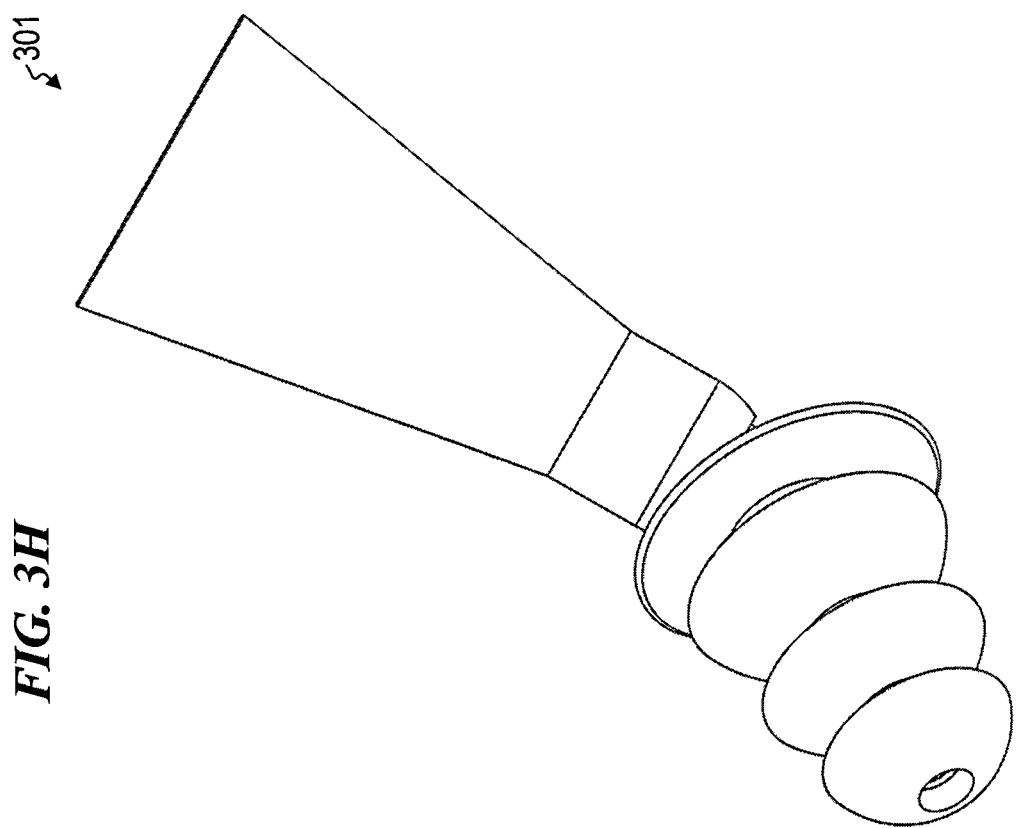
FIG. 3H is a second perspective-view diagram of tuned-frequency-spectrum earpiece 301, according to some embodiments of the present invention.
Figure 3G:
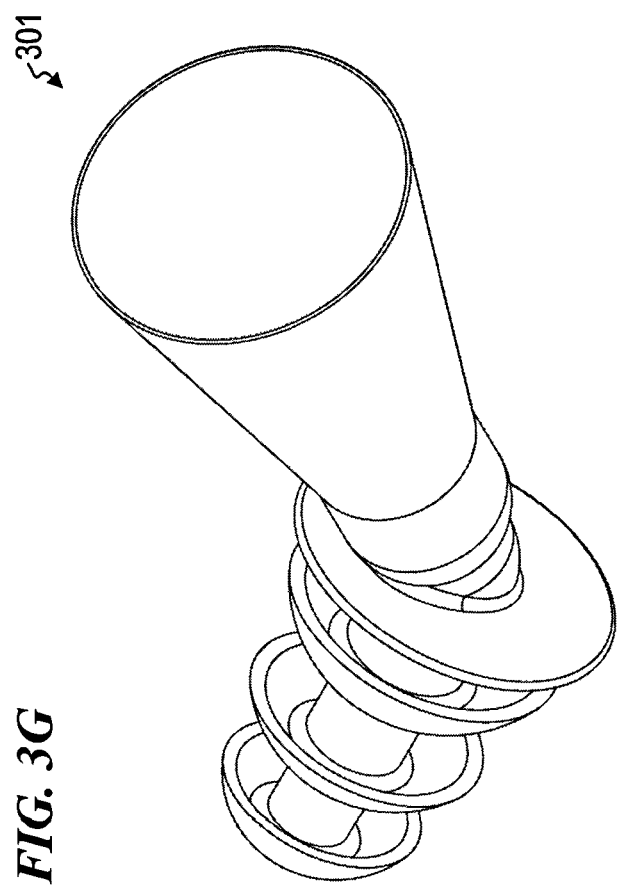
FIG. 3G is a first perspective-view diagram of tuned-frequency-spectrum earpiece 301, according to some embodiments of the present invention.

FIG. 3G is a first perspective-view diagram of tuned-frequency-spectrum earpiece 301, according to some embodiments of the present invention.

FIG. 3H is a second perspective-view diagram of tuned-frequency-spectrum earpiece 301, according to some embodiments of the present invention.

Figure 4A:
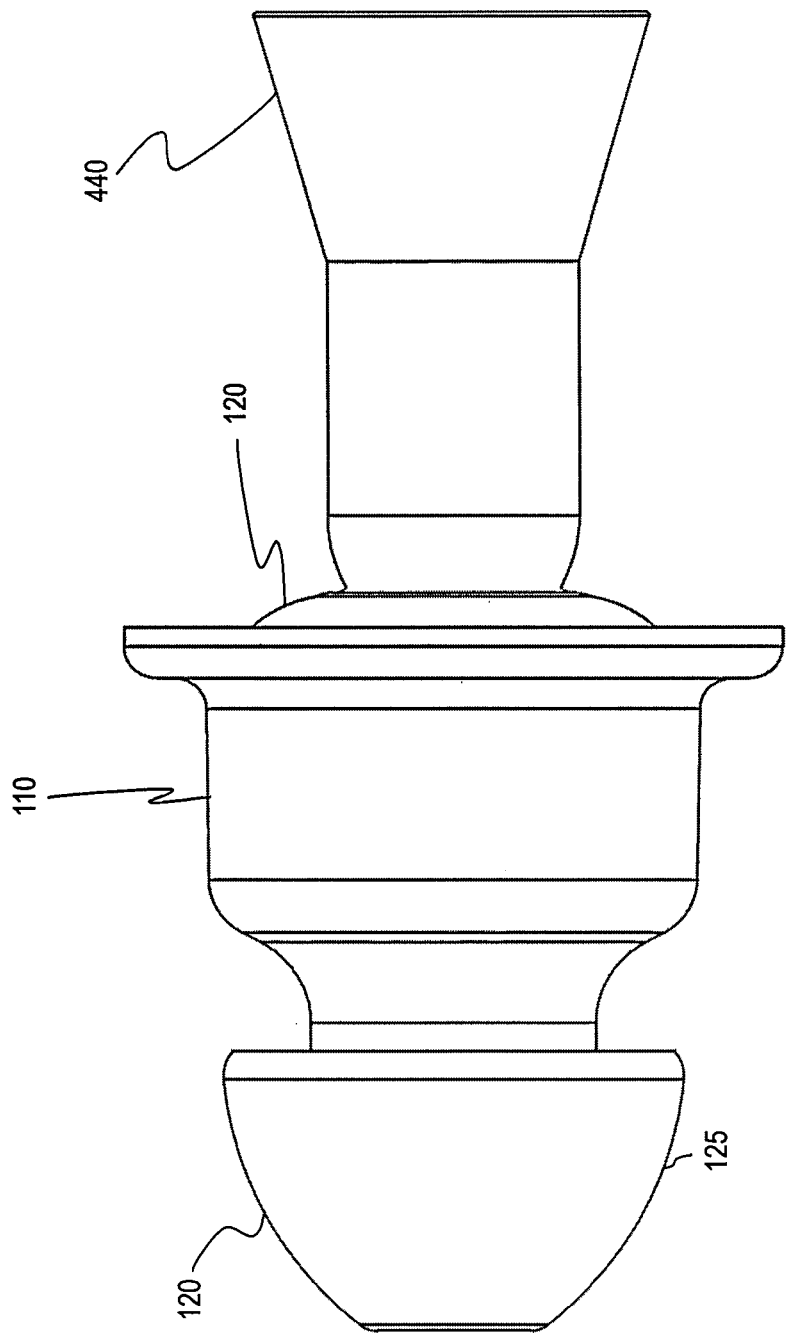
FIG. 4A a first side-view diagram of a tuned-frequency-spectrum earpiece 401, according to some embodiments of the present invention.

FIG. 4A is a first side-view diagram of a tuned-frequency-spectrum earpiece 401, according to some embodiments of the present invention. In some embodiments, earpiece 401 is substantially similar to earpiece 101 of FIG. 1A, except that horn 140 of FIG. 1A is replaced with horn 440. In some embodiments, horn 440 is shorter or longer in length and/or smaller or larger in diameter and/or has a different conical, paraboloid, elliptical paraboloid, or other shape configured to tune a frequency-spectrum and/or amplitude of passed audio, rather than conical horn 140.

Figure 4B:
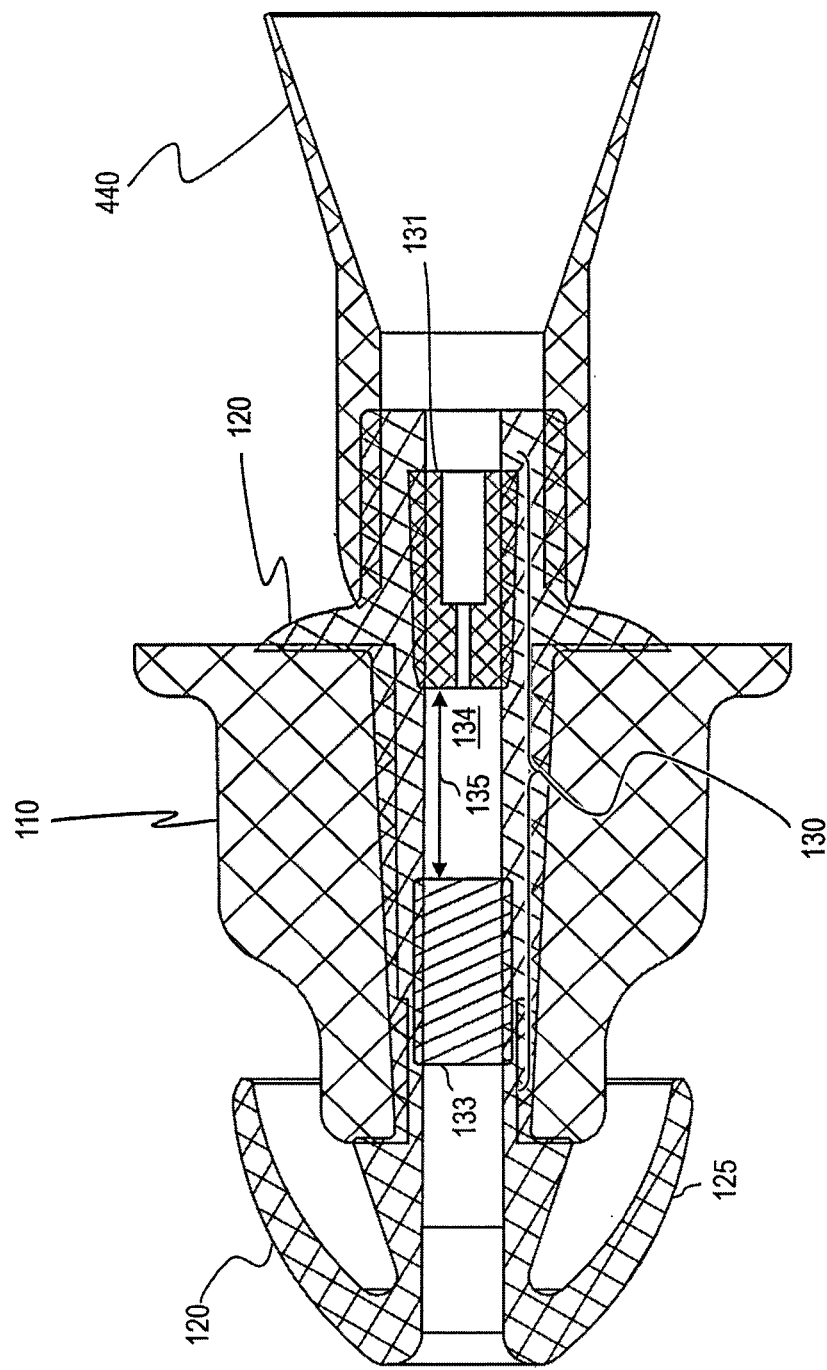
FIG. 4B is a cross-section view of tuned-frequency-spectrum earpiece 401, according to some embodiments of the present invention.

FIG. 4B is a cross-section view of tuned-frequency-spectrum earpiece 401, according to some embodiments of the present invention.

Figure 4C:
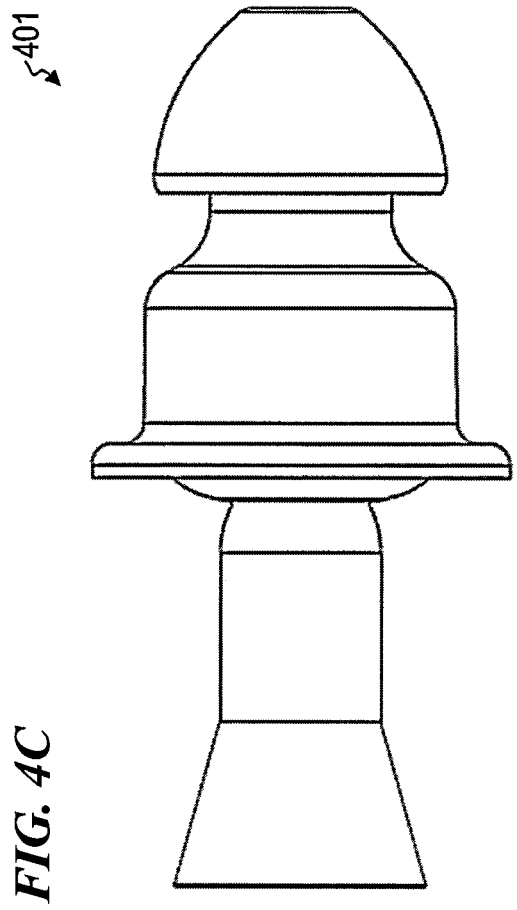
FIG. 4C is a second side-view diagram of tuned-frequency-spectrum earpiece 401, according to some embodiments of the present invention.

FIG. 4C is a second side-view diagram of tuned-frequency-spectrum earpiece 401, according to some embodiments of the present invention.

Figure 4E:
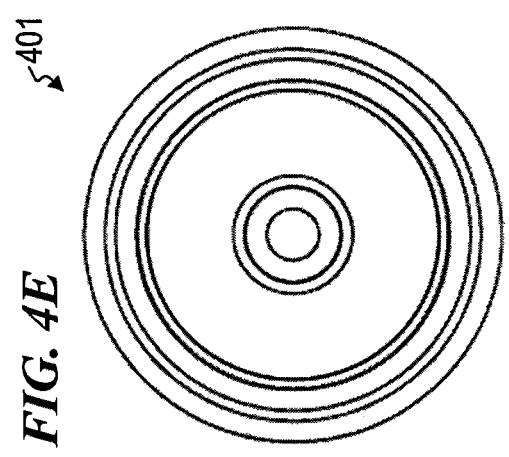
FIG. 4E is a second end-view diagram of tuned-frequency-spectrum earpiece 401, according to some embodiments of the present invention.
Figure 4D:
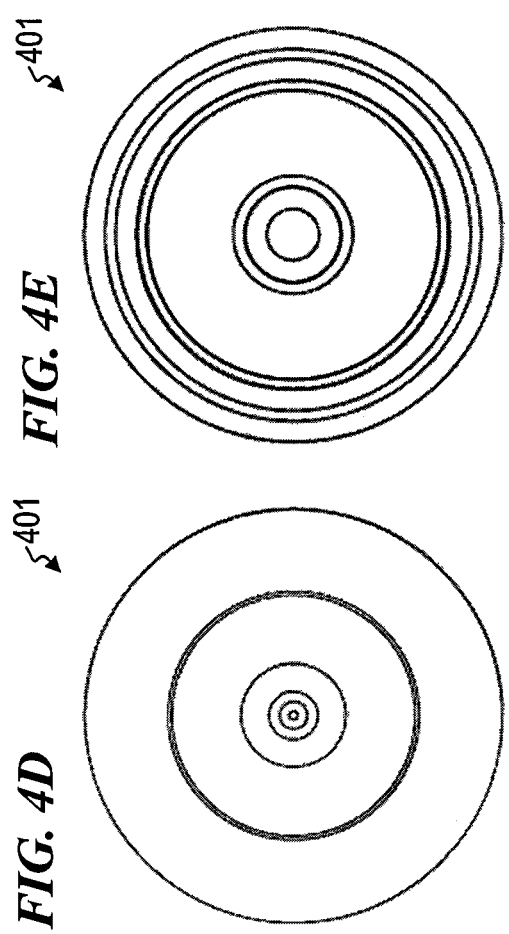
FIG. 4D is a first end-view diagram of tuned-frequency-spectrum earpiece 401, according to some embodiments of the present invention.

FIG. 4D is a first end-view diagram of tuned-frequency-spectrum earpiece 401, according to some embodiments of the present invention. In some embodiments, the first end-view diagram of FIG. 4D shows the view if facing the end of horn 440.

FIG. 4E is a second end-view diagram of tuned-frequency-spectrum earpiece 401, according to some embodiments of the present invention. In some embodiments, the second end-view diagram of FIG. 4E shows the view if facing the end of distal flange 125 of base 120.

Figure 4F:
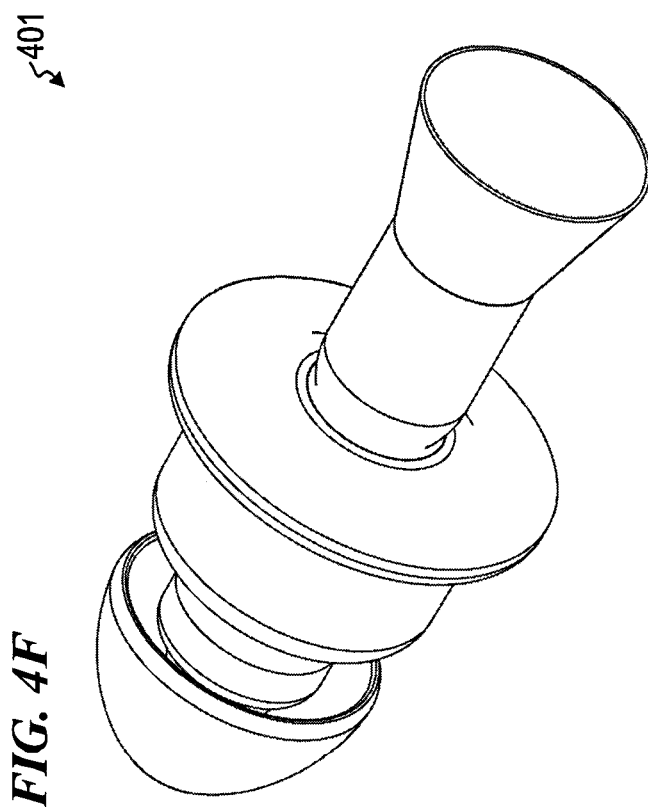
FIG. 4F is a first perspective-view diagram of tuned-frequency-spectrum earpiece 401, according to some embodiments of the present invention.

FIG. 4F is a first perspective-view diagram of tuned-frequency-spectrum earpiece 401, according to some embodiments of the present invention.

Figure 4G:
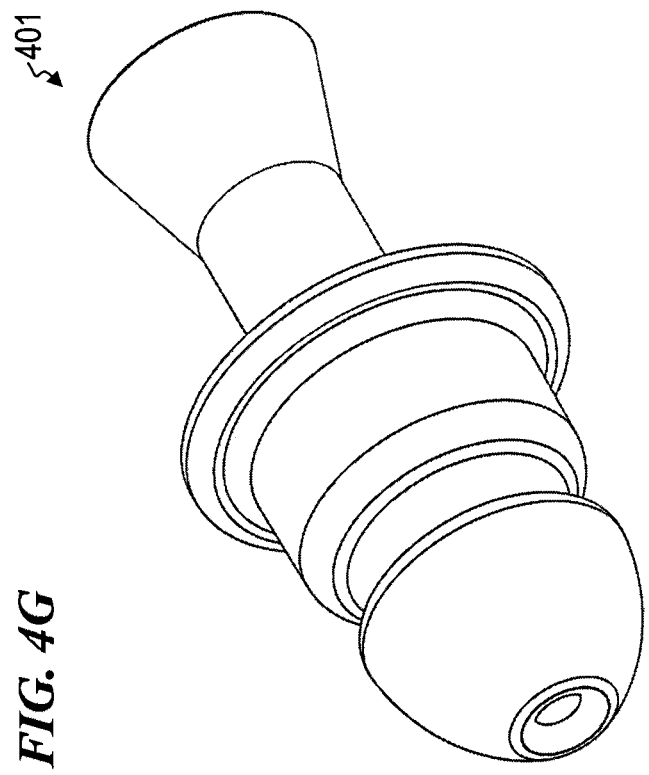
FIG. 4G is a second perspective-view diagram of tuned-frequency-spectrum earpiece 401, according to some embodiments of the present invention.

FIG. 4G is a second perspective-view diagram of tuned-frequency-spectrum earpiece 401, according to some embodiments of the present invention.

Figure 5A:
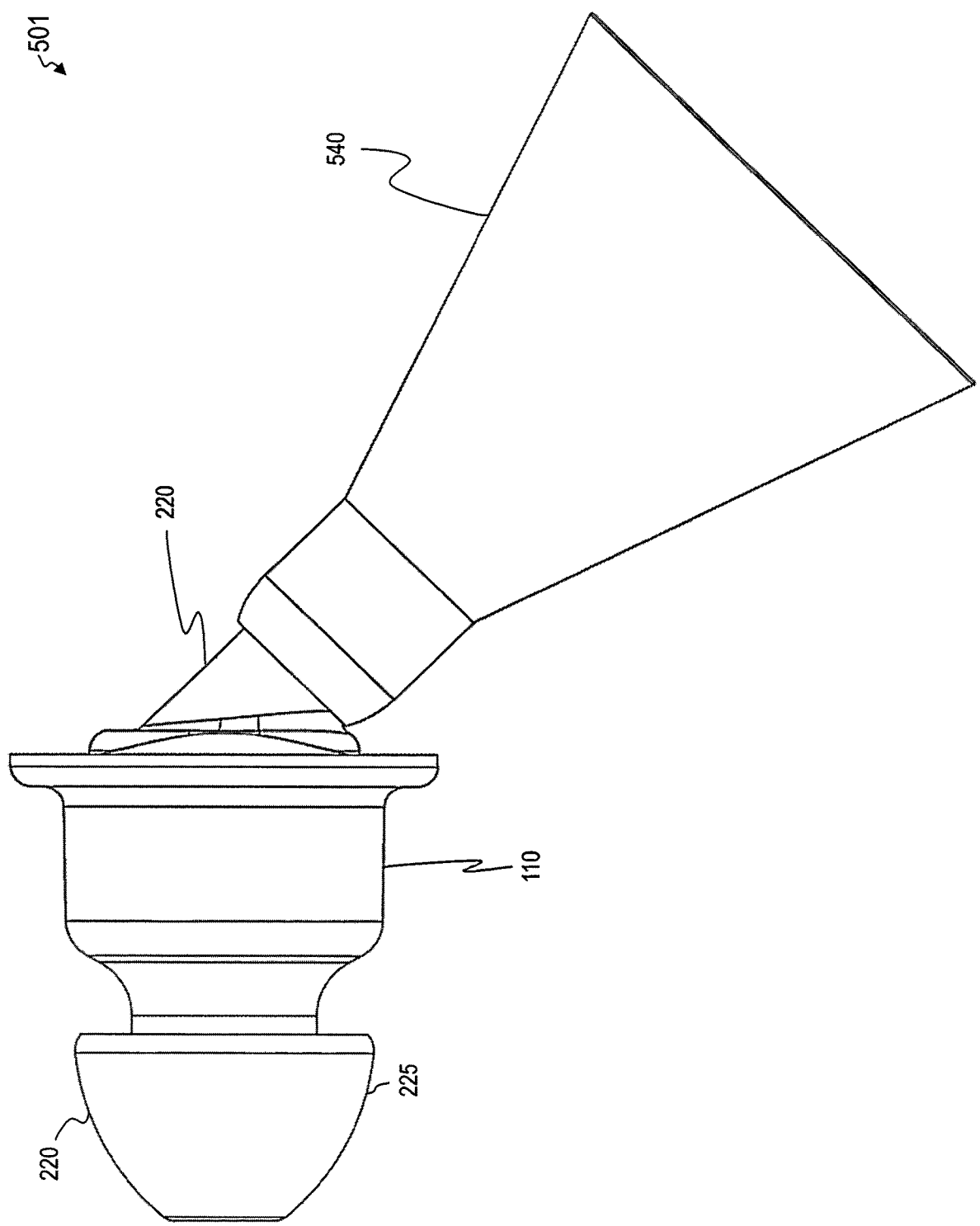
FIG. 5A is a side-view diagram of a tuned-frequency-spectrum earpiece 501, according to some embodiments of the present invention.

FIG. 5A is a side-view diagram of a tuned-frequency-spectrum earpiece 501, according to some embodiments of the present invention. In some embodiments, earpiece 501 is substantially similar to earpiece 101 of FIG. 1A, except that horn 140 is replaced with horn 540. In some embodiments, horn 540 has a larger diameter and/or a longer length than horn 140.

Figure 5B:
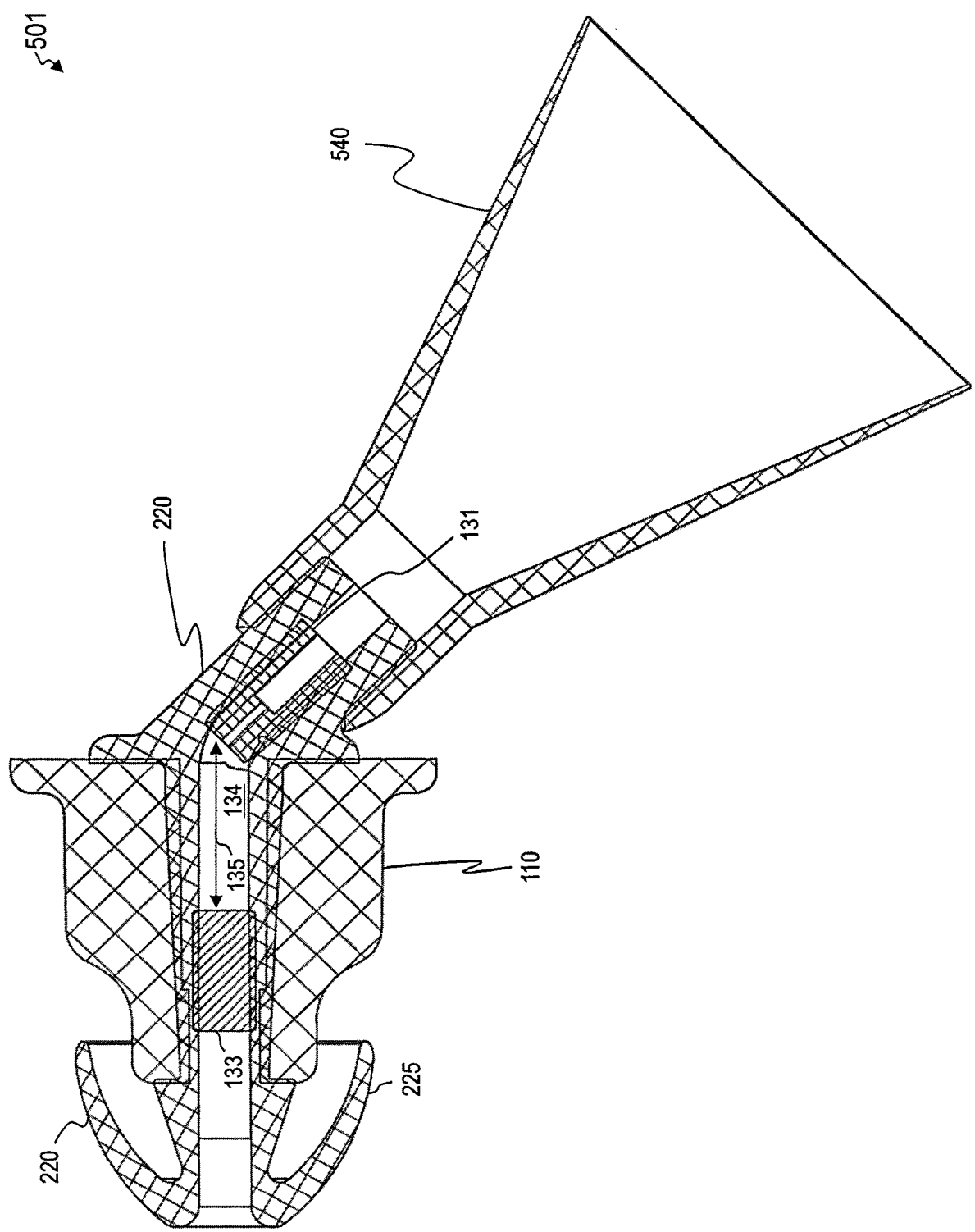
FIG. 5B is a cross-section view of tuned-frequency-spectrum earpiece 501, according to some embodiments of the present invention.

FIG. 5B is a cross-section view of tuned-frequency-spectrum earpiece 501, according to some embodiments of the present invention.

Figure 5C:
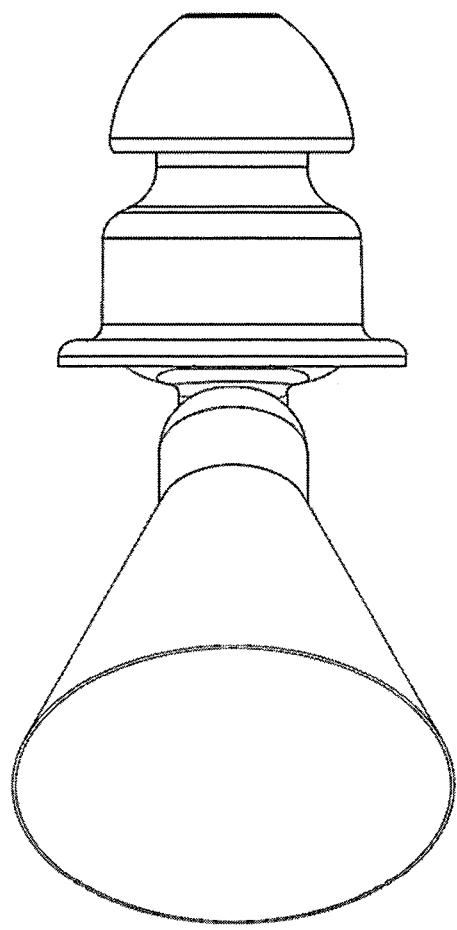
FIG. 5C is a top-view diagram of tuned-frequency-spectrum earpiece 501, according to some embodiments of the present invention.

FIG. 5C is a top-view diagram of tuned-frequency-spectrum earpiece 501, according to some embodiments of the present invention.

Figure 5D:
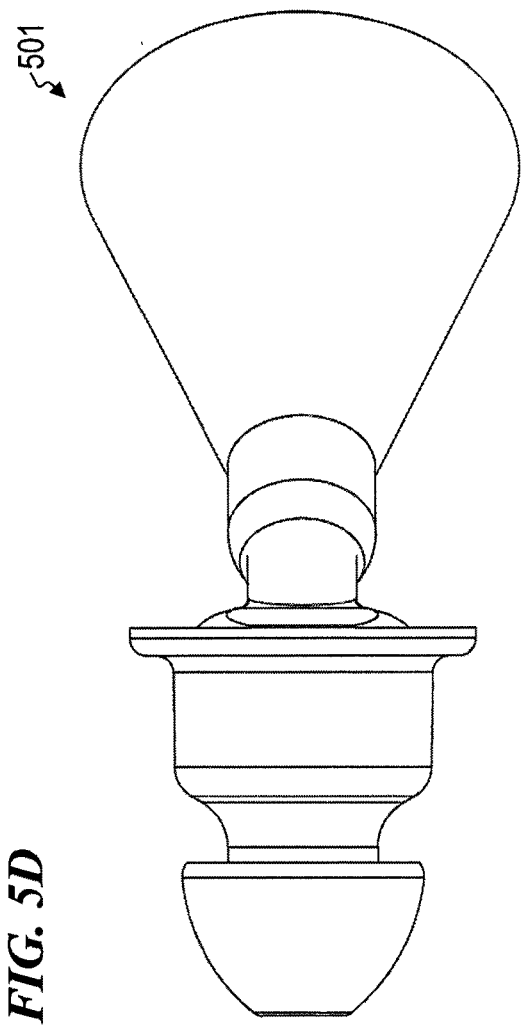
FIG. 5D is a bottom-view diagram of tuned-frequency-spectrum earpiece 501, according to some embodiments of the present invention.

FIG. 5D is a bottom-view diagram of tuned-frequency-spectrum earpiece 501, according to some embodiments of the present invention.

Figure 5F:
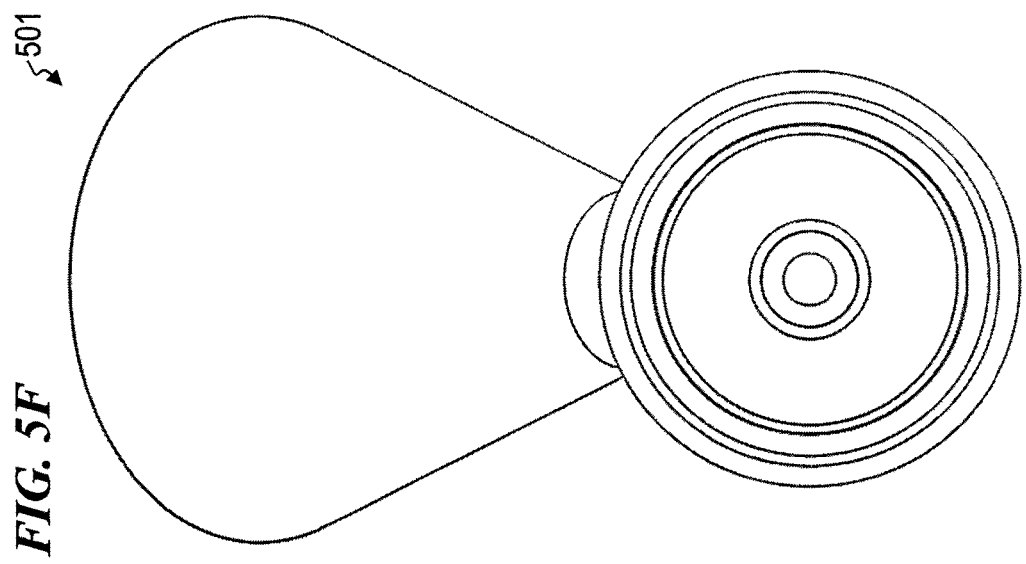
FIG. 5F is a second end-view diagram of tuned-frequency-spectrum earpiece 501, according to some embodiments of the present invention.
Figure 5E:
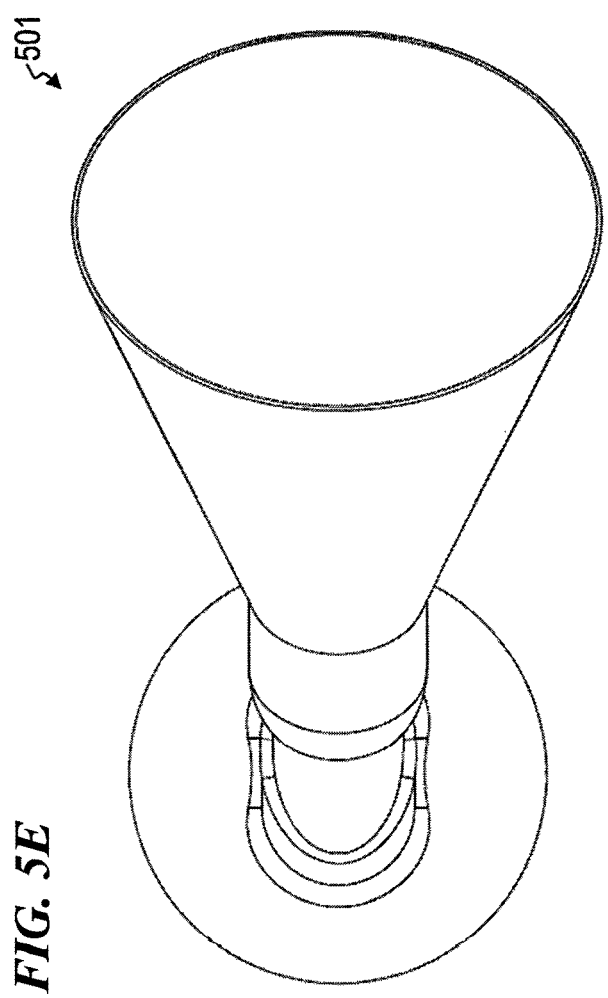
FIG. 5E is a first end-view diagram of tuned-frequency-spectrum earpiece 501, according to some embodiments of the present invention.

FIG. 5E is a first end-view diagram of tuned-frequency-spectrum earpiece 501, according to some embodiments of the present invention. In some embodiments, the first end-view diagram of FIG. 5E shows the view if facing earpiece 501 from the end that includes horn 540.

FIG. 5F is a second end-view diagram of tuned-frequency-spectrum earpiece 501, according to some embodiments of the present invention. In some embodiments, the second end-view diagram of FIG. 5F shows the view if facing the end of distal flange 225 of base 220.

Figure 5H:
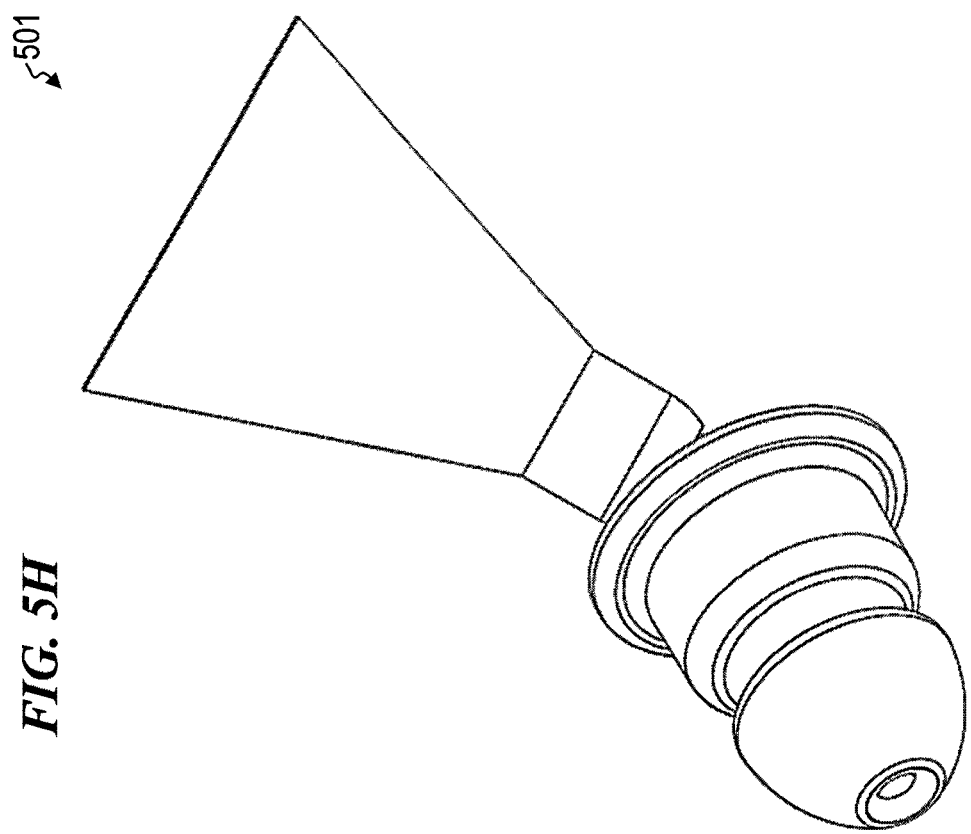
FIG. 5H is a second perspective-view diagram of tuned-frequency-spectrum earpiece 501, according to some embodiments of the present invention.
Figure 5G:
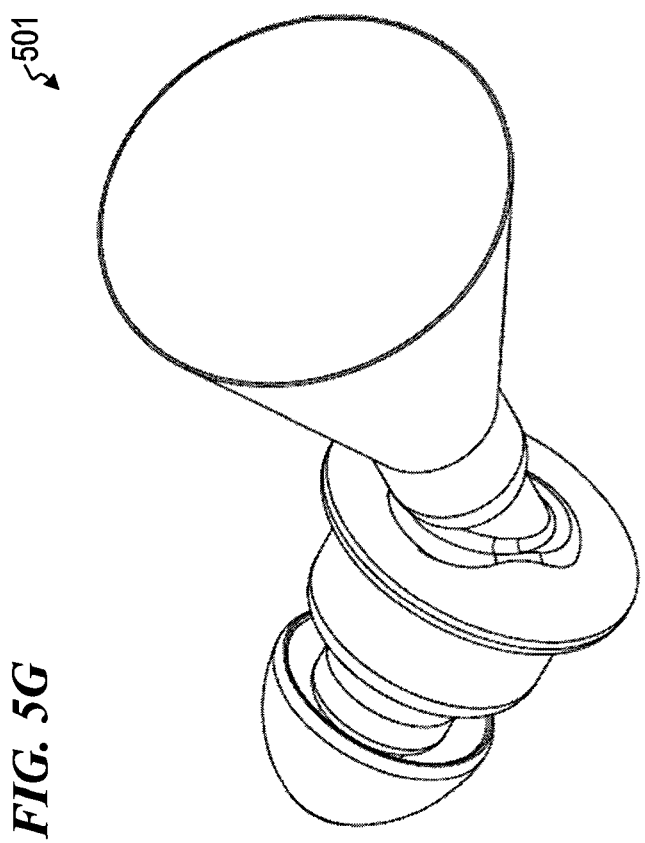
FIG. 5G is a first perspective-view diagram of tuned-frequency-spectrum earpiece 501, according to some embodiments of the present invention.

FIG. 5G is a first perspective-view diagram of tuned-frequency-spectrum earpiece 501, according to some embodiments of the present invention.

FIG. 5H is a second perspective-view diagram of tuned-frequency-spectrum earpiece 501, according to some embodiments of the present invention.

Figure 6A:
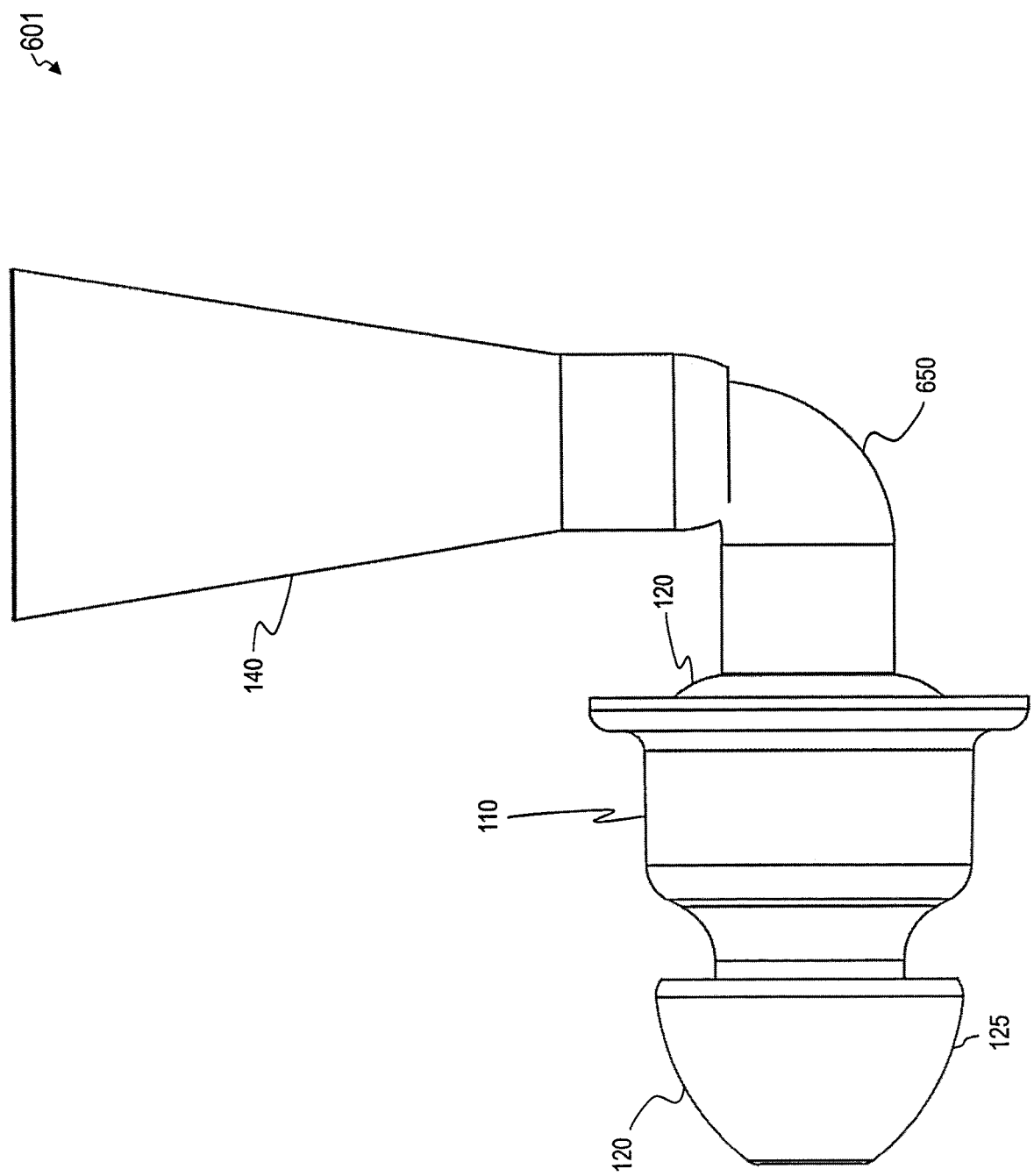
FIG. 6A is a side-view diagram of a tuned-frequency-spectrum earpiece 601, according to some embodiments of the present invention.

FIG. 6A is a side-view diagram of a tuned-frequency-spectrum earpiece 601, according to some embodiments of the present invention. In some embodiments, earpiece 601 is substantially similar to earpiece 101 of FIG. 1A, except that an elbow extension 650 is added between base 120 and horn 140.

Figure 6B:
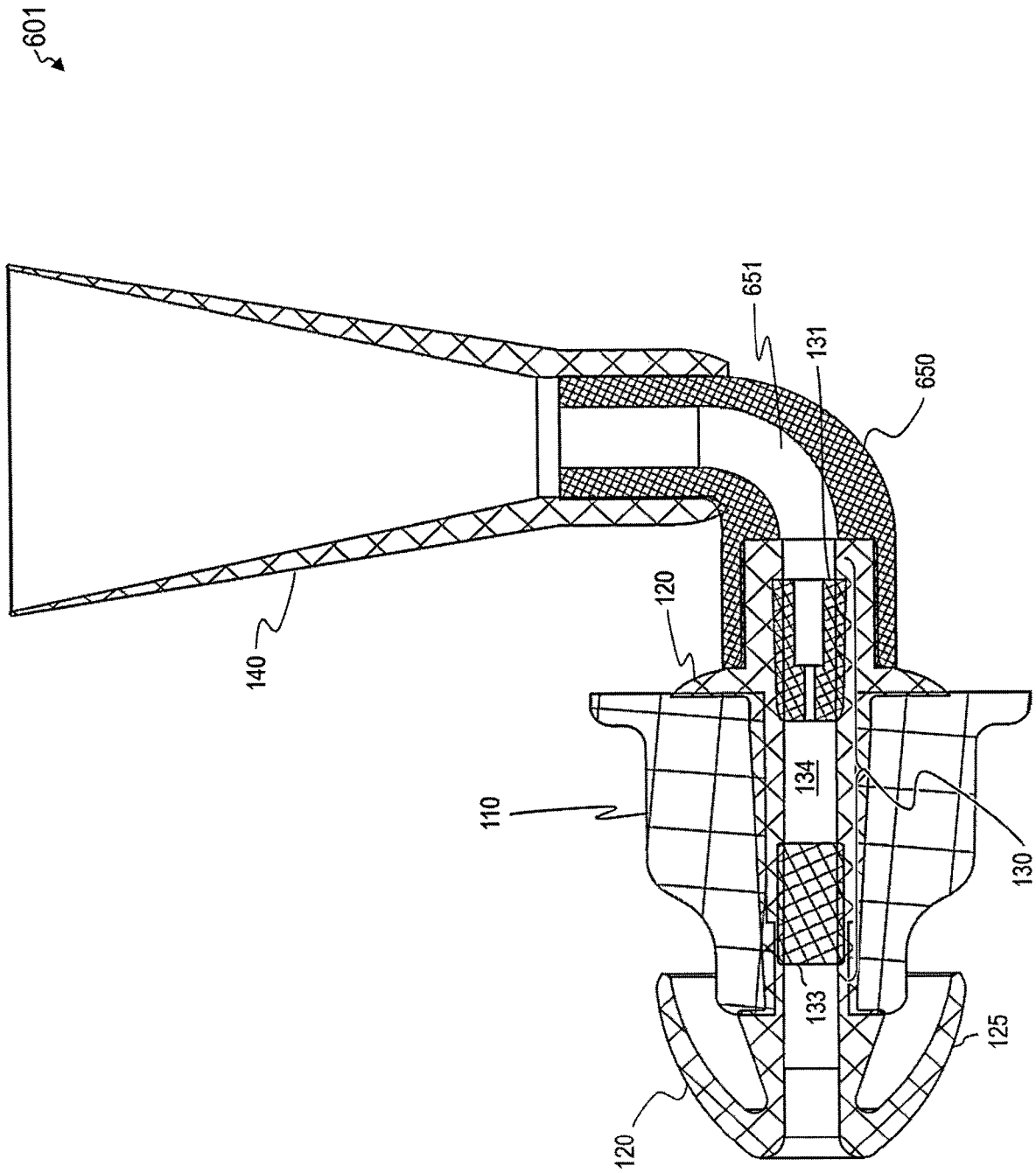
FIG. 6B is a cross-section view of tuned-frequency-spectrum earpiece 601, according to some embodiments of the present invention.

FIG. 6B is a cross-section view of tuned-frequency-spectrum earpiece 601, according to some embodiments of the present invention. In some embodiments, elbow extension 650 is injection molded and is made from a material that includes a suitable plastic polymer. In some embodiments, elbow extension 650 is made from a material that includes a cured plastisol (e.g., a PVC). In some embodiments, elbow extension 650 includes a channel 651 that passes through elbow extension 650. In some embodiments, frequency horn 140 couples to a first end of elbow extension 650 (in some such embodiments, the first end of elbow extension 650 is inserted into horn 140) and base 120 is inserted into a second end of elbow extension 650 (in some such embodiments, channel 651 includes a first diameter and a second diameter where the first diameter is larger than the second diameter and base 120 is inserted into the larger first diameter of channel 651). In some embodiments, elbow extension 650 allows the horn 140 to be directed out of the ear at a direction more suitable to receiving the desired audio frequencies.

Figure 6D:
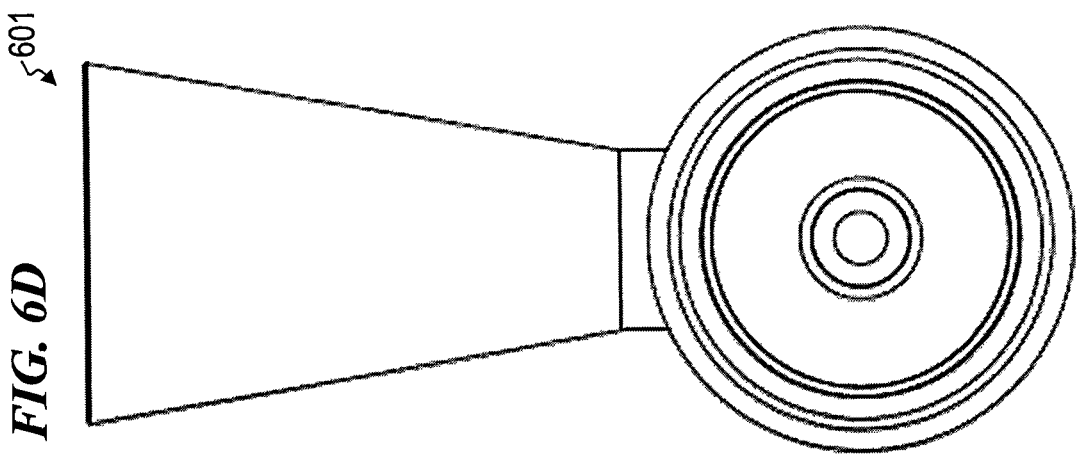
FIG. 6D is a second end-view diagram of tuned-frequency-spectrum earpiece 601, according to some embodiments of the present invention.
Figure 6C:
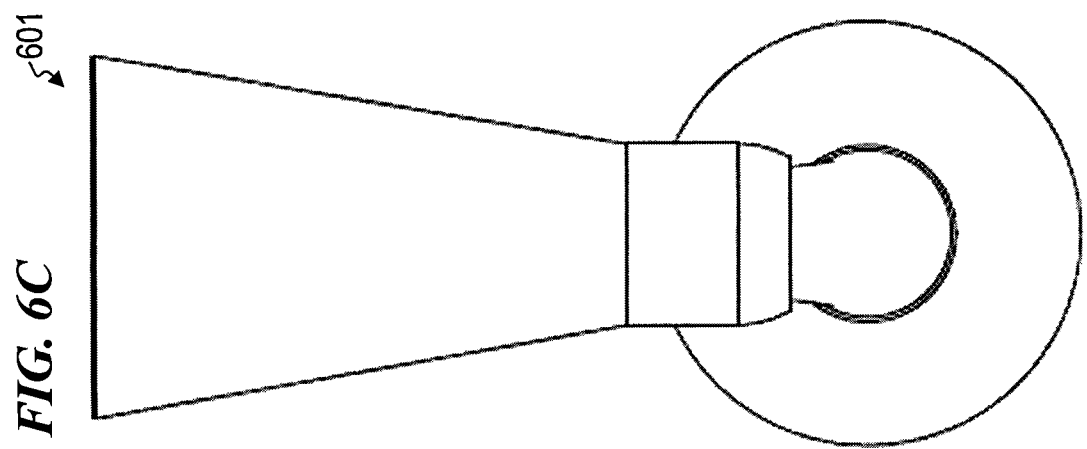
FIG. 6C is a first end-view diagram of tuned-frequency-spectrum earpiece 601, according to some embodiments of the present invention.

FIG. 6C is a first end-view diagram of tuned-frequency-spectrum earpiece 601, according to some embodiments of the present invention. In some embodiments, the first end-view diagram of FIG. 6C shows the view if facing earpiece 601 from the end that includes horn 140.

FIG. 6D is a second end-view diagram of tuned-frequency-spectrum earpiece 601, according to some embodiments of the present invention. In some embodiments, the second end-view diagram of FIG. 6D shows the view if facing the end of distal flange 125 of base 120.

FIG. 6E is a first perspective-view diagram of tuned-frequency-spectrum earpiece 601, according to some embodiments of the present invention.

FIG. 6F is a second perspective-view diagram of tuned-frequency-spectrum earpiece 601, according to some embodiments of the present invention.

Figure 7C:
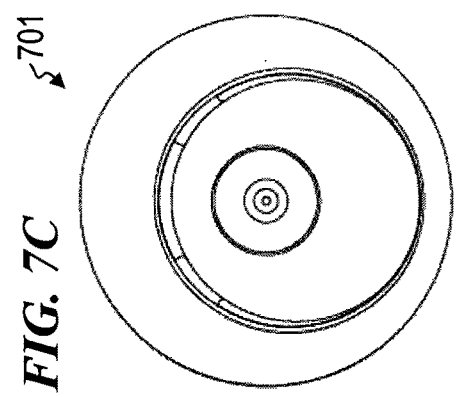
FIG. 7C is a first end-view diagram of tuned-frequency-spectrum earpiece 701, according to some embodiments of the present invention.
Figure 7D:
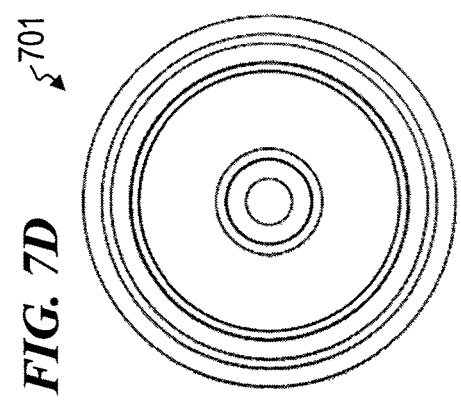
FIG. 7D is a second end-view diagram of tuned-frequency-spectrum earpiece 701, according to some embodiments of the present invention.
Figure 7A:
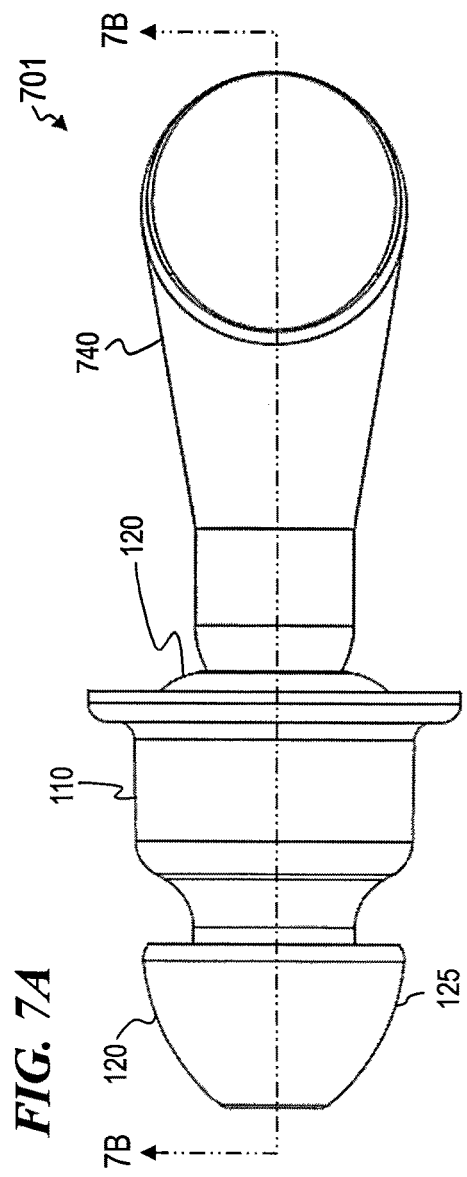
FIG. 7A is a top-view diagram of a tuned-frequency-spectrum earpiece 701, according to some embodiments of the present invention.

FIG. 7A is a top-view diagram of a tuned-frequency-spectrum earpiece 701, according to some embodiments of the present invention. In some embodiments, earpiece 701 is substantially similar to earpiece 101 except that horn 140 is replaced with horn 740. In some embodiments, the input end 741 of horn 740 is at a non-90-degree angle (e.g., 45 degrees) relative to the longitudinal axis of horn 740.

Figure 7B:
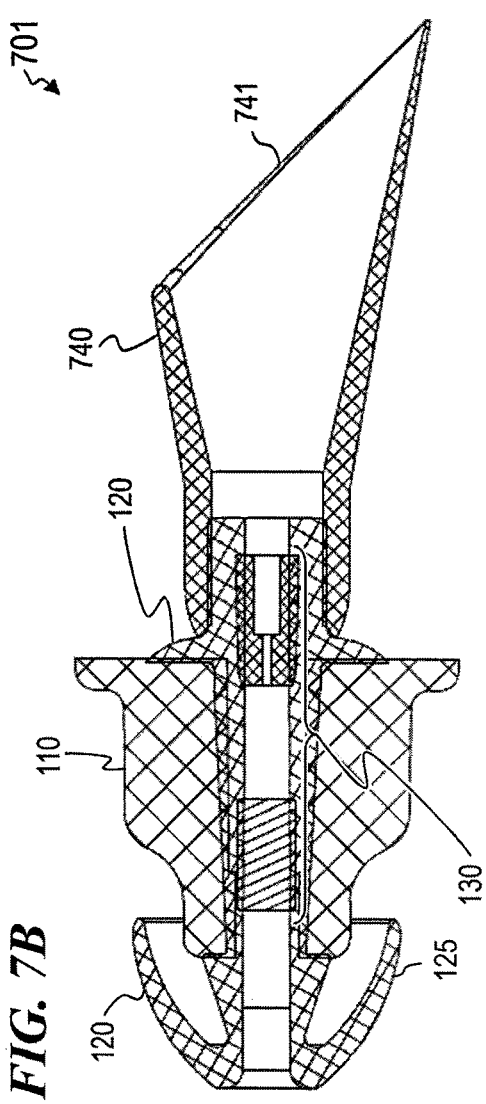
FIG. 7B is a cross-section view of tuned-frequency-spectrum earpiece 701, according to some embodiments of the present invention, as viewed along cross-section line 7B in FIG. 7A.

FIG. 7B is a cross-section view of tuned-frequency-spectrum earpiece 701, according to some embodiments of the present invention, as viewed along cross-section line 7B in FIG. 7A.

FIG. 7C is a first end-view diagram of tuned-frequency-spectrum earpiece 701, according to some embodiments of the present invention. In some embodiments, the first end-view diagram of FIG. 7C shows the view if facing the end of horn 740.

FIG. 7D is a second end-view diagram of tuned-frequency-spectrum earpiece 701, according to some embodiments of the present invention. In some embodiments, the second end-view diagram of FIG. 7D shows the view if facing the end of distal flange 125 of base 120.

FIG. 7E is a first perspective-view diagram of tuned-frequency-spectrum earpiece 701, according to some embodiments of the present invention.

FIG. 7F is a second perspective-view diagram of tuned-frequency-spectrum earpiece 701, according to some embodiments of the present invention.

Figure 8C:
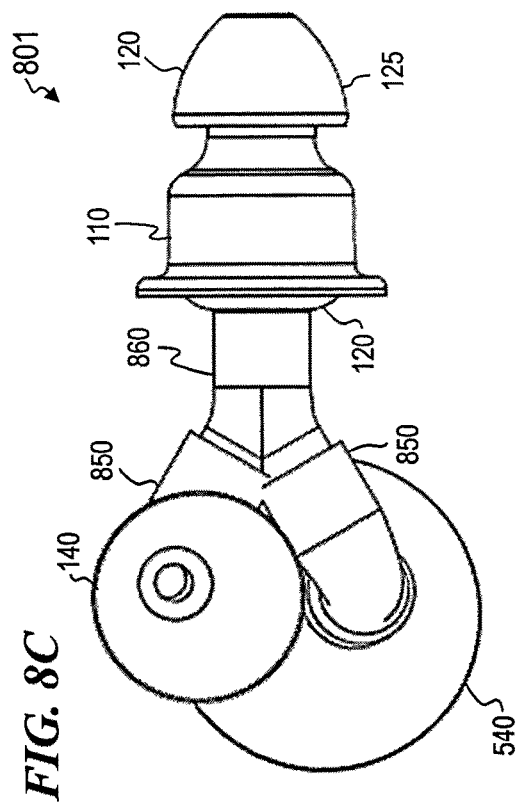
FIG. 8C is a second side-view diagram of tuned-frequency-spectrum earpiece 801, according to some embodiments of the present invention.
Figure 8A:
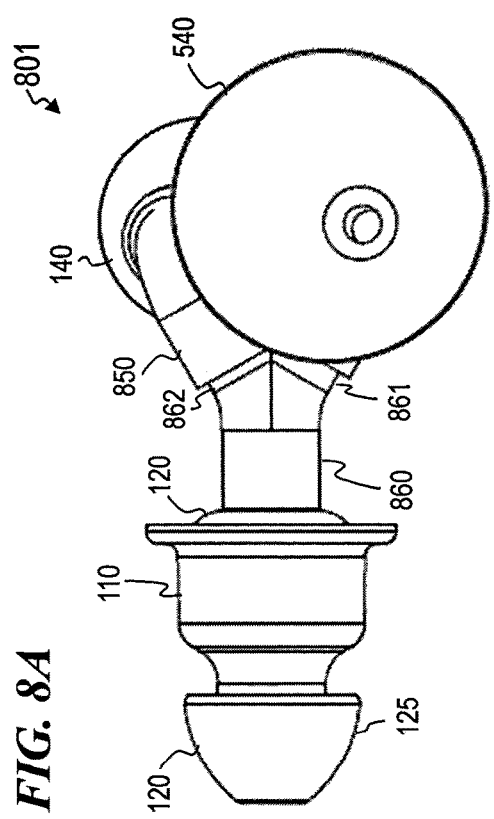
FIG. 8A is a first side-view diagram of a tuned-frequency-spectrum earpiece 801, according to some embodiments of the present invention.

FIG. 8A is a first side-view diagram of a tuned-frequency-spectrum earpiece 801, according to some embodiments of the present invention. In some embodiments, earpiece 801 is substantially similar to earpiece 101 of FIG. 1A except that earpiece 801 further includes a split connector 860, two elbow connectors 850, and two horns (e.g., in some embodiments, horn 140 and horn 540). In some other embodiments (not shown), a plurality of horns at a plurality of different orientations or angles are provided, such as three or more horns, pointed or oriented to selectively collect relatively more sound from certain directions and relatively less sound from other directions. In some embodiments, split connector 860 includes a first end and a second end, wherein the second end includes a first receiver portion 861 and a second receiver portion 862. In some embodiments, the receiver end of base 120 is inserted into the first end of split connector 860, each respective receiver portion 861 and 862 is inserted into a first end of a respective elbow connector 850, and the second ends of each respective elbow connector 850 are inserted into a respective horn. In some embodiments, earpiece 801 allows audio frequencies to be received into horn 140 as horn 140 faces forward from the user 99 while audio frequencies are also received into horn 540 as horn 540 faces backward from user 99 (see FIG. 8H). In some embodiments, split connector 860 and elbow connectors 850 are made from any suitable plastic polymer, cured plastisol, or the like. In some embodiments, connector 860 and elbow connectors 850 are injection molded.

Figure 8B:
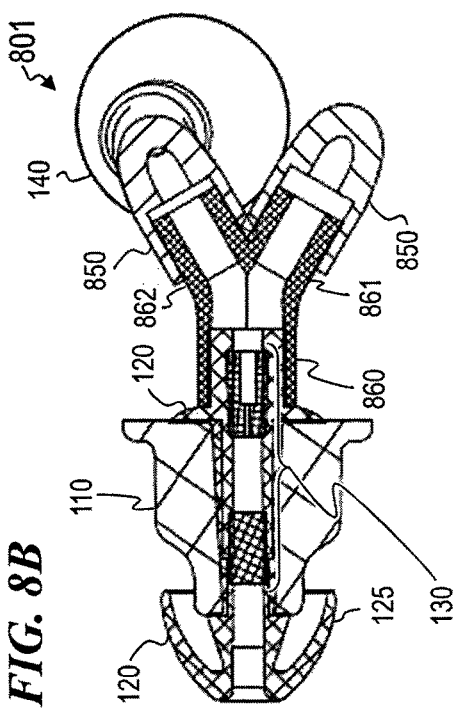
FIG. 8B is a cross-section view of tuned-frequency-spectrum earpiece 801, according to some embodiments of the present invention, as viewed along cross-section line 8B in FIG. 8D.
Figure 8D:
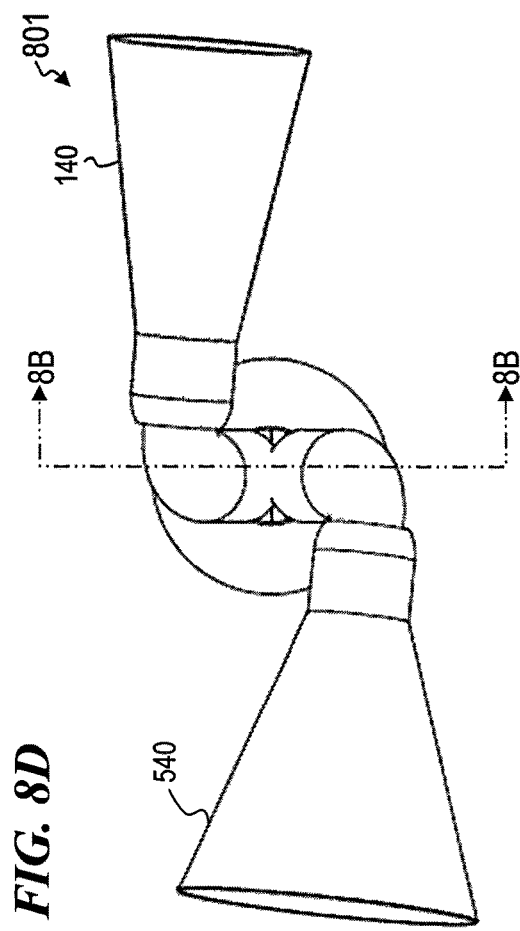
FIG. 8D is a first end-view diagram of tuned-frequency-spectrum earpiece 801, according to some embodiments of the present invention.

FIG. 8B is a cross-section view of tuned-frequency-spectrum earpiece 801, according to some embodiments of the present invention, as viewed along cross-section line 8B in FIG. 8D.

FIG. 8C is a second side-view diagram of tuned-frequency-spectrum earpiece 801, according to some embodiments of the present invention.

FIG. 8D is a first end-view diagram of tuned-frequency-spectrum earpiece 801, according to some embodiments of the present invention. In some embodiments, the first end-view diagram of FIG. 8D shows the view if facing earpiece 801 from the end that includes horn 140 and horn 540.

Figure 8E:
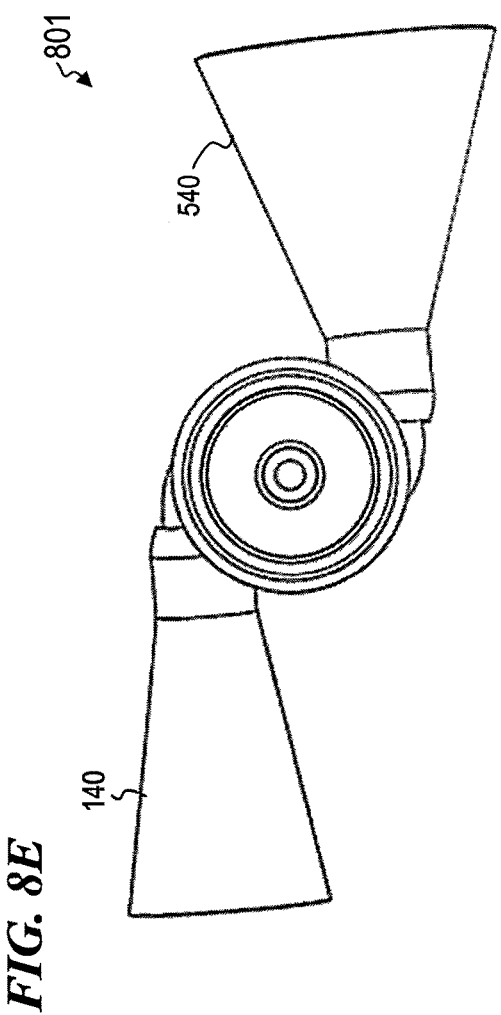
FIG. 8E is a second end-view diagram of tuned-frequency-spectrum earpiece 801, according to some embodiments of the present invention.

FIG. 8E is a second end-view diagram of tuned-frequency-spectrum earpiece 801, according to some embodiments of the present invention. In some embodiments, the second end-view diagram of FIG. 8E shows the view if facing the end of distal flange 125 of base 120.

Figure 8G:
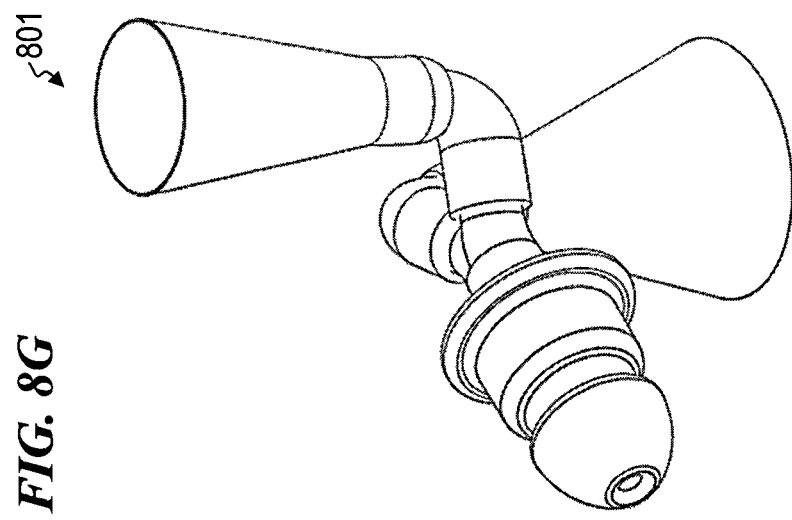
FIG. 8G is a second perspective-view diagram of tuned-frequency-spectrum earpiece 801, according to some embodiments of the present invention.
Figure 8F:
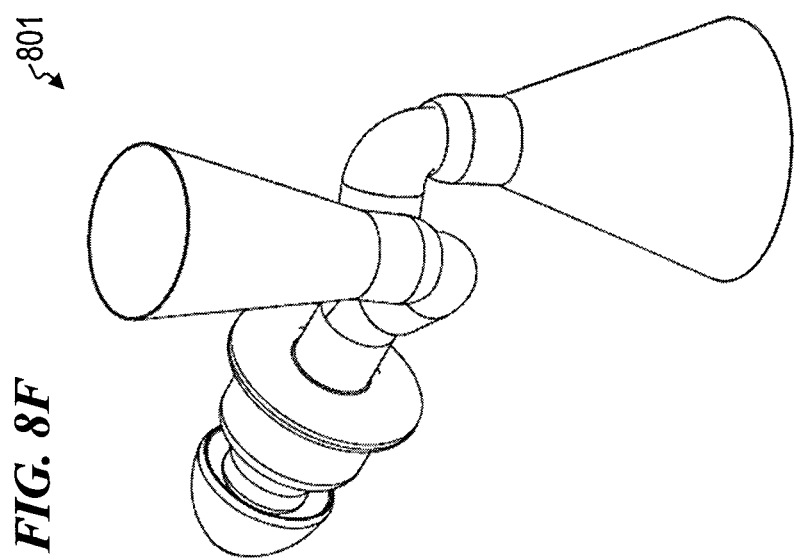
FIG. 8F is a first perspective-view diagram of tuned-frequency-spectrum earpiece 801, according to some embodiments of the present invention.

FIG. 8F is a first perspective-view diagram of tuned-frequency-spectrum earpiece 801, according to some embodiments of the present invention.

FIG. 8G is a second perspective-view diagram of tuned-frequency-spectrum earpiece 801, according to some embodiments of the present invention.

Figure 8H:
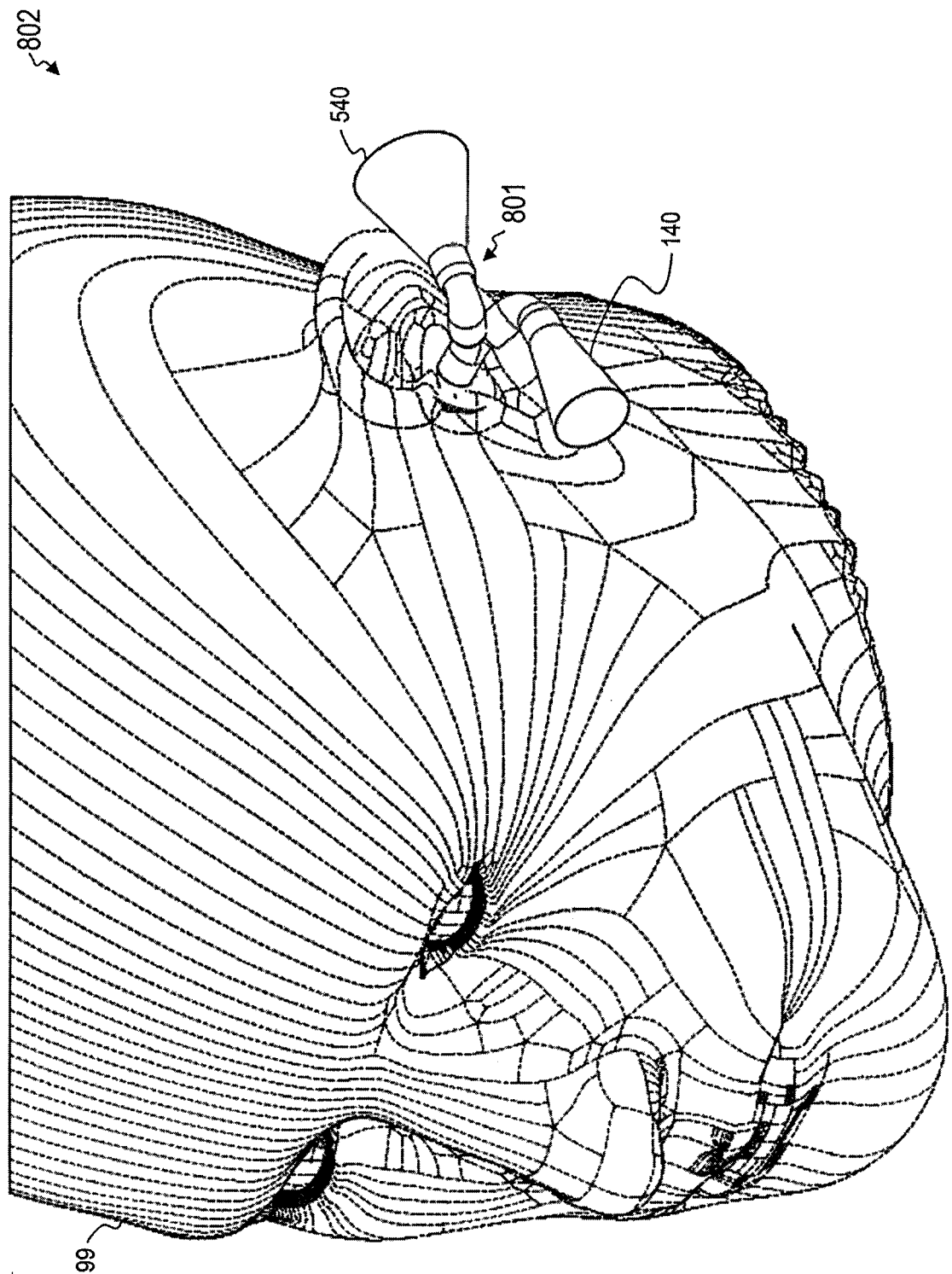
FIG. 8H is a schematic diagram of a tuned-frequency-spectrum system 802, according to some embodiments of the present invention.

FIG. 8H is a schematic diagram of a tuned-frequency-spectrum system 802, according to some embodiments of the present invention. In some embodiments, earpiece 801 is inserted into the ear of user 99 such that horn 140 faces forward from user 99 and horn 540 faces backward from user 99. In some embodiments, earpiece 801 is inserted into the ear of user 99 such that horn 140 and horn 540 face any other suitable directions.

Figure 9C:
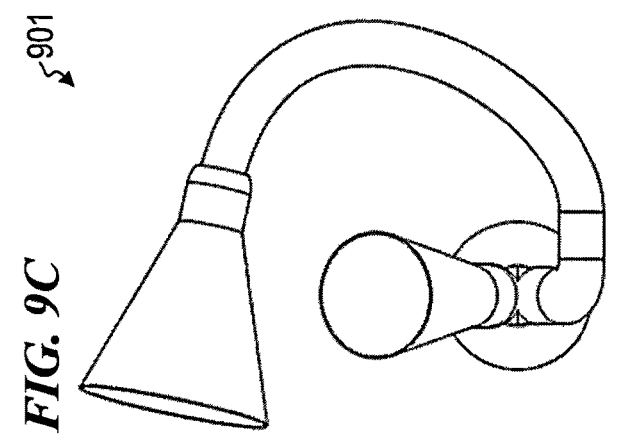
FIG. 9C is a first end-view diagram of tuned-frequency-spectrum earpiece 901, according to some embodiments of the present invention.
Figure 9D:
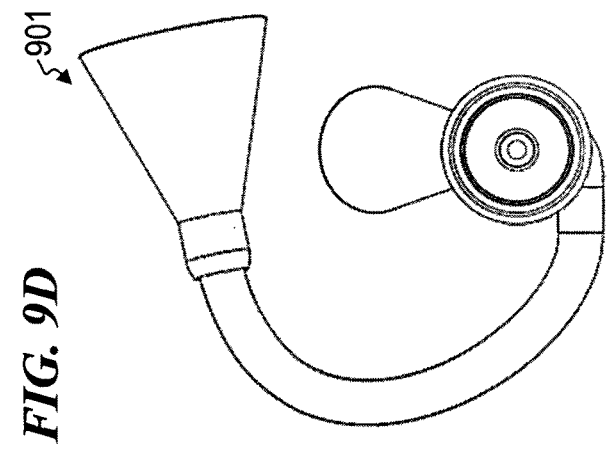
FIG. 9D is a second end-view diagram of tuned-frequency-spectrum earpiece 901, according to some embodiments of the present invention.
Figure 9A:
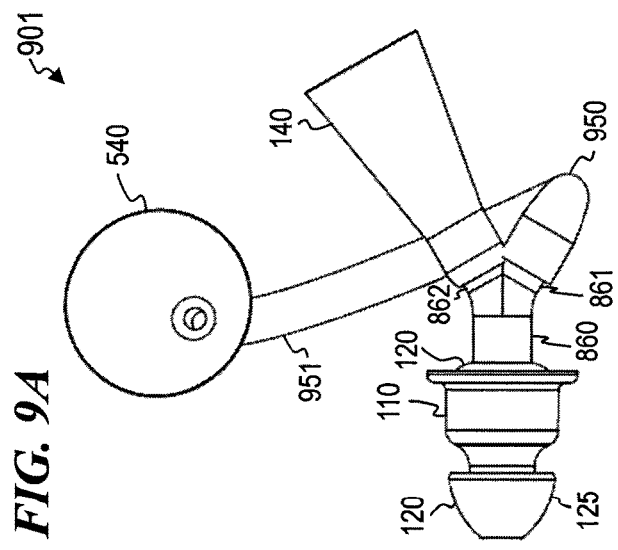
FIG. 9A is a side-view diagram of a tuned-frequency-spectrum earpiece 901, according to some embodiments of the present invention.

FIG. 9A is a side-view diagram of a tuned-frequency-spectrum earpiece 901, according to some embodiments of the present invention. In some embodiments, earpiece 901 is substantially similar to earpiece 801 of FIG. 8A except that earpiece 901 further includes an elbow connector 950 and an extension tube 951. In some embodiments, the receiver end of base 120 is inserted into a first end of split connector 860, first receiver portion 861 of split connector 860 is inserted into a first end of elbow connector 950, second receiver portion 862 of split connector 860 is inserted into horn 140, the second end of elbow connector 950 is inserted into a first end of extension tube 951, and horn 540 is coupled to a second end of extension tube 951. In some embodiments, earpiece 901 allows audio frequencies to be received into horn 140 as horn 140 faces outward from the user 99 while audio frequencies are also received into horn 540 as horn 540 faces forward from user 99 (see FIG. 9G). In some embodiments, elbow connector 950 and extension tube 951 are made from any suitable plastic polymer, cured plastisol, or the like. In some embodiments, elbow connector 950 and extension tube 951 are injection molded.

Figure 9B:
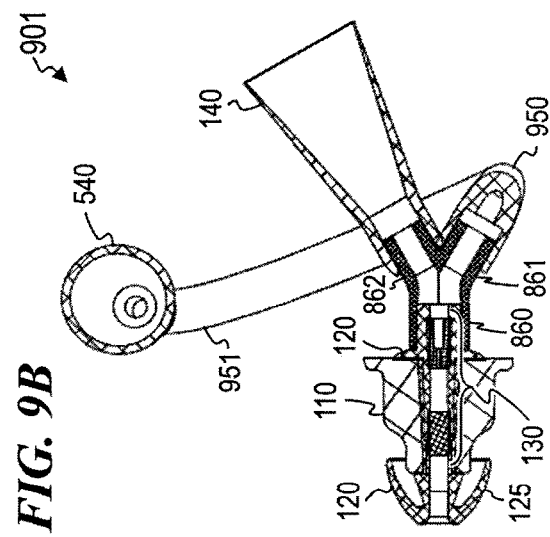
FIG. 9B is a cross-section view of tuned-frequency-spectrum earpiece 901, according to some embodiments of the present invention.

FIG. 9B is a cross-section view of tuned-frequency-spectrum earpiece 901, according to some embodiments of the present invention.

FIG. 9C is a first end-view diagram of tuned-frequency-spectrum earpiece 901, according to some embodiments of the present invention. In some embodiments, the first end-view diagram of FIG. 9C shows the view if facing earpiece 901 from the end that includes horn 140 and horn 540.

FIG. 9D is a second end-view diagram of tuned-frequency-spectrum earpiece 901, according to some embodiments of the present invention. In some embodiments, the second end-view diagram of FIG. 9D shows the view if facing the end of distal flange 125 of base 120.

Figure 9F:
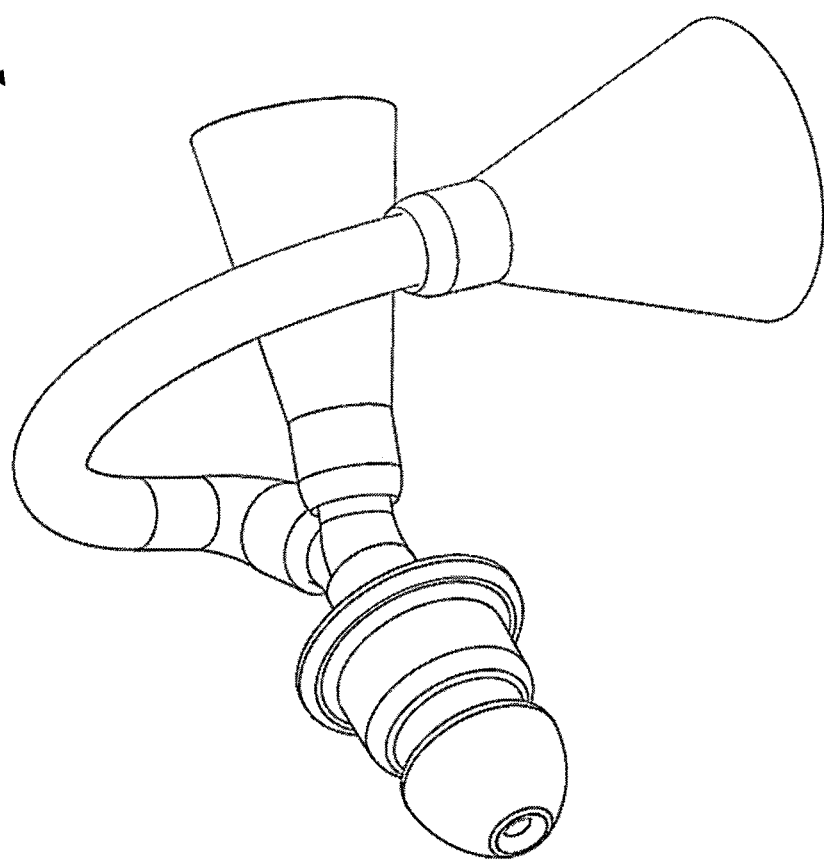
FIG. 9F is a second perspective-view diagram of tuned-frequency-spectrum earpiece 901, according to some embodiments of the present invention.
Figure 9E:
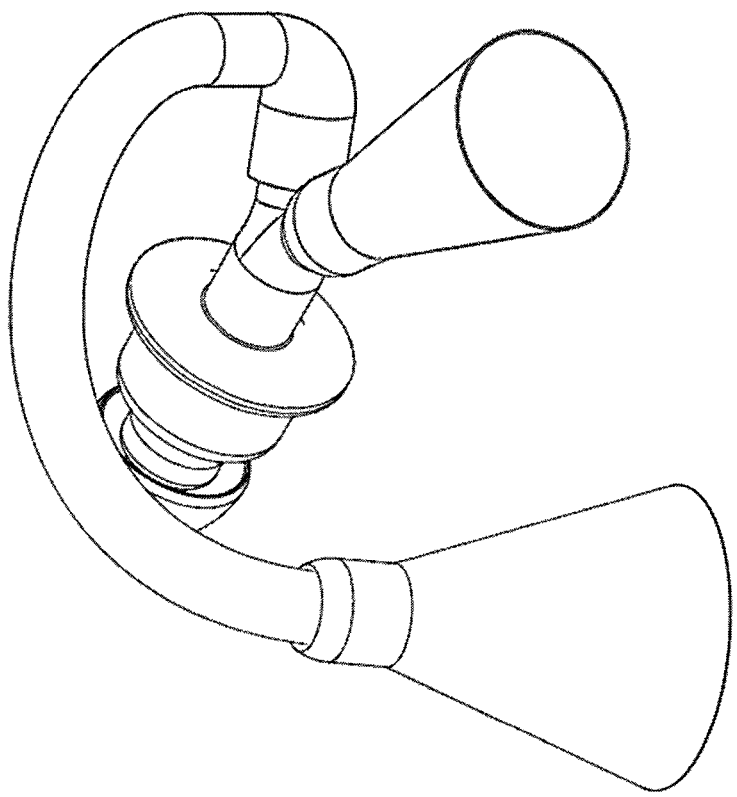
FIG. 9E is a first perspective-view diagram of tuned-frequency-spectrum earpiece 901, according to some embodiments of the present invention.

FIG. 9E is a first perspective-view diagram of tuned-frequency-spectrum earpiece 901, according to some embodiments of the present invention.

FIG. 9F is a second perspective-view diagram of tuned-frequency-spectrum earpiece 901, according to some embodiments of the present invention.

Figure 9G:
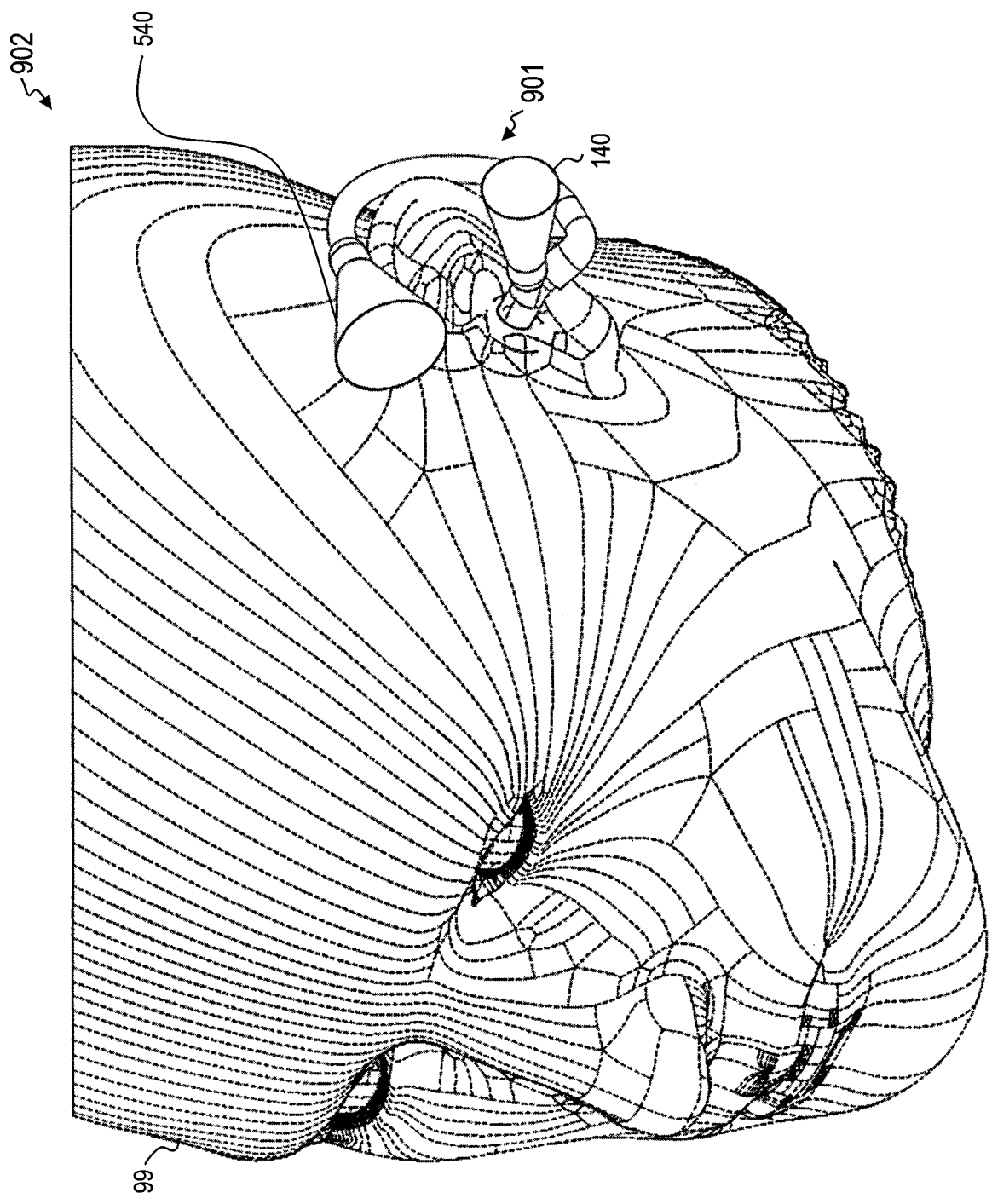
FIG. 9G is a schematic diagram of a tuned-frequency-spectrum system 902, according to some embodiments of the present invention.

FIG. 9G is a schematic diagram of a tuned-frequency-spectrum system 902, according to some embodiments of the present invention. In some embodiments, earpiece 901 is inserted into the ear of user 99 such that horn 140 faces outward from user 99 and horn 540 faces forward from user 99 and is positioned above the left ear of user 99 for this embodiment. In some embodiments, earpiece 901 is inserted into the ear of user 99 such that horn 140 and horn 540 face any other suitable directions.

FIG. 10A is a side-view diagram of a tuned-frequency-spectrum earpiece 1001, according to some embodiments of the present invention. In some embodiments, earpiece 1001 is substantially similar to earpiece 101 of FIG. 1A except that earpiece 1001 further includes a three-way connector 1060, two elbow connectors 1050, two extension tubes 1051, and three horns (e.g., in some embodiments, horn 140, horn 540, and a third horn 1040). In some embodiments, horn 1040 has a larger diameter than both horn 140 and horn 540. In some embodiments, three-way connector 1060 includes a first end coupled to base 120 and a second end that includes a first receiver portion, a second receiver portion, and a third receiver portion. In some embodiments, the receiver end of base 120 is inserted into the first end of three-way connector 1060, each of the first and second receiver portions of three-way connector 1060 is inserted into a respective elbow connector 1050, the third receiver portion of three-way connector 1060 is inserted into horn 140, each of the second ends of each elbow connector 1050 is inserted into a first end of a respective extension tube 1051, horn 540 is coupled to a second end of a first extension tube 1051, and horn 1040 is coupled to a second end of a second extension tube 1052. In some embodiments, earpiece 1001 allows audio frequencies to be received into horn 140 as it faces outward from user 99 while audio frequencies are also received into horn 540 as it faces forward from user 99 on a first side of user 99 and audio frequencies are received into horn 1040 as it faces forward from user 99 on a second side of user 99 (see FIG. 10G). In some embodiments, elbow connectors 1050 and extension tubes 1051 and 1052 are made from any suitable plastic polymer, cured plastisol, or the like. In some embodiments, elbow connectors 1050 and extension tubes 1051 are injection molded.

FIG. 10B is a cross-section view of tuned-frequency-spectrum earpiece 1001, according to some embodiments of the present invention.

Figure 10D:
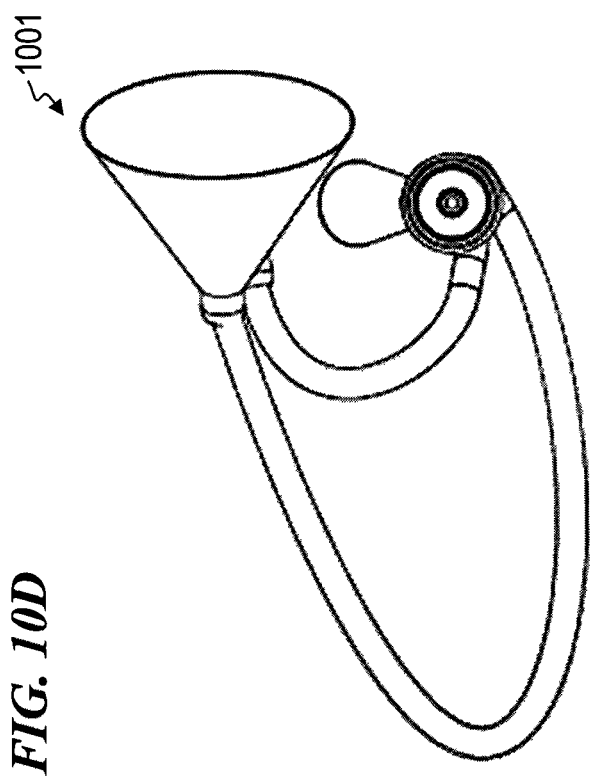
FIG. 10D is a second end-view diagram of tuned-frequency-spectrum earpiece 1001, according to some embodiments of the present invention.
Figure 10C:
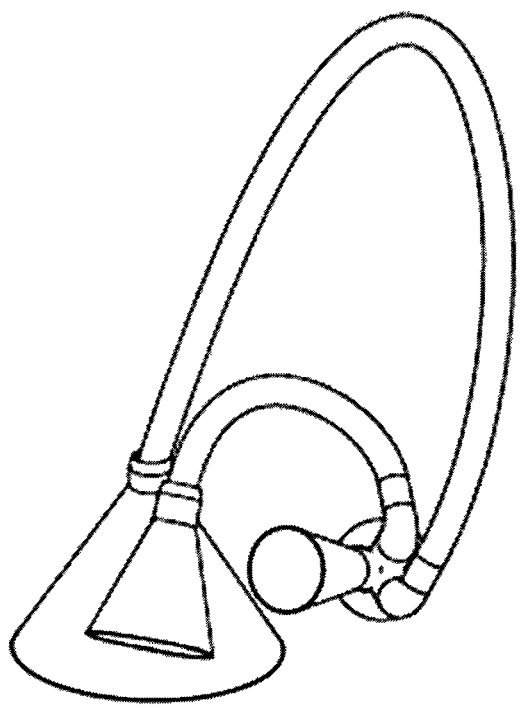
FIG. 10C is a first end-view diagram of tuned-frequency-spectrum earpiece 1001, according to some embodiments of the present invention.

FIG. 10C is a first end-view diagram of tuned-frequency-spectrum earpiece 1001, according to some embodiments of the present invention. In some embodiments, the first end-view diagram of FIG. 10C shows the view if facing earpiece 1001 from the end that includes horn 140, horn 540, and horn 1040.

FIG. 10D is a second end-view diagram of tuned-frequency-spectrum earpiece 1001, according to some embodiments of the present invention. In some embodiments, the second end-view diagram of FIG. 10D shows the view if facing the end of distal flange 125 of base 120.

Figure 10F:
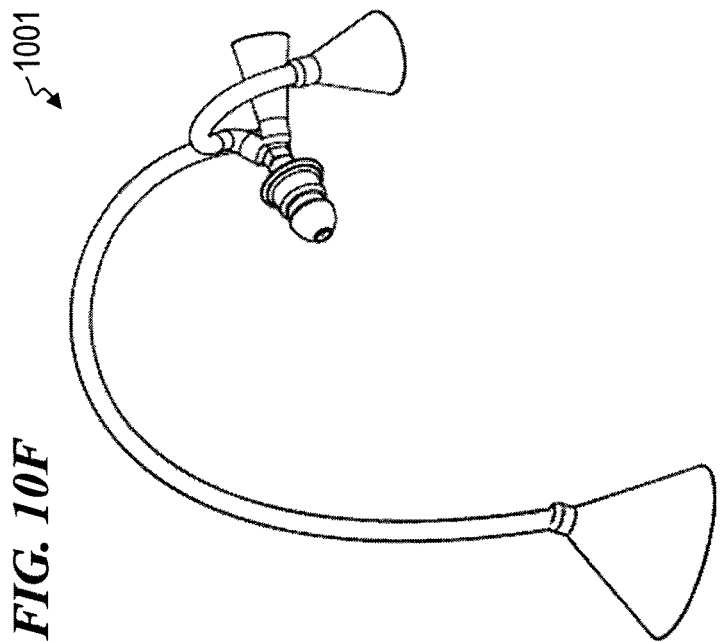
FIG. 10F is a second perspective-view diagram of tuned-frequency-spectrum earpiece 1001, according to some embodiments of the present invention.
Figure 10E:
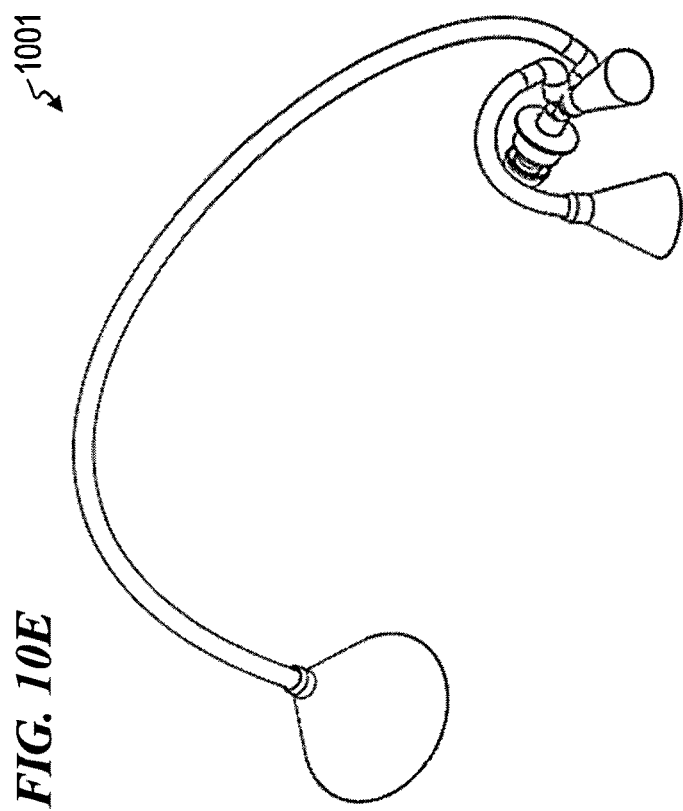
FIG. 10E is a first perspective-view diagram of tuned-frequency-spectrum earpiece 1001, according to some embodiments of the present invention.

FIG. 10E is a first perspective-view diagram of tuned-frequency-spectrum earpiece 1001, according to some embodiments of the present invention.

FIG. 10F is a second perspective-view diagram of tuned-frequency-spectrum earpiece 1001, according to some embodiments of the present invention.

Figure 10G:
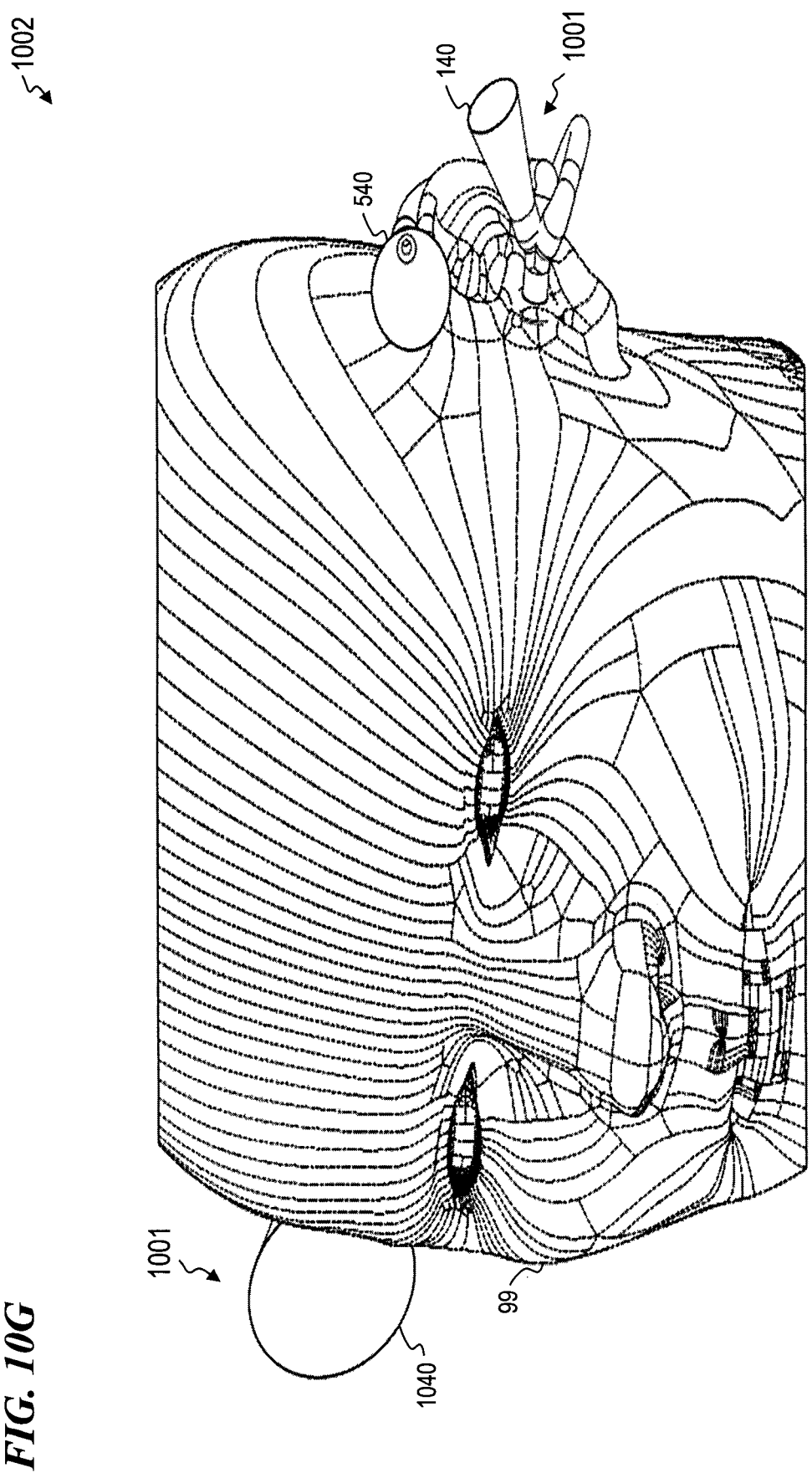
FIG. 10G is a schematic diagram of a tuned-frequency-spectrum system 1002, according to some embodiments of the present invention.

FIG. 10G is a schematic diagram of a tuned-frequency-spectrum system 1002, according to some embodiments of the present invention. In some embodiments, earpiece 1001 is inserted into the ear of user 99 such that horn 140 faces outward from user 99, horn 540 faces forward from user 99 on a first side of user 99 and is positioned above the left ear of user 99 for this embodiment, and horn 1040 faces forward from user 99 on a second side of user 99 and is positioned above the right ear of user 99 for this embodiment. In some embodiments, earpiece 1001 is inserted into the ear of user 99 such that horn 140, horn 540, and horn 1040 face any other suitable combinations of directions.

Figure 11:
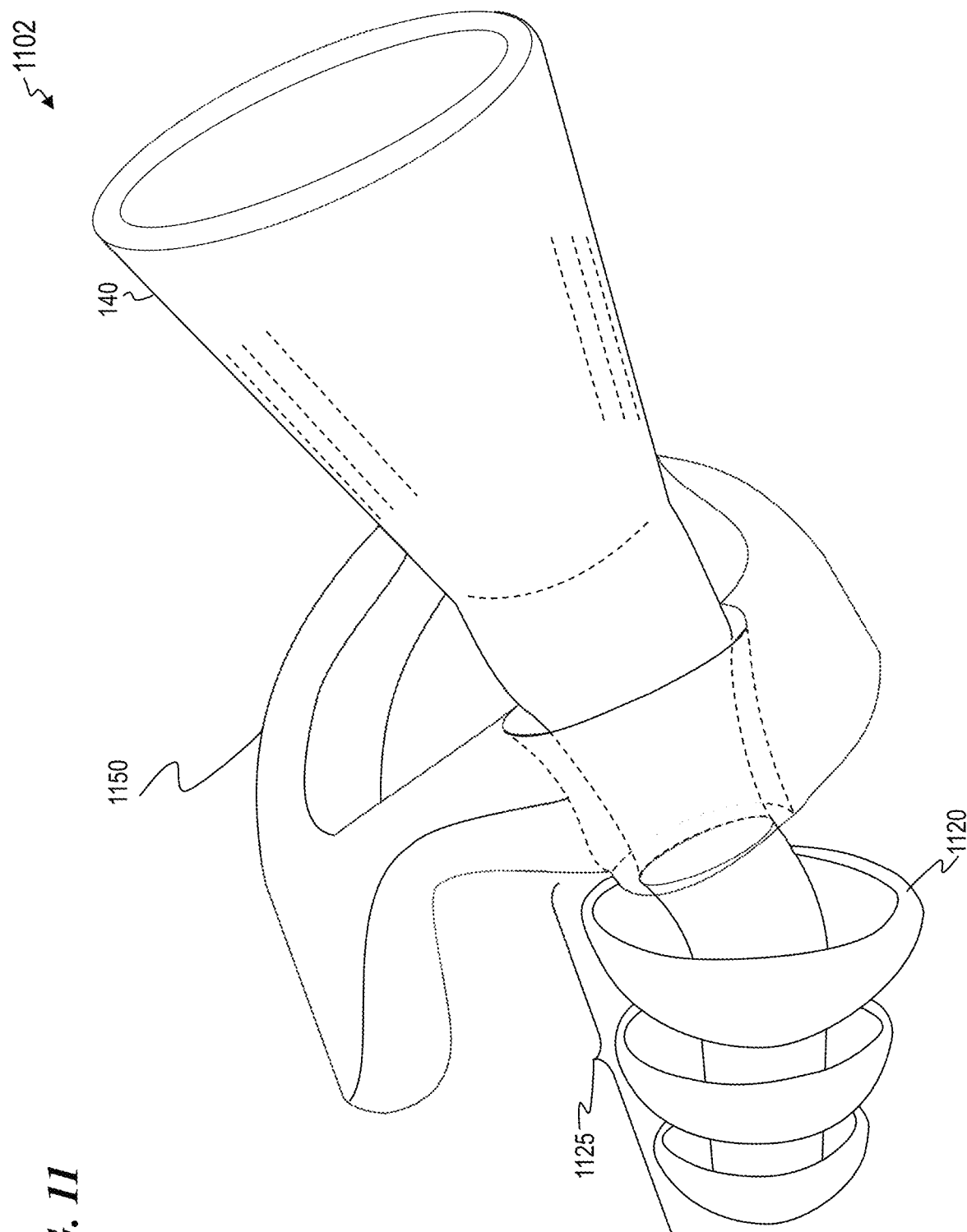
FIG. 11 is a side-view photograph of a tuned-frequency-spectrum earpiece 1101, according to some embodiments of the present invention.

FIG. 11 is a side-view photograph of a tuned-frequency-spectrum earpiece 1101, according to some embodiments of the present invention. In some embodiments, earpiece 1101 includes a base 1120 (substantially similar to base 320 of FIG. 3A except having a longer bent portion than base 320), a flange 1125 (substantially similar to flange 325 of FIG. 3A), an ear-attachment device 1150, filter system 130 (not shown) contained within the channel of base 1120, and frequency-selective sound collector 140. In some embodiments, ear-attachment device 1150 is coupled around the outside of base 1120 in a location between flange 1125 and frequency-selective sound collector 140. In some embodiments, ear-attachment device 1150 is made of any suitable plastic polymer or other suitable material and is configured to fit snugly in the outer ear of the user while flange 1125 is placed into the ear canal of the user such that earpiece 1101 is held in place on the user.

Figure 12:
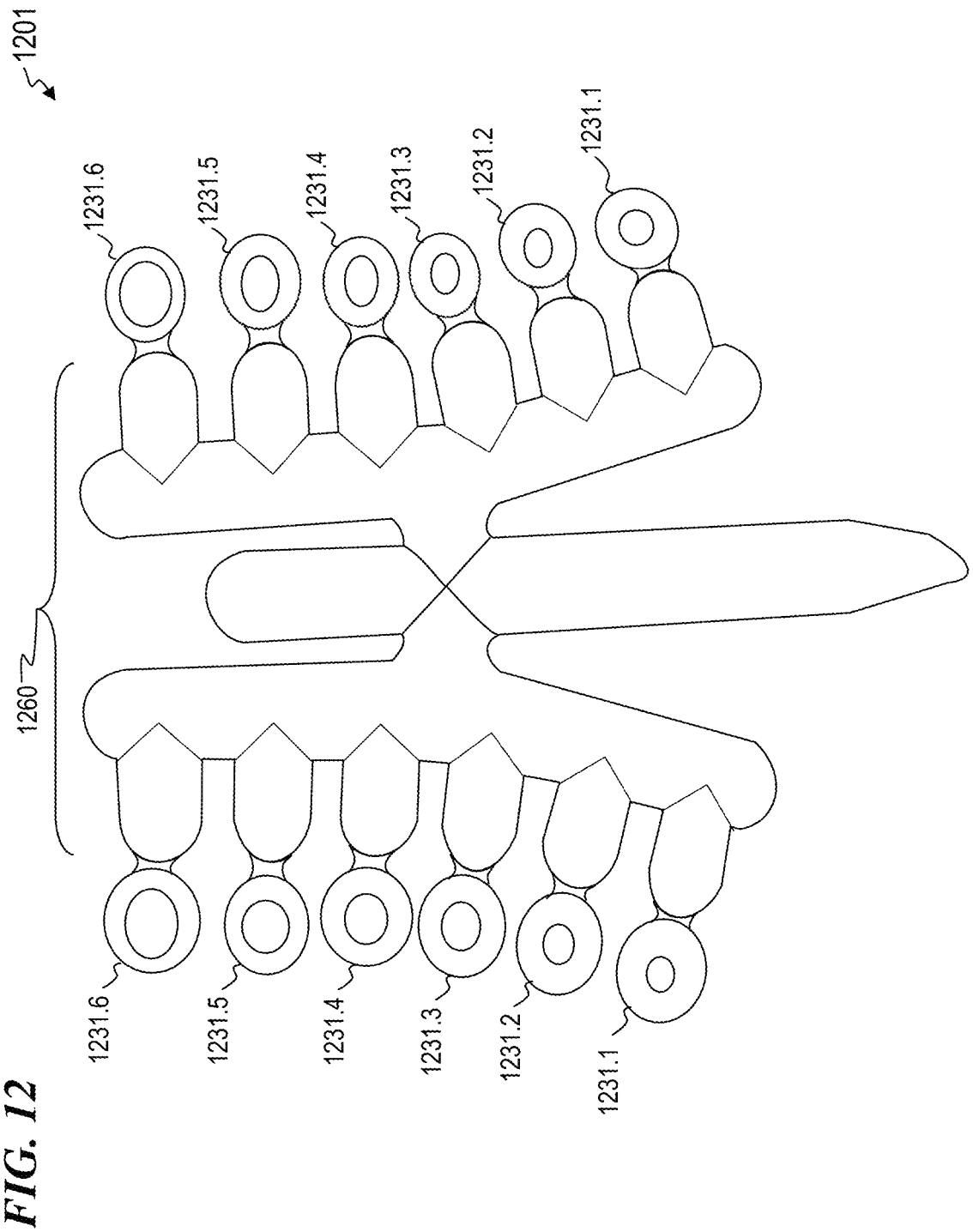
FIG. 12 is an end-view photograph of a filter-device tree 1201, according to some embodiments of the present invention.

FIG. 12 is an end-view photograph of a filter-device tree 1201, according to some embodiments of the present invention. In some embodiments, tree 1201 includes a plurality of injection-molded filter devices 1231.1, 1231.2, 1231.3, 1231.4, 1231.5, and 1231.6, each having two copies, and all attached to an injection-mold scaffolding 1260. In some embodiments, the channel diameter within each individual filter device gets larger starting with the smallest-diameter channel in filter devices 1231.1, and ending with the largest-diameter channel in filter devices 1231.6. In some embodiments, tree 1201 is made from a polypropylene, polyethylene, or any other suitable material. In some embodiments, an individual filter device removed from tree 1201 is used as the first filter device 131 of FIG. 1B (in some such embodiments, an individual filter device is removed by twisting the device off of scaffolding 1260).

In some embodiments, the present invention provides a tuned-frequency-spectrum earpiece for selectively tuning audio frequencies that enter an inner ear of a user wearing the earpiece, the earpiece including: a base having an emitter end and a receiver end, wherein the base includes a channel that passes through an entirety of the base; a sound-attenuation plug, wherein the sound-attenuation plug is configured to couple to the base such that the sound-attenuation plug surrounds at least a portion of the channel of the base; a first filter device configured to insert into the channel of the base and configured to selectively reject undesired frequencies of the audio frequencies that enter the earpiece; and a frequency-selective sound collector operatively coupled to the receiver end of the base and configured to selectively increase an amount of desired frequencies of the audio frequencies that enter the first filter device.

In some embodiments of the earpiece, the first filter device is further configured to reduce an amplitude of the audio frequencies that enter the earpiece. In some embodiments, the first filter device includes a channel that passes through an entirety of the first filter device. In some embodiments, the first filter device is made from a material that includes a polypropylene. In some embodiments, the earpiece further includes a second filter device configured to insert into the channel of the base and configured to reduce resonance in the earpiece, wherein the second filter device is located closer to the emitter end of the base than the first filter device, and wherein an air gap is located between the first filter device and the second filter device. In some embodiments, the second filter device is made from a material that includes urethane.

In some embodiments of the earpiece, the frequency-selective sound collector includes a funnel shape. In some embodiments, the base includes: a first flange at the emitter end of the base, wherein the first flange has a cup shape having a convex external surface at the emitter end of the base and an outer perimeter, wherein the cup shape is configured to engage the ear canal to create a seal in the ear canal, wherein the first flange has a concave inner surface toward the receiver end of the base, and a stop located within the cup shape of the first flange, wherein the sound-attenuation plug is configured to couple to the base such that the distal end of the sound-attenuation plug is adjacent to the stop and at least a portion of the sound-attenuation plug is within the outer perimeter of the cup shape of the first flange. In some embodiments, the receiver end of the base has a first longitudinal axis, the emitter end of the base has a second longitudinal axis, and the first longitudinal axis is at a first angle relative to the second longitudinal axis.

In some embodiments of the earpiece, the frequency-selective sound collector includes a conical funnel shape. In some embodiments, the first filter device is integrated with the base such that the base and the first filter device form a single-piece component. In some embodiments, the frequency-spectrum-shaping sound-collection horn includes an input end and a longitudinal axis, wherein a plane surface of the input end of the sound-collection horn is at a ninety-degree angle relative to the longitudinal axis of the sound-collection horn (in other embodiments, the plane surface of the input end of the sound-collection horn is at a non-90-degree angle (e.g., 45 degrees, 135 degrees, and the like) relative to the longitudinal axis of the sound-collection horn in order to more precisely aim the input end of the sound-collection horn in a desired direction). In some embodiments, the earpiece further includes an elbow connector having a first end and a second end, wherein the first end of the elbow connector is coupled to the receiver end of the base, and wherein the second end of the elbow connector is coupled to the frequency-spectrum-shaping sound-collection horn such that the elbow connector is located between the base and the sound-collection horn.

In some embodiments, the present invention provides a tuned-frequency-spectrum earpiece for selectively tuning audio frequencies that enter an inner ear of a user wearing the earpiece, the earpiece including: a base having an emitter end and a receiver end, wherein the base includes: a channel that passes through an entirety of the base, and a plurality of flanges arranged in a series at the emitter end of the base including a first flange and a second flange, wherein each of the plurality of flanges has a cup shape having a convex external surface toward the emitter end of the base and a concave inner surface toward the receiver end of the base, wherein the first flange has a first cup diameter, wherein the second flange has a second cup diameter, and wherein the first cup diameter is smaller than the second cup diameter; the earpiece further including a first filter device configured to insert into the channel of the base and configured to selectively reject undesired frequencies of the audio frequencies that enter the earpiece; the earpiece further including a frequency-selective sound collector operatively coupled to the receiver end of the base and configured to selectively increase an amount of desired frequencies of the audio frequencies that enter the first filter device. In some embodiments, the earpiece further includes an ear-attachment piece operatively coupled around the base in a location between the plurality of flanges and the frequency-selective sound collector, wherein the ear-attachment piece is configured to fit snugly within the outer ear of a user of the earpiece. In some embodiments, the frequency-selective sound collector includes one or more horn-shaped pieces, made of polymer, and having one or more internal passageways extending from relatively larger-diameter sound-entry port(s) to one or more relatively smaller-diameter sound-exit port(s) coupled to the first filter device. In some embodiments, the frequency-selective sound collector includes a plurality of horn-shaped sound-collection ports each pointed in one of a plurality of different directions to selectively receive relatively more sound energy from those plurality of different directions and relatively less sound energy from other directions.

In some embodiments, the present invention provides a method for selectively tuning audio frequencies that enter an inner ear of a user, the method including providing a base having an emitter end and a receiver end, wherein the base includes a channel that passes through an entirety of the base; providing a sound-attenuation plug; coupling the sound-attenuation plug to the base such that the sound-attenuation plug surrounds at least a portion of the channel of the base; providing a first filter device; inserting the first filter device into the channel of the base; selectively rejecting, via the first filter device, undesired frequencies of the audio frequencies that enter the earpiece; providing a frequency-selective sound collector; coupling the frequency-selective sound collector to the receiver end of the base; and selectively increasing, via the frequency-selective sound collector, an amount of desired frequencies of the audio frequencies that enter the first filter device.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A tuned-frequency-spectrum earpiece for selectively tuning audio frequencies that enter an inner ear of a user wearing the earpiece, the earpiece comprising:
   a base having an emitter end and a receiver end, and a stem portion located between the emitter end and the receiver end, wherein the base includes a channel that passes through an entirety of the base;
   a sound-attenuation plug, wherein the sound-attenuation plug surrounds at least a portion of the stem portion of the base;
   a first filter device located within the channel of the base and configured to selectively reject undesired frequencies of audio that enters the earpiece; and
   a first frequency-spectrum-shaping sound-collection horn operatively coupled to the receiver end of the base and configured to selectively increase sound intensities of desired frequencies relative to sound intensities of other frequencies of the audio that enters the first filter device.

2. The tuned-frequency-spectrum earpiece of claim 1, wherein the base is pliable and includes:
   a bendable first flange at the emitter end of the base, wherein the first flange has a cup shape having a convex external surface at the emitter end of the base and an outer perimeter, wherein the cup shape is configured to engage the ear canal to create a seal in the ear canal, wherein the first flange has a concave inner surface toward the receiver end of the base, and
   a plug-stop feature located within the cup shape of the first flange, wherein the sound-attenuation plug is configured to couple to the base such that a distal end of the sound-attenuation plug is adjacent to the plug-stop feature and at least a portion of the sound-attenuation plug is within the outer perimeter of the cup shape of the first flange and is spaced apart from the first flange.

3. The tuned-frequency-spectrum earpiece of claim 1, wherein the first filter device includes a channel that passes through an entirety of the first filter device.

4. The tuned-frequency-spectrum earpiece of claim 1, wherein the first filter device is made from a material that includes a polypropylene.

5. The tuned-frequency-spectrum earpiece of claim 1, further comprising:
   a second filter device located in the channel of the base and configured to reduce resonance in the earpiece, wherein the second filter device is located closer to the emitter end of the base than the first filter device, and wherein an air gap is located between the first filter device and the second filter device.

6. The tuned-frequency-spectrum earpiece of claim 5, wherein the second filter device is made from a material that includes urethane.

7. The tuned-frequency-spectrum earpiece of claim 5, wherein the second filter device includes cotton.

8. The tuned-frequency-spectrum earpiece of claim 1, wherein the first filter device is further configured to reduce an amplitude of the audio frequencies that enter the earpiece.

9. The tuned-frequency-spectrum earpiece of claim 1, wherein the receiver end of the base has a first longitudinal axis, wherein the emitter end of the base has a second longitudinal axis, and wherein the first longitudinal axis is at a first angle relative to the second longitudinal axis.

10. The tuned-frequency-spectrum earpiece of claim 1, wherein the frequency-selective sound collector includes a conical funnel shape.

11. The tuned-frequency-spectrum earpiece of claim 1, wherein the first filter device is integrated with the base such that the base and the first filter device form a single-piece component.

12. The tuned-frequency-spectrum earpiece of claim 1, wherein the first frequency-spectrum-shaping sound-collection horn includes an input end and a longitudinal axis, and wherein a plane surface of the input end of the first sound-collection horn is at a ninety-degree angle relative to the longitudinal axis of the first sound-collection horn.

13. The tuned-frequency-spectrum earpiece of claim 1, further comprising:
   an elbow connector having a first end and a second end, wherein the first end of the elbow connector is coupled to the receiver end of the base, and wherein the second end of the elbow connector is coupled to the first frequency-spectrum-shaping sound-collection horn such that the elbow connector is located between the base and the first sound-collection horn.

14. The tuned-frequency-spectrum earpiece of claim 1, further comprising:
   a split connector, wherein the split connector includes a first end coupled to the receiver end of the base, and a second end having a first receiver portion and a second receiver portion;
   a plurality of elbow connectors including a first elbow connector and a second elbow connector, wherein each of the plurality of elbow connectors includes a first end and a second end;
   a second frequency-spectrum-shaping sound-collection horn, wherein the first end of the first elbow connector is coupled to the first receiver portion of the split connector, and the second end of the first elbow connector is coupled to the first frequency-spectrum-shaping sound-collection horn, wherein the first end of the second elbow connector is coupled to the second receiver portion of the split connector, and the second end of the second elbow connector is coupled to the second frequency-spectrum-shaping sound-collection horn, wherein the first sound-collection horn faces a first direction, and wherein the second sound-collection horn faces a second direction, opposite the first direction.

15. The tuned-frequency-spectrum earpiece of claim 1, further comprising:
a split connector, wherein the split connector includes a first end coupled to the receiver end of the base, and a second end having a first receiver portion and a second receiver portion;
an elbow connector having a first end and a second end, wherein the first end of the elbow connector is coupled to the first receiver portion of the split connector;
an extension tube having a first end and a second end, wherein the first end of the extension tube is coupled to the second end of the elbow connector;
a second frequency-spectrum-shaping sound-collection horn, wherein the second sound-collection horn is coupled to the second end of the extension tube, and wherein the first sound-collection horn is coupled to the second receiver portion of the split connector.

16. The tuned-frequency-spectrum earpiece of claim 1, further comprising:
a three-way connector, wherein the split connector includes a first end coupled to the receiver end of the base, and a second end having a first receiver portion, a second receiver portion, and a third receiver portion;
a plurality of elbow connectors including a first elbow connector and a second elbow connector, wherein each of the plurality of elbow connectors includes a first end and a second end;
a plurality of extension tubes including a first extension tube and a second extension tube, wherein each of the plurality of extension tubes includes a first end and a second end;
a second frequency-spectrum-shaping sound-collection horn; and
a third frequency-spectrum-shaping sound-collection horn, wherein the first end of the first elbow connector is coupled to the first receiver portion of the three-way connector, and the second end of the first elbow connector is coupled to the first end of the first extension tube, wherein the first end of the second elbow connector is coupled to the second receiver portion of the three-way connector, and the second end of the second elbow connector is coupled to the first end of the second extension tube, wherein the first sound-collection horn is coupled to the third receiver portion of the three-way connector, wherein the second sound-collection horn is coupled to the second end of the first extension tube, and wherein the third sound-collection horn is coupled to the second end of the second extension tube.

17. A tuned-frequency-spectrum earpiece for selectively tuning audio frequencies that enter an inner ear of a user wearing the earpiece, the earpiece comprising:
a base having an emitter end and a receiver end, wherein the base includes:
a channel that passes through an entirety of the base, and
a plurality of flanges arranged in a series at the emitter end of the base including a first flange and a second flange, wherein each of the plurality of flanges has a cup shape having a convex external surface toward the emitter end of the base and a concave inner surface toward the receiver end of the base, wherein the first flange has a first cup diameter, wherein the second flange has a second cup diameter, and wherein the first cup diameter is smaller than the second cup diameter;
a first filter device configured to insert into the channel of the base and configured to selectively reject undesired frequencies of the audio frequencies that enter the earpiece; and
a frequency-selective sound collector operatively coupled to the receiver end of the base and configured to selectively increase an amount of desired frequencies of the audio frequencies that enter the first filter device.

18. The tuned-frequency-spectrum earpiece of claim 17, further comprising:
an ear-attachment piece operatively coupled around the base in a location between the plurality of flanges and the frequency-selective sound collector, wherein the ear-attachment piece is configured to fit within an outer ear of the user.

19. A method for selectively tuning audio frequencies that enter an inner ear of a user, the method comprising:
providing a base having an emitter end and a receiver end, wherein the base includes a channel that passes through an entirety of the base;
providing a sound-attenuation plug;
coupling the sound-attenuation plug to the base such that the sound-attenuation plug surrounds at least a portion of the channel of the base;
providing a first filter device;
inserting the first filter device into the channel of the base;
selectively rejecting, via the first filter device, undesired frequencies of the audio frequencies that enter the channel of the base;
providing a frequency-selective sound collector;
coupling the frequency-selective sound collector to the receiver end of the base; and
selectively increasing, via the frequency-selective sound collector, an amount of selected desired frequencies of those audio frequencies that are passed to the first filter device.

20. The method of claim 19, further comprising:
providing a second filter device;
inserting the second filter device into the channel of the base such that the second filter device is located closer to the emitter end of the base than the first filter device, and such that an air gap is located between the first filter device and the second filter device; and
reducing resonance in the channel of the earpiece via the second filter device.

\* \* \* \* \*